(12) United States Patent
Wang et al.

(10) Patent No.: US 11,160,860 B2
(45) Date of Patent: Nov. 2, 2021

(54) HSV ANTIGENIC PEPTIDES AND HSV PROTEIN VACCINES

(71) Applicants: Merck Sharp & Dohme Corp., Rahway, NJ (US); Dai Wang, Blue Bell, PA (US); Lan Zhang, Chalfont, PA (US)

(72) Inventors: Dai Wang, Blue Bell, PA (US); Lan Zhang, Chalfont, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 7 days.

(21) Appl. No.: 16/607,412

(22) PCT Filed: Apr. 25, 2018

(86) PCT No.: PCT/US2018/029269
§ 371 (c)(1),
(2) Date: Oct. 23, 2019

(87) PCT Pub. No.: WO2018/200613
PCT Pub. Date: Nov. 1, 2018

(65) Prior Publication Data
US 2020/0069792 A1     Mar. 5, 2020

Related U.S. Application Data

(60) Provisional application No. 62/490,090, filed on Apr. 26, 2017.

(51) Int. Cl.
| | | |
|---|---|---|
| *A61K 39/245* | (2006.01) | |
| *A61P 31/22* | (2006.01) | |
| *C07K 14/005* | (2006.01) | |
| *C12N 7/00* | (2006.01) | |

(52) U.S. Cl.
CPC ............ *A61K 39/245* (2013.01); *A61P 31/22* (2018.01); *C07K 14/005* (2013.01); *C12N 7/00* (2013.01); *C12N 2710/16622* (2013.01); *C12N 2710/16634* (2013.01)

(58) Field of Classification Search
CPC .............. A61K 39/245; A61K 2039/51; A61K 2039/55555; A61K 39/12; A61P 31/22; C07K 14/005; C07K 2319/03; C12N 7/00; C12N 2710/16622; C12N 2710/16634
See application file for complete search history.

(56) References Cited

U.S. PATENT DOCUMENTS

| 7,094,767 | B2 * | 8/2006 | Armstrong | ........... C07K 14/005 435/320.1 |
|---|---|---|---|---|
| 9,044,420 | B2 * | 6/2015 | Dubensky, Jr. | ......... A61P 31/12 |
| 2010/0330112 | A1 | 12/2010 | Long et al. | |
| 2013/0171234 | A1 | 7/2013 | Fairman et al. | |
| 2018/0303929 | A1 * | 10/2018 | Ciaramella | ........ A61K 31/7105 |

FOREIGN PATENT DOCUMENTS

| WO | 2017070623 A1 | 4/2017 |
|---|---|---|
| WO | 2018170256 A1 | 9/2018 |

OTHER PUBLICATIONS

Dropulic LK, Cohen JI. The challenge of developing a herpes simplex virus 2 vaccine. Expert Rev Vaccines. Dec. 2012;11(12):1429-40. doi: 10.1586/erv.12.129. PMID: 23252387; PMCID: PMC3593236.*
Small JC, Ertl HC. Viruses—from pathogens to vaccine carriers. Curr Opin Virol. Oct. 2011;1(4):241-5. doi: 10.1016/j.coviro.2011.07.009. PMID: 22003377; PMCID: PMC3190199.*
Alexander DJ, Aldous EW, Fuller CM. The long view: a selective review of 40 years of Newcastle disease research. Avian Pathol. 2012;41(4):329-35. doi: 10.1080/03079457.2012.697991. PMID: 22834545.*
Gaskell R, Dawson S, Radford A, Thiry E. Feline herpesvirus. Vet Res. Mar.-Apr. 2007;38(2):337-54. doi: 10.1051/vetres:2006063. Epub Feb. 13, 2007. PMID: 17296160.*
Whitley R, Baines J. Clinical management of herpes simplex virus infections: past, present, and future. F1000Res. Oct. 31, 2018;7:F1000 Faculty Rev-1726, doi: 10.12688/f1000research. 16157.1. PMID: 30443341; PMCID: PMC6213787.*
Rogalin HB, Heldwein EE. Characterization of Vesicular Stomatitis Virus Pseudotypes Bearing Essential Entry Glycoproteins gB, gD, gH, and gL of Herpes Simplex Virus 1. J Virol. Oct. 28, 2016;90(22):10321-10328.*
Tang J, Yang T, Ghosh HP, Geller AI. Helper virus-free HSV-1 vectors packaged both in the presence of VSV G protein and in the absence of HSV-1 glycoprotein B support gene transfer into neurons in the rat striatum. J Neurovirol. Dec. 2001;7(6):548-55. doi: 10.1080/135502801753248132. PMID: 11704887.*
UniProt Accession No. D6QV07, Envelope glycoprotein B (Homo Sapiens—online), Retrieved from website: URL: https://www.uniprot.org/uniprot/D6QV07—Jul. 13, 2010.
Garcia, N.J. et al., Modulation of Epstein-Barr Virus Glycoprotein B (gB) Fusion Activity by the gB Cytoplasmic Tail Domain, mBio, 2013, 1-11, 4(1).
Kirchmeier, M. et al., Enveloped Virus-Like Particle Expression of Human Cytomegalovirus Glycoprotein B Antigen Induces Antibodies with Potent and Broad Neutralizing Activity, Clinical and Vaccine Immunology, 2013, 174-180, 21(2).
Lucchese, G et al, How a single amino acid change may alter the immunological information of a peptide, Frontiers in Bioscience: Elite Edition, 2012, 1843-1852, vol. 4, No. 5.
Uniprot, Envelope glycoprotein B, UniProt Accession No. D6QV07, 2010, 1-6, D6QV07.

* cited by examiner

*Primary Examiner* — Rachel B Gill
(74) *Attorney, Agent, or Firm* — Andrew W. Custer; Anna L. Cocuzzo

(57) ABSTRACT

HSV glycoprotein B-VSV-G1 fusion proteins and variants thereof, HSV glycoprotein C antigenic peptide constructs and variants thereof, HSV immunogenic compositions and protein vaccines including the peptide constructs, and HSV DNA vaccines encoding the amino acid sequence of the peptide constructs, as well as methods of using the vaccines and compositions comprising the vaccines.

21 Claims, 18 Drawing Sheets

Specification includes a Sequence Listing.

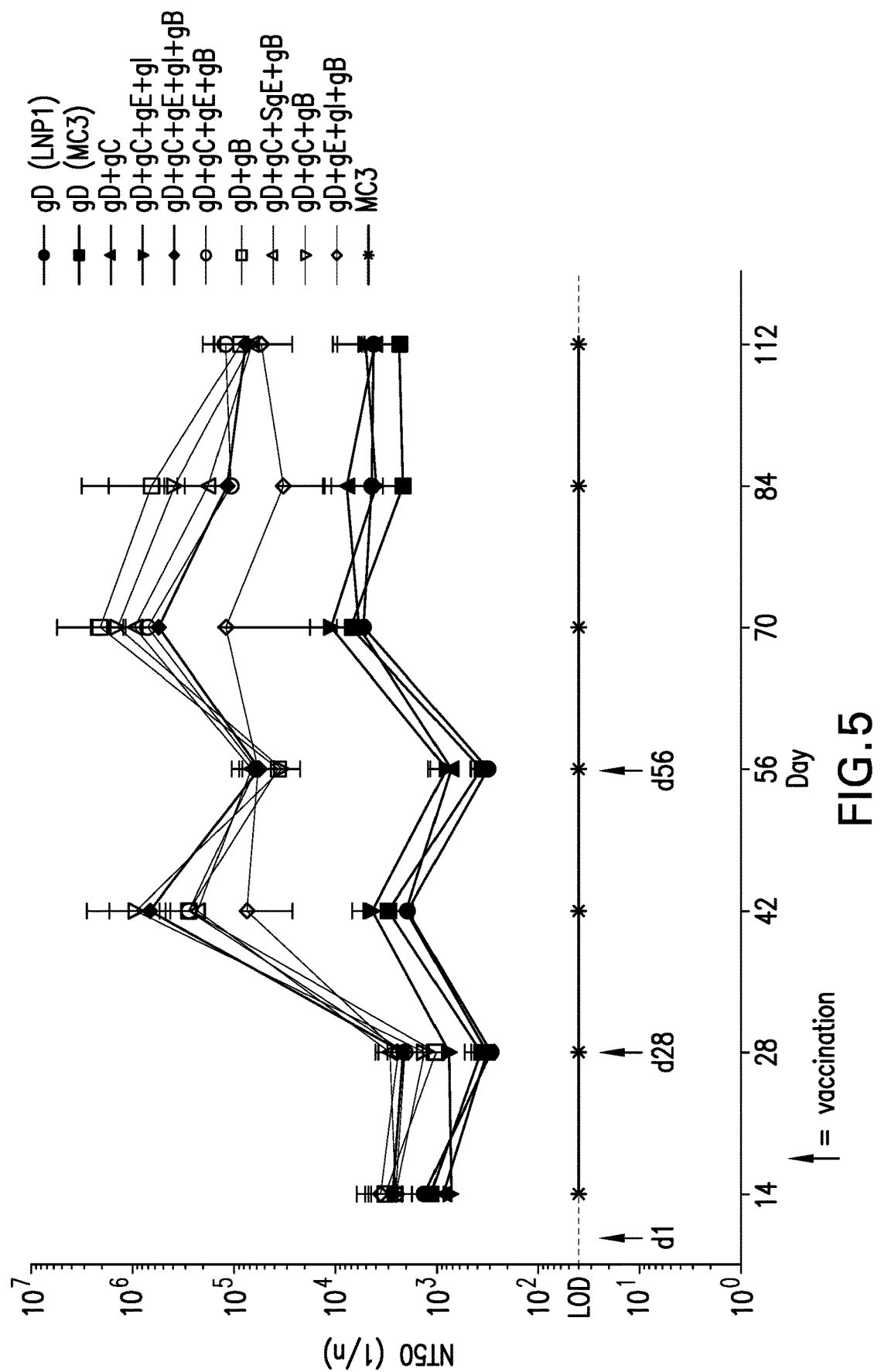

HSV ANTIGENIC PEPTIDES AND HSV PROTEIN VACCINES

CROSS REFERENCE TO RELATED APPLICATIONS

This application is the National Stage of International Application No. PCT/US2018/029269 filed on Apr. 25, 2018, which claims the benefit under 35 U.S.C. 119(e) of U.S. Provisional Application No. 62/490,090, filed Apr. 26, 2017, each of which is herein incorporated by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "24450 US PCT SEQTXT.txt", creation date of Aug. 7, 2019, and a size of 69.2 KB. This sequence listing submitted via EFS-Web is part of the specification and is herein incorporated by reference in its entirety.

BACKGROUND OF INVENTION

Herpes simplex viruses (HSV) are double-stranded linear DNA viruses in the Herpesviridae family. Two members of the herpes simplex virus family infect humans—known as HSV-1 and HSV-2. Symptoms of HSV infection include the formation of blisters in the skin or mucous membranes of the mouth, lips, and/or genitals. HSV is a neuroinvasive virus that can cause sporadic recurring episodes of viral reactivation in infected individuals. HSV is transmitted by contact with an infected area of the skin during a period of viral activation.

SUMMARY OF INVENTION

In one aspect, the present invention provides HSV virus vaccines comprising at least one HSV antigenic polypeptide selected from any of SEQ ID NOs: 1-5. In certain embodiments, the HSV vaccine comprises at least one isolated antigenic polypeptide selected from the group consisting of: (i) a mature amino acid sequence of SEQ ID NO: 1, or a variant thereof; (ii) a mature amino acid sequence of SEQ ID NO: 2, or variant thereof; (iii) a mature amino acid sequence of SEQ ID NO: 3, or variant thereof; (iv) a mature amino acid sequence of SEQ ID NO: 4, or variant thereof; and (v) a mature amino acid sequence of SEQ ID NO: 5, or a variant thereof. In one embodiment, the variant of SEQ ID NO: 2 comprises an alanine at position 368; the variant of SEQ ID NO: 3 comprises an alanine at position 323; the variant of SEQ ID NO: 4 comprises an alanine at position 327; and the variant of SEQ ID NO: 5 comprises an alanine at position 333. In another embodiment, the variant of any one of SEQ ID NOs: 1-5 is a sequence having at least 90%, 95%, 96%, 97.5%, 98%, 99%, or 95-99% identity to a mature amino acid sequence of any one of SEQ ID NOs: 1-5, provided that the variant of SEQ ID NO: 2 comprises an alanine at position 368; the variant of SEQ ID NO: 3 comprises an alanine at position 323; the variant of SEQ ID NO: 4 comprises an alanine at position 327; and the variant of SEQ ID NO: 5 comprises an alanine at position 333. In one embodiment, the variant of SEQ ID NOs: 2, 3, 4, or 5 is not SEQ ID NO: 11.

In another aspect, also provided is an HSV virus vaccine comprising an isolated polynucleotide sequence comprising SEQ ID NO:6 or variant thereof. In another embodiment, provided is an HSV virus vaccine, comprising an isolated DNA sequence encoding an amino acid sequence identified by any one of SEQ ID NO: 1-5 or a variant thereof.

In one aspect, provided is an HSV vaccine comprising at least two isolated antigenic polypeptides, wherein the first polypeptide comprises an HSV glycoprotein D or immunogenic fragment thereof and the second polypeptide comprises an HSV glycoprotein B or immunogenic fragment thereof, wherein the HSV glycoprotein B or immunogenic fragment thereof comprises SEQ ID NO:1 or a variant thereof. In one embodiment, the HSV glycoprotein D or immunogenic fragment thereof has the sequence identified by SEQ ID NO: 7 or 8. In one embodiment, the vaccine further comprises a third isolated antigenic polypeptide, wherein the third antigenic polypeptide comprises an HSV glycoprotein C or immunogenic fragment thereof. In one embodiment, the HSV glycoprotein C or immunogenic fragment thereof comprises any of SEQ ID NOs: 2-5 or variant thereof. In one embodiment, the variant of SEQ ID NO: 2 comprises an alanine at position 368; the variant of SEQ ID NO: 3 comprises an alanine at position 323; the variant of SEQ ID NO: 4 comprises an alanine at position 327; and the variant of SEQ ID NO: 5 comprises an alanine at position 333. In another embodiment, the HSV glycoprotein C or immunogenic fragment thereof has the sequence identified by SEQ ID NO: 11 or 12. In another embodiment, the vaccine further comprises a fourth isolated antigenic polypeptide, wherein the fourth antigenic polypeptide comprises an HSV glycoprotein E, or immunogenic fragment thereof. In one embodiment, the HSV glycoprotein E or immunogenic fragment thereof has the sequence identified by SEQ ID NO: 13 or 14. In an additional embodiment, the vaccine comprises a fifth isolated antigenic polypeptide, wherein the fifth antigenic polypeptide comprises an HSV glycoprotein I or immunogenic fragment thereof. In one embodiment, the HSV glycoprotein I or immunogenic fragment thereof has the sequence identified by SEQ ID NO: 15 or 16.

In a further aspect, provided is an HSV virus vaccine comprising at least two isolated antigenic polypeptides, wherein the first polypeptide comprises an HSV glycoprotein D or immunogenic fragment thereof and the second polypeptide comprises an HSV glycoprotein C or immunogenic fragment thereof, wherein the HSV glycoprotein C or immunogenic fragment thereof comprises any one of SEQ ID NOs: 2-5 or a variant thereof. In one embodiment, the variant of SEQ ID NO: 2 comprises an alanine at position 368; the variant of SEQ ID NO: 3 comprises an alanine at position 323; the variant of SEQ ID NO: 4 comprises an alanine at position 327; and the variant of SEQ ID NO: 5 comprises an alanine at position 333. In another embodiment, the HSV glycoprotein C or immunogenic fragment thereof is not SEQ ID NO: 11 or 12. In one embodiment, the HSV glycoprotein D or immunogenic fragment thereof has the sequence identified by SEQ ID NO: 7 or 8. In one embodiment, the vaccine comprises a third antigenic polypeptide, wherein the third polypeptide comprises an HSV glycoprotein E or immunogenic fragment thereof. In one embodiment, the HSV glycoprotein E or immunogenic fragment thereof has the sequence identified by SEQ ID NO: 13 or 14. In another embodiment, the vaccine comprises a fourth antigenic polypeptide, wherein the fourth polypeptide comprises an HSV glycoprotein I or immunogenic fragment thereof. In one embodiment, the HSV glycoprotein I or immunogenic fragment thereof has the sequence identified by SEQ ID NO: 15 or 16.

In another aspect, provided is an HSV virus vaccine comprising at least two isolated antigenic polypeptides, wherein the first polypeptide comprises an HSV glycoprotein B or immunogenic fragment thereof and the second polypeptide comprises an HSV glycoprotein C or immunogenic fragment thereof, wherein the HSV glycoprotein C or immunogenic fragment thereof comprises any one of SEQ ID NOs: 2-5 or a variant thereof. In one embodiment, the variant of SEQ ID NO: 2 comprises an alanine at position 368; the variant of SEQ ID NO: 3 comprises an alanine at position 323; the variant of SEQ ID NO: 4 comprises an alanine at position 327; and the variant of SEQ ID NO: 5 comprises an alanine at position 333. In another embodiment, the HSV glycoprotein C or immunogenic fragment thereof is not SEQ ID NO: 11 or 12. In one embodiment, the HSV glycoprotein B has the sequence identified by any of SEQ ID Nos: 1, 9 or 10. In one embodiment, the vaccine comprises a third antigenic polypeptide, wherein the third polypeptide comprises the HSV glycoprotein D or immunogenic fragment thereof. In one embodiment, the HSV glycoprotein D or immunogenic fragment thereof has the sequence identified by SEQ ID NO: 7 or 8. In one embodiment, the vaccine comprises a fourth antigenic polypeptide, wherein the fourth polypeptide comprises an HSV glycoprotein E or immunogenic fragment thereof. In one embodiment, the HSV glycoprotein E or immunogenic fragment thereof has the sequence identified by SEQ ID NO: 13 or 14. In another embodiment, the vaccine comprises a fifth antigenic polypeptide, wherein the fifth polypeptide comprises an HSV glycoprotein I or immunogenic fragment thereof. In one embodiment, the HSV glycoprotein I or immunogenic fragment thereof has the sequence identified by SEQ ID NO: 15 or 16.

In another aspect of the invention, provided is a trivalent HSV virus vaccine comprising (i) an HSV glycoprotein B or immunogenic fragment thereof, an HSV glycoprotein D or immunogenic fragment thereof, and an HSV glycoprotein C or immunogenic fragment thereof, wherein the HSV glycoprotein C or immunogenic fragment thereof comprises any one of SEQ ID Nos: 2-5, or variant thereof. In one embodiment, the variant of SEQ ID NO: 2 comprises an alanine at position 368; the variant of SEQ ID NO: 3 comprises an alanine at position 323; the variant of SEQ ID NO: 4 comprises an alanine at position 327; and the variant of SEQ ID NO: 5 comprises an alanine at position 333. In another embodiment, the HSV glycoprotein C or immunogenic fragment thereof is not SEQ ID NO: 11 or 12. In one embodiment, the HSV glycoprotein B has the sequence identified by any of SEQ ID Nos: 1, 9 or 10. In one embodiment, the HSV glycoprotein D or immunogenic fragment thereof has the sequence identified by SEQ ID NO: 7 or 8.

A further aspect of the invention provides an isolated peptide comprising the amino acid sequence of any one of SEQ ID Nos: 1-5 or the mature amino acid sequence of any one of SEQ ID Nos: 1-5, or a variant thereof, wherein the variant of SEQ ID NO: 2 comprises an alanine at position 368; the variant of SEQ ID NO: 3 comprises an alanine at position 323; the variant of SEQ ID NO: 4 comprises an alanine at position 327; and the variant of SEQ ID NO: 5 comprises an alanine at position 333. In one embodiment, the variant has 95%, 96%, 97%, 98%, or 99% homology to SEQ ID NO: 1, 2, 3, 4, or 5, respectively, or 95%, 96%, 97%, 98%, or 99% homology to the mature amino acid sequence of SEQ ID NO:1, 2, 3, 4, or 5, respectively.

In another aspect, provided is an antibody molecule, including full length antibodies and antibody derivates, directed against the novel HSV antigen sequences disclosed herein as SEQ ID NO: 1-5.

In some embodiments, the vaccine is multivalent, and comprises at least two to ten, two, three, four, or five, or ten HSV antigenic polypeptides.

Some embodiments of the present disclosure provide methods of inducing an antigen specific immune response in a subject, comprising administering to the subject any of the vaccine compositions provided herein in an amount effective to produce an antigen-specific immune response. In some embodiments, the vaccine is a combination vaccine comprising a combination of different HSV antigenic polypeptides.

In some embodiments, an antigen-specific immune response comprises a T cell response or a B cell response.

In some embodiments, a method of producing an antigen-specific immune response comprises administering to a subject a single dose (no booster dose) of an HSV vaccine of the present disclosure. In some embodiments, the method of producing an antigen-specific immune response further comprises administering to the subject an HSV vaccine of the present disclosure. Additional doses of an HSV vaccine may be administered.

In some embodiments, an HSV vaccine is administered to a subject by intradermal injection or intramuscular injection. In one embodiment, an HSV vaccine is administered by intramuscular injection.

Some embodiments of the present disclosure provide methods of inducing an antigen-specific immune response in the subject, including administering to a subject an HSV vaccine described herein in an effective amount to produce an, antigen specific immune response in a subject. Antigen specific immune responses in a subject may be determined, in some embodiments, by assaying for antibody titer (for titer of an antibody that binds to an HSV antigenic polypeptide) following administration to the subject of any of the HSV vaccines of the present disclosure.

The details of various embodiments of the disclosure are set forth in the description below. Other features, objects, and advantages of the disclosure will be apparent from the description and from the claims.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

FIG. 5 is a graph showing NT50 titer (neutralizing), with complement, as a function of time.

FIG. 7 is a graph showing FACS binding for the gC variants described herein. S33A corresponds to SEQ ID NO: 5, F327A corresponds to SEQ ID NO: 4, D323A corresponds to SEQ ID NO:3 and W368A corresponds to SEQ ID NO:2.

FIGS. 8*a* and 8*b* are graphs showing serum neutralization titers with complement (FIG. 8*a*) and without complement (FIG. 8*b*).

FIG. 9 shows the primary disease daily lesions scoring in HSV-2 challenged guinea pigs.

FIGS. 10*a* and 10*b* show the vaginal viral load at day 2 post HSV-2 challenge in guinea pigs as determined by plaque assay (FIG. 10*a*) and PCR (FIG. 10*b*)

FIG. 11 shows the number of HSV-2 copies in dorsal root ganglia of guinea pigs 48 days post HSV-2 challenge as determined by PCR.

FIG. 12 shows HSV-2 serum neutralization titers induced by gC2 wild type and c3b binding mutants in mice.

FIG. 13 shows c3b binding competition antibody titer induced by the gC2 wild type and c3b binding mutants in mice.

FIGS. 14*a* and 14*b* show CD4+ and CD8+ responses induced by the gC2 wild type and c3b binding mutants in mice.

FIG. 15 shows vaginal swab titers post HSV-2 challenge in mice vaccinated with vehicle, the gC2 wild type or the various gC c3b binding mutants in mice.

FIG. 16 shows serum neutralization titers with complement and without complement.

DETAILED DESCRIPTION

"Isolated" polypeptides or polynucleotides are at least partially free of other biological molecules from the cells or cell cultures in which they are produced. Such biological molecules include other nucleic acids, proteins, lipids, carbohydrates, or other material such as cellular debris and growth medium. It may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the polypeptides or polynucleotides.

Lipid Nanoparticles

As used herein, "lipid nanoparticle" or "LNP" refers to any lipid composition that can be used to deliver a product, including, but not limited to, liposomes or vesicles, wherein an aqueous volume is encapsulated by amphipathic lipid bilayers single; unilamellar or multiple; multilamellar), or, in other embodiments, wherein the lipids coat an interior comprising a prophylactic product or lipid aggregates or micelles, wherein the lipid encapsulated therapeutic product is contained within a relatively disordered lipid mixture. Except where noted, the lipid nanoparticle does not need to have the antigenic polypeptide incorporated therein and may be used to deliver a product when in the same formulation.

As used herein, "polyamine" means compounds having two or more amino groups. Examples include putrescine, cadaverine, spermidine, and spermine.

Unless otherwise specified, mole % refers to a mole percent of total lipids. Generally, the LNPs of the compositions of the invention are composed of one or more cationic lipids (including ionizable cationic lipids) and one or more poly(ethyleneglycol)-lipids (PEG-lipids). In certain embodiments, the LNPs further comprise one or more non-cationic lipids. The one or more non-cationic lipids can include a phospholipid, phospholipid derivative, a sterol, a fatty acid, or a combination thereof.

Cationic lipids and ionizable cationic lipids suitable for the LNPs are described herein. Ionizable cationic lipids are characterized by the weak basicity of their lipid head groups, which affects the surface charge of the lipid in a pH-dependent manner, rendering them positively charged at acidic pH but close to charge-neutral at physiologic pH. Cationic lipids are characterized by monovalent or multivalent cationic charge on their headgroups, which renders them positively charged at neutral pH. In certain embodiments, the cationic and ionizable lipid is capable of complexing with hydrophilic bioactive molecules to produce a hydrophobic complex that partitions into the organic phase of a two-phase aqueous/organic system. It is contemplated that both monovalent and polyvalent cationic lipids may be utilized to form hydrophobic complexes with bioactive molecules.

Preferred cationic and ionizable cationic lipids for use in forming the LNPs include, but are not limited to, N,N-dioleyl-N,N-dimethylammonium chloride ("DODAC"); N-(2,3dioleyloxy)propyl)-N,N,Ntrimethylammonium chloride ("DOTMA"); N,NdistearylN,N-dimethylammonium bromide ("DDAB"); N-(2,3dioleoyloxy)propyl)-N,N,N-trimethylammonium chloride ("DODAP"); 1,2 bis (oleoyloxy)-3-(trimethylammonio) propane (DOTAP); 3-(N—(N, N-dimethylaminoethane)-carbam-oyl)cholesterol ('DC-Chol"); diheptadecylamidoglycylspermidine ("DHGS") and N-(1,2-dimyristyloxyprop-3-yl)-N,N-dimethyl-N-hycloxyethyl ammonium bromide ("DMRIE"). Additionally, a number of commercial preparations of cationic lipids, as well as other components, are available which can be used in the present invention. These include, for example, LIPOFECTIN® (commercially available cationic lipid nanoparticles comprising DOTMA and 1,2dioleoyl-sn-3-phosphoethanolamine ("DOPE"), from GIBCOBRL, Grand Island, N.Y., USA); and LIPOFECTAMINE® (commercially available cationic lipid nanoparticles comprising N-(1-(2,3dioleyloxy)propyl)N-(2-(sperminecarboxamido)ethyl)-N,N-dimethylammonium trifluoroacetate ("DOSPA') and ("DOPE"), from (GIBCOBRL). The following lipids are cationic and have a positive charge at below physiological pH: DODAP, DODMA, DMDMA, 1,2-DiLinoleyloxy-N,N-dimethylaminopropane (DLinDMA), 4-(2,2-diocta-9,12-dienyl-[1,3]dioxolan-4-ylmethyl)-dimethylamine, DLinKDMA (WO 2009/132131 A1), DLin-K-C2-DMA (WO2010/042877), DLin-M-C3-DMA (WO2010/146740 and/or WO2010/105209), DLin-MC3-DMA (heptatriaconta-6,9,28,31-tetraen-19-yl 4-(dimethylamino)butanoate; Jayaraman et al., 2012, Angew. Chem. Int. Ed. Engl. 51:8529-8533), 2-{4-[(3β)-cholest-5-en-3-yloxy]butoxy}-N,N-dimethyl-3-[(9Z, 12Z)-octadeca-9,12-dienlyloxyl]propan-1-amine) (CLinDMA), and the like. Other cationic lipids suitable for use in the invention include, e.g., the cationic lipids described, in U.S. Pat. Nos. 5,208,036, 5,264,618, 5,279,833 and 5,283,185, and U.S. Patent Application Publication Nos. 2008/0085870 and 2008/0057080. Other cationic lipids suitable for use in the invention include, e.g., Lipids E0001-E0118 or E0119-E0180 as disclosed in Table 6 (pages 112-139) of International Patent Application Publication No. WO2011/076807 (which also discloses methods of making, and methods of using these cationic lipids).

Figure 1:
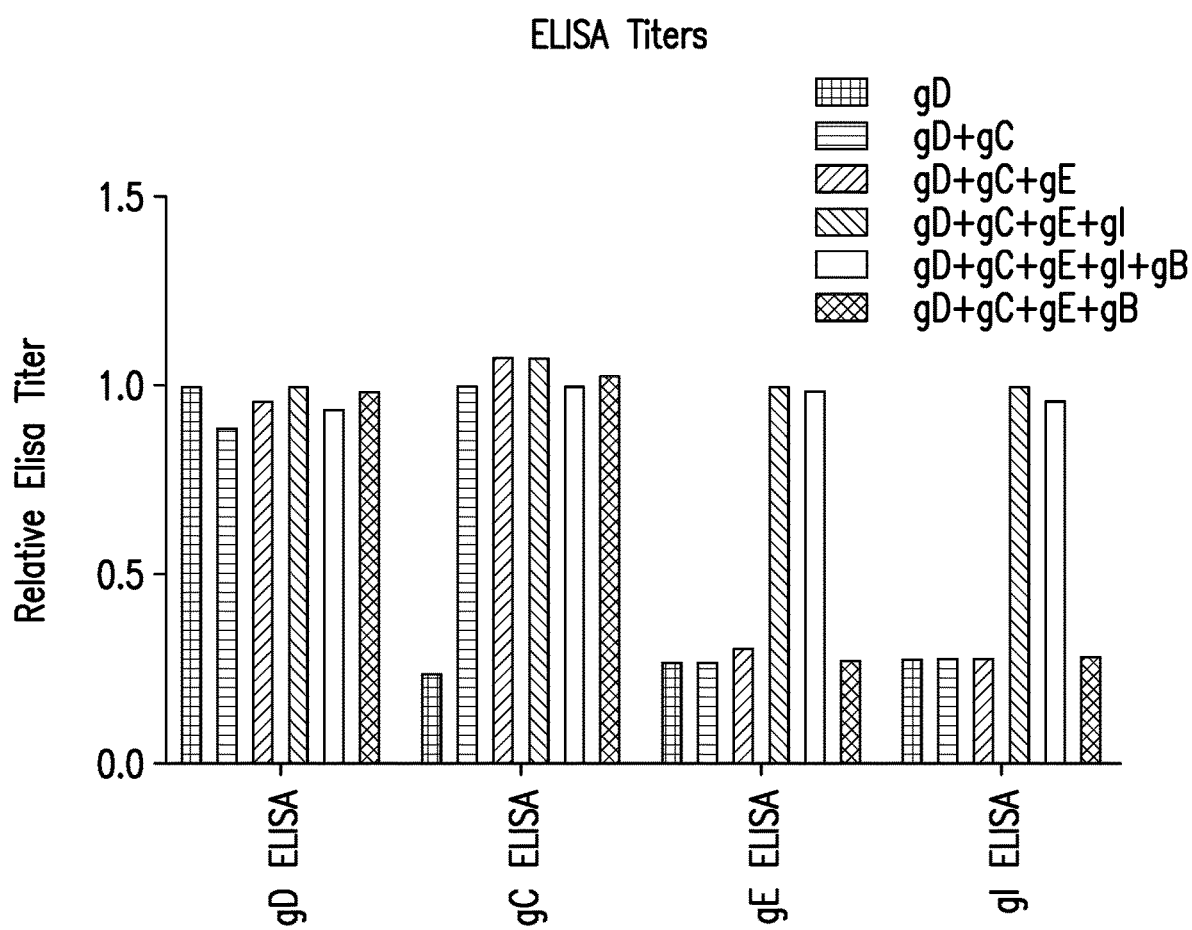
FIG. 1 is a graph showing various gD, gC, gE, and gI ELISA titers for HSV combination vaccines, including gD alone, gD+gC, gD+gC+gE, gD+gC+gE+gI, gD+gC+gE+gI+gB, and gD+gC+gE+gB.

In certain aspects of this embodiment of the invention, the LNPs comprise one or more of the following ionizable cationic lipids: DLinDMA, DlinKC2DMA DLin-MC3-DMA, CLinDMA, or S-Octyl CLinDMA (See International Patent Application Publication No. WO2010/021865).

In certain aspects of this embodiment of the invention, LNPs comprise one or more ionizable cationic lipids described in International Patent Application Publication No. WO2011/022460 A1, or any pharmaceutically acceptable salt thereof, or a stereoisomer of any of the compounds or salts therein.

When structures of the same constitution differ in respect to the spatial arrangement of certain atoms or groups, they are stereoisomers, and the considerations that are significant in analyzing their interrelationships are topological. If the relationship between two stereoisomers is that of an object and its nonsuperimposable mirror image, the two structures are enantiomeric, and each structure is said to be chiral. Stereoisomers also include diastereomers, cis-trans isomers and conformational isomers. Diastereoisomers can be chiral or achiral, and are not mirror images of one another. Cis-trans isomers differ only in the positions of atoms relative to a specified plane in cases where these atoms are, or are considered as if they were, parts of a rigid structure. Conformational isomers are isomers that can be interconverted by rotations about formally single bonds. Examples of such conformational isomers include cyclohexane conformations with chair and boat conformers, carbohydrates, linear alkane conformations with staggered, eclipsed and gauche conformers, etc. See J. Org. Chem. 35, 2849 (1970).

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, enantiomers are identical except that they are non-superimposable mirror images of one another. A mixture of enantiomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the Formulas of the invention, it is understood that both the (R) and (S) configurations of the chiral carbon, and hence both enantiomers and mixtures thereof, are embraced within the Formula. As is used in the art, when it is desired, to specify the absolute configuration about a chiral carbon, one of the bonds to the chiral carbon can be depicted as a wedge (bonds to atoms above the plane) and the other can be depicted as a series or wedge of short parallel lines (bonds to atoms below the plane). The Cahn-Inglod-Prelog system can be used to assign the (R) or (S) configuration to a chiral carbon.

When the compounds of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%.

When a compound of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

The LNPs may also comprise any combination of two or more of the cationic lipids described herein. In certain aspects, the cationic lipid typically comprises from about 0.1 to about 99.9 mole % of the total lipid present in said particle. In certain aspects, the cationic lipid can comprise from about 80 to about 99.9% mole %. In other aspects, the cationic lipid comprises from about 2% to about 70%, from about 5% to about 50%, from about 10% to about 45%, from about 20% to about 99.8%, from about 30% to about 70%, from about 34% to about 59%, from about 20% to about 40%, or from about 30% to about 40% (mole %) of the total lipid present in said particle.

The LNPs described herein can further comprise a non-cationic lipid, which can be any of a variety of neutral uncharged, zwitterionic or anionic lipids capable of producing a stable complex. They are preferably neutral, although they can be negatively charged. Examples of noncationic lipids useful in the present invention include phospholipid-related materials, such as natural phospholipids, synthetic phospholipid derivatives, fatty acids, sterols, and combinations thereof. Natural phospholipids include phosphatidylcholine (PC), phosphatidylethanolamine (PE), and phosphatidylglycerol (PG), phosphatidylserine (PS), phosphatidylinositol (PI), Phosphatidic acid (phosphatidate) (PA), dipalmitoylphosphatidylcholine, monoacyl-phosphatidylcholine (lyso PC), 1-palmitoyl-2-oleoyl-sn-glycero-3-phosphocholine (POPC), N-Acyl-PE, phosphoinositides, and phosphosphingolipids. Phospholipid derivatives include phosphatidic acid (DMPA, DPPA, DSPA), phosphatidylcholine (DDPC, DLPC, DMPC, DPPC, DSPC, DOPC, POPC, DEPC), phosphatidylglycerol (DMPG, DPPG, DSPG, POPG), phosphatidylethanolamine (DMPE, DPPE, DSPE DOPE), and phosphatidylserine (DOPS). Fatty acids include C14:0, palmitic acid (C16:0), stearic acid (C18:0), oleic acid (C18:1), linoleic acid (C18:2), linolenic acid (C18:3), and arachidonic acid (C20:4), C20:0, C22:0 and lethicin.

In certain embodiments of the invention the non-cationic lipid is selected from lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylet-hanolamine (POPE) and dioleoyl-phosphatidylethanolamine 4-(N-maleimidomethyl)-cyclohexane-1-carboxylate (DOPE-mal). Noncationic lipids also include sterols such as cholesterol, stigmasterol or stigmastanol. Cholesterol is known in the art. See U.S. Patent Application Publication Nos: U.S. 2006/0240554 and U.S. 2008/0020058. In certain embodiments, the LNP comprise a combination of a phospholipid and a sterol.

Where present, the non-cationic lipid typically comprises from about 0.1% to about 65%, about 2% to about 65%, about 10% to about 65%, or about 25% to about 65% expressed as mole percent of the total lipid present in the LNP. The LNPs described herein further include a polyethyleneglycol (PEG) lipid conjugate ("PEG-lipid") which may aid as a bilayer stabilizing component. The lipid component of the PEG lipid may be any non-cationic lipid described above including natural phospholipids, synthetic phospholipid derivatives, fatty acids, sterols, and combinations thereof. In certain embodiments of the invention, the PEG-lipids include, PEG coupled to dialkyloxypropyls (PEG-DAA) as described in, e.g., International Patent Application Publication No. WO 05/026372, PEG coupled to diacylglycerol (PEG-DAG) as described in, e.g., U.S. Patent Publication Nos. 20030077829 and 2005008689; PEG coupled to phosphatidylethanolamine (PE) (PEG-PE), or PEG conjugated to 1,2-Di-O-hexadecyl-sn-glyceride (PEG-DSG), or any mixture thereof (see, e.g., U.S. Pat. No. 5,885,613).

In one embodiment, the PEG-DAG conjugate is a dilaurylglycerol (C12)-PEG conjugate, a PEG dimyristylglycerol (C14) conjugate, a PEG-dipalmitoylglycerol (C16) conjugate, a PEG-dilaurylglycamide (C12) conjugate, a PEG-dimyristylglycamide (C14) conjugate, a PEG-dipalmitoylglycamide (C16) conjugate, or a PEG-disterylglycamide (C18). Those of skill in the art will readily appreciate that other diacylglycerols can be used in the PEG-DAG conjugates.

In certain embodiments, PEG-lipids include, but are not limited to, PEG-dimyristolglycerol (PEG-DMG), PEG-disteryl glycerol (PEG-DSG), PEG-dipalmetoleyl, PEG-dioleyl, PEG-distearyl, PEG-diacylglycamide (PEG-DAG), PEG-dialmitoyl phosphatidylethanolamine (PEG-DPPE), and PEG-1,2-dimyristyloxlpropyl-3-amine (PEG-c-DMA).

In certain embodiments, the PEG-lipid is PEG coupled to dimyristoylglycerol (PEG-DMG), e.g., as described in Abrams et al., 2010, Molecular Therapy 18(1):171, and U.S. Patent Application Publication Nos. US 2006/0240554 and US 2008/0020058, including for example, 2KPEG/PEG2000-DMG.

In certain embodiments, the PEG-lipid, such as a PEG-DAG, PEG-cholesterol, PEG-DMB, comprises a polyethylene glycol having an average molecular weight ranging of about 500 daltons to about 10,000 daltons, of about 750 daltons to about 5,000 daltons, of about 1,000 daltons to about 5,000 daltons, of about 1,500 daltons to about 3,000 daltons or of about 2,000 daltons. In certain embodiments, the PEG-lipid comprises PEG400, PEG1500, PEG2000 or PEG5000.

The acyl groups in any of the lipids described above are preferably acyl groups derived from fatty acids having about C10 to about C24 carbon chains. In one embodiment, the acyl group, is lauroyl, myristoyl palmitoyl, stearoyl or oleoyl.

The PEG-lipid conjugate typically comprises from about 0.1% to about 15%, from about 0.5% to about 20%, from about 1.5% to about 18%, from about 4% to about 15%, from about 5% to about 12%, from about 1% to about 4%, or about 2% expressed as a mole % of the total lipid present in said particle.

In certain embodiments of the invention, the LNPs comprise one or more cationic lipids, cholesterol and 1,2-Dimyristoyl-sn-glycerol methoxypolyethylene glycol (PEG-DMG).

In certain embodiments the invention, the LNPs comprise one or more cationic lipids, cholesterol, 1,2-Distearoyl-sn-glycero-3-phosphocholine (DSPC), and 1,2-Dimyristoyl-sn-glycerol methoxypolyethylene glycol (PEG-DMG).

In certain embodiments of the invention, the LNPs comprise lipid compounds assembled within the following molar ratios:
Cationic Lipid (20-99.8 mole %)
Non-cationic lipid (0.1-65 mole %) and
PEG-DMG (0.1-20 mole %).

In certain embodiments of the invention, the LNPs comprise lipid compounds assembled within the following molar ratios:
Cationic Lipid (30-70 mole %)
Non-cationic lipid (20-65 mole %) and
PEG-DMG (1-15 mole %).

In certain aspects of this embodiment, the non-cationic lipid is cholesterol. Exemplary LNPs may include cationic lipid/cholesterol/PEG-DMG at about the following molar ratios: 58/30/10.

In certain aspects of this embodiment, the non-cationic lipid is cholesterol and DSPC. Exemplary LNPs may include cationic lipid/cholesterol/DSPC/PEG-DMG at about the following molar ratios: 59/30/10/1; 58/30/10/2; 43/41/15/1; 42/41/15/2; 40/48/10/2; 39/41/19/1; 38/41/19/2; 34/41/24/1; and 33/41/24/2.

Preparation of LNPs

LNPs can be formed, for example, by a rapid precipitation process which entails micro-mixing the lipid components dissolved in ethanol with an aqueous solution using a confined volume mixing apparatus such as a confined volume T-mixer, a multi-inlet vortex mixer (MIVM), or a microfluidics mixer device as described below. The lipid solution contains one or more cationic lipids, one or more noncationic lipids (e.g., DSPC), PEG-DMG, and optionally cholesterol, at specific molar ratios in ethanol. The aqueous solution consists of a sodium citrate or sodium acetate buffered salt solution with pH in the range of 2-6, preferably 3.5-5.5. The two solutions are heated to a temperature in the range of 25° C.-45° C., preferably 30° C.-40° C., and then mixed in a confined volume mixer thereby instantly forming the LNP. When a confined volume T-mixer is used, the T-mixer has an internal diameter (ID) range from 0.25 to 1.0 mm. The alcohol and aqueous solutions are delivered to the inlet of the T-mixer using programmable syringe pumps, and with a total flow rate from 10-600 mL/minute. The alcohol and aqueous solutions are combined in the confined-volume mixer with a ratio in the range of 1:1 to 1:3 vol:vol, but targeting 1:1.1 to 1:2.3. The combination of ethanol volume fraction, reagent solution flow rates and t-mixer tubing ID utilized at this mixing stage has the effect of controlling the particle size of the LNPs between 30 and 300 nm. The resulting LNP suspension is twice diluted into higher pH buffers in the range of 6-8 in a sequential, multi-stage in-line mixing process. For the first dilution, the LNP suspension is mixed with a buffered solution at a higher pH (pH 6-7.5) with a mixing ratio in the range of 1:1 to 1:3 vol:vol, but targeting 1:2 vol:vol. This buffered solution is at a temperature in the range of 15-40° C., targeting 30-40° C. The resulting LNP suspension is further mixed with a buffered solution at a higher pH, e.g, 6-8 and with a mixing ratio in the range of 1:1 to 1:3 vol:vol, but targeting 1:2 vol:vol. This later buffered solution is at a temperature in the range of 15-40° C., targeting 16-25° C. The mixed LNPs are held from 30 minutes to 2 hours prior to an anion exchange filtration step. The temperature during incubation period is in the range of 15-40° C., targeting 30-40° C. After incubation, the LNP suspension is filtered through a 0.8 µm filter containing an anion exchange separation step. This process uses tubing IDs ranging from 1 mm ID to 5 mm ID and a flow rate from 10 to 2000 mL/minute. The LNPs are concentrated and diafiltered via an ultrafiltration process where the alcohol is removed and the buffer is exchanged for the final buffer solution such as phosphate buffered saline or a buffer system suitable for cryopreservation (for example containing sucrose, trehalose or combinations thereof). The ultrafiltration process uses a tangential flow filtration format (TFF). This process uses a membrane nominal molecular weight cutoff range from 30-500 KD, targeting 100 KD. The membrane format can be hollow fiber or flat sheet cassette. The TFF processes with the proper molecular weight cutoff retains the LNP in the retentate and the filtrate or permeate contains the alcohol and final buffer wastes. The TFF process is a multiple step process with an initial concentration to a lipid concentration of 20-30 mg/mL. Following concentration, the LNP suspension is diafiltered against the final buffer (for example, phosphate buffered saline (PBS) with pH 7-8, 10 mM Tris, 140 mM NaCl with pH 7-8, or 10 mM Tris, 70 mM NaCl, 5 wt % sucrose, with pH 7-8) for 5-20 volumes to remove the alcohol and perform buffer exchange. The material is then concentrated an additional 1-3 fold via ultrafiltration. The final steps of the LNP manufacturing process are to sterile filter the concentrated LNP solution into a suitable container under aseptic conditions. Sterile filtration is accomplished by passing the LNP solution through a pre-filter (Acropak 500 PES 0.45/0.8 µm capsule) and a bioburden reduction filter (Acropak 500 PES 0.2/0.8 µm capsule). Following filtration, the vialed LNP product is stored under suitable storage conditions (2° C.-8° C., or −20° C. if frozen formulation).

In some embodiments, the LNPs of the compositions provided herein have a mean geometric diameter that is less than 1000 nm. In some embodiments, the LNPs have mean geometric diameter that is greater than 50 nm but less than 500 nm. In some embodiments, the mean geometric diameter of a population of LNPs is about 60 nm, 75 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, or 475 nm. In some embodiments, the mean geometric diameter is between 100-400 nm, 100-300 nm, 100-250 nm, or 100-200 nm. In some embodiments, the mean geometric diameter is between 60-400 nm, 60-350 nm, 60-300 nm, 60-250 nm, or 60-200 nm. In some embodiments, the mean geometric diameter is between 75-250 nm. In some embodiments, 30%, 40%, 50%, 60%, 70%, 80%, 90%, or more of the LNPs of a population of LNPs have a diameter that is less than 500 nm. In some embodiments, 10%, 20%, 30%, 40%, 50%, 60%, 70%, 80%, 90%, or more of the LNPs of a population of LNPs have a diameter that is greater than 50 nm but less than 500 nm. In some embodiments, 10%, 20%, 30%, 40%, 50%, 60%, 70%, 80%, 90%, or more of the LNPs of a population of LNPs have a diameter of about 60 nm, 75 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, or 475 nm. In some embodiments, 10%, 20%, 30%, 40%, 50%, 60%, 70%, 80%, 90%, or more of the LNPs of a population of LNPs have a diameter that is between 100-400 nm, 100-300 nm, 100-250 nm, or 100-200 nm. In some embodiments, 10%, 20%, 30%, 40%, 50%, 60%, 70%, 80%, 90%, or more of the LNPs of a population of LNPs have a diameter that is between 60-400 nm, 60-350 nm, 60-300 nm, 60-250 nm, or 60-200 nm.

In a particular embodiment, the size of the LNPs ranges between about 1 and 1000 nm, preferably between about 10 and 500 nm, more preferably between about 100 to 300 nm, and preferably 100 nm.

Nucleic Acids/Polynucleotides

DNA of the present disclosure, in some embodiments, are codon optimized. Codon optimization methods are known in the art and may be used as provided herein. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.

In some embodiments, a codon optimized sequence shares less than 95% sequence identity, less than 90% sequence identity, less than 85% sequence identity, less than 80% sequence identity, or less than 75% sequence identity to a naturally-occurring or wild-type sequence.

In some embodiments, a codon-optimized sequence shares between 65% and 85% (e.g., between about 67% and about 85%, or between about 67% and about 80%) sequence identity to a naturally-occurring sequence or a wild-type sequence. In some embodiments, a codon-optimized sequence shares between 65% and 75%, or about 80% sequence identity to a naturally-occurring sequence or wild-type sequence.

Antigens/Antigenic Polypeptides

In some embodiments, an antigenic polypeptide includes gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. Polypeptides may also comprise single chain polypeptides or multichain polypeptides, such as antibodies or insulin, and may be associated or linked to each other. Most commonly, disulfide linkages are found in multichain polypeptides. The term "polypeptide" may also apply to amino acid polymers in which at least one amino acid residue is an artificial chemical analogue of a corresponding naturally-occurring amino acid.

The genome of Herpes Simplex Viruses (HSV-1 and HSV-2) contains about 85 open reading frames, such that HSV can generate at least 85 unique proteins. HSV glycoprotein C (gC) is a glycoprotein involved in the viral attachment to host cells. gC plays a role in host immune evasion (aka viral immunoevasion) by inhibiting the host complement cascade activation. An HSV vaccine ideally will induce gC specific antibodies that block gC/C3b binding. The HSV glycoprotein C constructs set forth herein as SEQ ID NO: 2-5 are variants with reduced binding to C3 protein and thus are potentially more immunogenic than wildtype gC antigen.

Glycoprotein B (gB) is a viral glycoprotein involved in the viral cell activity of HSV and is required for the fusion of the HSV envelope with the cellular membrane. An example of an HSV glycoprotein B is set forth in SEQ ID NO: 9. Also described herein in SEQ ID NO: 1 is an HSV glycoprotein B containing the extracellular domain of HSV-2 glycoprotein B fused with the transmembrane and cytoplasmic domains from vesicular stomatitis virus (VSV)-G protein. This construct is designed to improve the HSV gB neutralizing antibody response.

Glycoprotein D (gD) is an envelope glycoprotein that binds to cell surface receptors and/or is involved in cell attachment via poliovirus receptor-related protein and/or herpes virus entry mediator, facilitating virus entry. An example of an HSV glycoprotein D is set forth in SEQ ID NO: 7.

In epithelial cells, the heterodimer glycoprotein E (gE)/glycoprotein I (gI) is required for the cell-to-cell spread of the virus, by sorting nascent virions to cell junctions. An example of an HSV glycoprotein E is set forth in SEQ ID NO: 13. An example of an HSV glycoprotein I is set forth in SEQ ID NO: 15.

As used herein, the term "immunogenic fragment" as used herein refers to fragments which are capable of inducing an immune response to HSV. As a non-limiting example, a soluble ectodomain of glycoprotein E (SgE) is an immunogenic fragment of HSV glycoprotein E, a soluble ectodomain of glycoprotein D (SgD) is an immunogenic fragment of an HSV glycoprotein D, a soluble ectodomain of glycoprotein B (SgB) is an immunogenic fragment of an HSV glycoprotein B, a soluble ectodomain of glycoprotein C (SgC) is an immunogenic fragment of an HSV glycoprotein C, and a soluble ectodomain of glycoprotein I (SgI) is an immunogenic fragment of an HSV glycoprotein I. Non limiting examples of immunogenic fragments are set forth in SEQ ID NOs: 8, 10, 12, 14, and 16.

As used herein, the term "variant" is a molecule that differs in its amino acid sequence relative to a native sequence or a reference sequence. Amino acid sequence variants may possess substitutions, deletions, insertions; or a combination of any two or three of the foregoing, at certain positions within the amino acid sequence, as compared to a native sequence or a reference sequence. Ordinarily, variants possess at least 50% identity to a native sequence or a reference sequence. In some embodiments, variants share at least 80% identity or at least 90%, 91%, 92%, 93%, 94%, 95%, 96%, 97%, 98% or 99% identity with a native sequence or a reference sequence.

"Analogs" is meant to include polypeptide variants that differ by one or more amino acid alterations, for example, substitutions, additions or deletions of amino acid residues that still maintain one or more of the properties of the parent or starting polypeptide.

The present disclosure provides several types of compositions that are polynucleotide or polypeptide based, including variants and derivatives. These include, for example, substitutional, insertional, deletion and covalent variants and derivatives. The term "derivative" is synonymous with the term "variant" and generally refers to a molecule that has been modified and/or changed in any way relative to a reference molecule or a starting molecule.

As such, polynucleotides encoding peptides or polypeptides containing substitutions, insertions and/or additions, deletions and covalent modifications with respect to reference sequences, in particular the polypeptide sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility onto allow for biotinylation. Alternatively, amino acid residues located at the carboxy and amino terminal regions of the amino acid sequence of a peptide or protein may optionally be deleted providing for truncated sequences. Certain amino acids (e.g., C-terminal residues or N-terminal residues) alternatively may be deleted depending on the use of the sequence, as for example, expression of the sequence as part of a larger sequence that is soluble, or linked to a solid support.

"Substitutional variants" when referring to polypeptides are those that have at least one amino acid residue in a native or starting sequence removed and a different amino acid inserted in its place at the same position. Substitutions may be single, where only one amino acid in the molecule has been substituted, or they may be multiple, where two or more (e.g, 3, 4 or 5) amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

As used herein when referring to polypeptides the term "domain" refers to a motif of a polypeptide having one or more identifiable structural or functional characteristics or properties (e.g., binding capacity, serving as a site for protein-protein interactions).

As used herein when referring to polypeptides the terms "site" as it pertains to amino acid based embodiments is used synonymously with "amino acid residue" and "amino acid side chain." As used herein when referring to polynucleotides the terms "site" as it pertains to nucleotide based embodiments is used synonymously with "nucleotide." A site represents a position within a peptide or polypeptide or polynucleotide that may be modified, manipulated, altered, derivatized or varied within the polypeptide-based or polynucleotide-based molecules.

As used herein the terms "termini" or "terminus" when referring to polypeptides or polynucleotides refers to an extremity of a polypeptide or polynucleotide respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N- and C-termini. Alternatively, the termini of the polypeptides may be modified such that they begin or end, as the case may be, with a non-polypeptide based moiety such as an organic conjugate.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein having a length of 10, 20, 30, 40, 50, 60, 70, 80, 90, 100 or longer than 100 amino acids. In another example, any protein that includes a stretch of 20, 30, 40, 50, or 100 (contiguous) amino acids that are 40%, 50%, 60%, 70%, 80%, 90%, 95%, 96%, 97%, 98%, 99% or 100% identical to any of the sequences described herein can be utilized in accordance with the disclosure. In some embodiments, a polypeptide includes 2, 3, 4, 5, 6, 7, 8, 9, 10, or more mutations as shown in any of the sequences provided herein or referenced herein. In another example, any protein that includes a stretch of 20, 30, 40, 50, or 100 amino acids that are greater than 80%, 90%, 95%, or 100% identical to any of the sequences described herein, wherein the protein has a stretch of 5, 10, 15, 20, 25, or 30 amino acids that are less than 80%, 75%, 70%, 65% to 60% identical to any of the sequences described herein can be utilized in accordance with the disclosure.

Polypeptide or polynucleotide molecules of the present disclosure may share a certain degree of sequence similarity or identity with the reference molecules (e.g., reference polypeptides or reference polynucleotides), for example, with art-described molecules (e.g., engineered or designed molecules or wild-type molecules). The term "identity," as known in the art, refers to a relationship between the sequences of two or more polypeptides or polynucleotides, as determined by comparing the sequences. In the art, identity also means the degree of sequence relatedness between two sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. Identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al. (1997). "Gapped BLAST and PSI-BLAST: a new generation of protein database search programs," *Nucleic Acids Res.* 25:3389-3402). Another popular local alignment technique is based on the Smith-Waterman algorithm (Smith, T. F. & Waterman, M. S. (1981) "Identification of common molecular subsequences." *J. Mol. Biol.* 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." *J. Mol. Biol.* 48:443-453). More recently, a Fast Optimal Global Sequence Alignment Algorithm (FOGSAA) was developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g. between nucleic acid molecules (e.g. DNA molecules) and/or between polypeptide molecules. Polymeric molecules (e.g. nucleic acid molecules (e.g. DNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some, embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, 96%, 97%, 98% or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication. "Orthologs" are genes (or proteins) in different species that evolved from a common ancestral gene (or protein) by speciation. Typically, orthologs retain the same function in the course of evolution. "Paralogs" are genes (or proteins) related by duplication within a genome. Orthologs retain the same function in the course of evolution, whereas paralogs evolve new functions, even if these are related to the original one.

The term "identity" refers to the overall relatedness between polymeric molecules, for example, between polynucleotide molecules (e.g. DNA molecules) and/or between polypeptide molecules. Calculation of the percent identity of two polynucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleic acid sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, N.J., 1994; and Sequence Analysis Primer, Gribskov, M. and Devereux, J., eds., M Stockton Press, New York, 1991; each of which is incorporated herein by reference. For example, the percent identity between two nucleic acid sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleic acid sequences can, alternatively, be determined using the GAP program in the GCG software package using an NWSgap-dna.CMP matrix. Methods commonly employed to determine percent identity between sequences include, but are not limited to those disclosed in Carillo, H, and Lipman, D., SIAM *J Applied Math,* 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12, 387 (1984)), BLASTP, BLASTN, and FASTA Altschul, S. F. et al, *J. Molec. Biol.,* 215, 403 (1990)).

Signal Peptides

In some embodiments, antigenic polypeptides comprise a signal peptide. Signal peptides, comprising the N-terminal 15-60 amino acids of proteins, are typically needed for the translocation across the membrane on the secretory pathway and, thus, universally control the entry of most proteins both in eukaryotes and prokaryotes to the secretory pathway. ER processing produces mature proteins, wherein the signal peptide is cleaved from precursor proteins, typically by a ER-resident signal peptidase of the host cell, or they remain uncleaved and function as a membrane anchor. As referred herein, "mature amino acid sequence" does not contain the signal peptide sequence.

Methods of Treatment

Provided herein are compositions (e.g., pharmaceutical compositions), methods, kits and reagents for prevention and/or treatment of HSV virus in humans and other mammals. HSV virus vaccines can be used as therapeutic or prophylactic agents. They may be used in medicine to prevent and/or treat infectious disease. In exemplary aspects, the HSV virus vaccines of the present disclosure are used to provide prophylactic protection from HSV virus. Prophylactic protection from HSV virus can be achieved following administration of an HSV virus vaccine of the present disclosure. Vaccines can be administered once, twice, three times, four times or more. It is possible, although less desirable, to administer the vaccine to an infected individual to achieve a therapeutic response. Dosing may need to be adjusted accordingly.

In some embodiments, the HSV virus vaccines of the present disclosure can be used as a method of preventing an HSV virus infection in a subject, the method comprising administering to said subject at least one HSV virus vaccine as provided herein. In some embodiments, the HSV virus vaccines of the present disclosure can be used as a method of treating an HSV virus infection in a subject, the method comprising administering to said subject at least one HSV virus vaccine as provided herein. In some embodiments, the HSV virus vaccines of the present disclosure can be used as a method of reducing an incidence of HSV virus infection in a subject, the method comprising administering to said subject at least one HSV virus vaccine as provided herein. In some embodiments, the HSV virus vaccines of the present disclosure can be used as a method of inhibiting spread of HSV virus from a first subject infected with HSV virus to a second subject not infected with HSV virus, the method comprising administering to at least one of said first subject and said second subject at least one HSV virus vaccine as provided herein.

A method of eliciting an immune response in a subject against an HSV virus is provided in aspects of the invention. The method involves administering to the subject an HSV virus vaccine described herein, thereby inducing in the subject an immune response specific to HSV virus antigenic polypeptide or an immunogenic fragment thereof.

A prophylactically effective dose is a therapeutically effective dose that prevents infection with the virus at a clinically acceptable level. In some embodiments the therapeutically effective dose is a dose listed in a package insert for the vaccine.

Therapeutic and Prophylactic Compositions

Provided herein are compositions (e.g., pharmaceutical compositions), methods, kits and reagents for prevention, treatment or diagnosis of HSV in humans and other mammals, for example. HSV virus vaccines can be used as therapeutic or prophylactic agents. They may be used in medicine to prevent and/or treat infectious disease. In some embodiments, the respiratory vaccines of the present disclosure are used for the priming of immune effector cells, for example, to activate peripheral blood mononuclear cells (PBMCs) ex vivo, which are then infused (re-infused) into a subject. In some embodiments, vaccines in accordance with the present disclosure may be used for treatment of HSV.

HSV virus vaccines may be administered prophylactically or therapeutically as part of an active immunization scheme to healthy individuals or early in infection during the incubation phase or during active infection after onset of symptoms. In some embodiments, the amount of vaccine of the present disclosure provided to a cell, a tissue or a subject may be an amount effective for immune prophylaxis.

HSV virus vaccines may be administrated with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The tune of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In some embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, HSV virus vaccines may be administered intramuscularly or intradermally. In some embodiments, HSV virus vaccines are administered intramuscularly.

HSV virus vaccines may be utilized in various settings depending on the prevalence of the infection or the degree or level of unmet medical need. Vaccines have superior properties in that they produce much larger antibody titers and produce responses early than commercially available anti-viral agents/compositions.

Provided herein are pharmaceutical compositions including HSV virus vaccines optionally in combination with one or more pharmaceutically acceptable excipients.

HSV virus vaccines may be formulated or administered alone or in conjunction with one or more other components. For instance, HSV virus vaccines (vaccine compositions) may comprise other components including, but not limited to, adjuvants.

In some embodiments, HSV vaccines do not include an adjuvant (they are adjuvant free).

Aluminium has long been shown to stimulate the immune response against co-administered antigens, primarily by stimulating a TH2 response. It is preferred that the aluminium adjuvant of the compositions provided herein is not in the form of an aluminium precipitate. Aluminium-precipitated vaccines may increase the immune response to a target antigen, but have been shown to be highly heterogeneous preparations and have had inconsistent results {see Lindblad E. B. Immunology and Cell Biology 82: 497-505 (2004)). Aluminium-adsorbed vaccines, in contrast, can be preformed in a standardized manner, which is an essential characteristic of vaccine preparations for administration into humans. Moreover, it is thought that physical adsorption of a desired antigen onto the aluminium adjuvant has an important role in adjuvant function, perhaps in part by allowing a slower clearing from the injection site or by allowing a more efficient uptake of antigen by antigen presenting cells.

The aluminium adjuvant of the present invention may be in the form of aluminium hydroxide ($Al(OH)_3$), aluminium phosphate ($AlPO_4$), aluminium hydroxyphosphate, amorphous aluminium hydroxyphosphate sulfate (AAHS) or so-called "alum" ($KAl(SO4)$-$12H2O$) {see Klein et al, Analysis of aluminium hydroxyphosphate vaccine adjuvants by (27) Al MAS NMR., J. Pharm. Sci. 89(3): 311-21 (2000)). In exemplary embodiments of the invention provided herein, the aluminium adjuvant is aluminium hydroxyphosphate or AAHS. The ratio of phosphate to aluminium in the aluminium adjuvant can range from 0 to 1.3. In preferred embodiments of this aspect of the invention, the phosphate to aluminium ratio is within the range of 0.1 to 0.70. In particularly preferred embodiments, the phosphate to aluminium ratio is within the range of 0.2 to 0.50. APA is an aqueous suspension of aluminum hydroxyphosphate. APA is manufactured by blending aluminum chloride and sodium phosphate in a 1:1 volumetric ratio to precipitate aluminum hydroxyphosphate. After the blending process, the material is size-reduced with a high-shear mixer to achieve a target aggregate particle size in the range of 2-8 μm. The product is then diafiltered against physiological saline and steam sterilized. See, e.g., International Patent Application Publication No. WO2013/078102.

In some embodiments of the invention, the aluminium adjuvant is in the form of AAHS (referred to interchangeably herein as Merck aluminium adjuvant (MAA)). MAA carries zero charge at neutral pH, while AlOH carries a net positive charge and $AlPO_4$ typically carries a net negative charge at neutral pH.

One of skill in the art will be able to determine an optimal dosage of aluminium adjuvant that is both safe and effective at increasing the immune response to the targeted antigenic polypeptides. For a discussion of the safety profile of aluminium, as well as amounts of aluminium included in FDA-licensed vaccines, see Baylor et al., Vaccine 20: S18-S23 (2002). Generally, an effective and safe dose of aluminium adjuvant varies from 150 to 600 µg/dose (300 to 1200 µg/mL concentration). In specific embodiments of the formulations and compositions of the present invention, there is between 200 and 300 µg aluminium adjuvant per dose of vaccine. In alternative embodiments of the formulations and compositions of the present invention, there is between 300 and 500 µg aluminium adjuvant per dose of vaccine.

HSV virus vaccines may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety). In some embodiments, HSV virus vaccines are administered to humans, human patients or subjects.

Formulations of the HSV vaccine compositions described herein may be prepared by any method known or hereafter developed in the art of pharmacology. In general, such preparatory methods include the step of bringing the active ingredient (e.g., polypeptide or polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

Modes of Vaccine Administration

HSV vaccines may be administered by any route which results in a therapeutically effective outcome. These include, but are not limited, to intradermal, intramuscular, intranasal and/or subcutaneous administration. The present disclosure provides methods comprising administering vaccines to a subject in need thereof. The exact amount required will vary from subject to subject, depending on the species, age, and general condition of the subject, the severity of the disease, the particular composition, its mode of administration, its mode of activity, and the like. HSV vaccines compositions are typically formulated in dosage unit form for ease of administration and uniformity of dosage. It will be understood, however, that the total daily usage of vaccine compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, HSV vaccines compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see, e.g., the range of unit doses described in International Publication No WO2013078199, the contents of which are herein incorporated by reference in their entirety). The desired dosage may be delivered three times a day, two times a day, once a day, every other day, every third day, every week, every two weeks, every three weeks, every four weeks, every 2 months, every three months, every 6 months, etc. In some embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, HSV vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, HSV vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

An HSV vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, intranasal and subcutaneous).

HSV Virus Vaccine Formulations and Methods of Use

Some aspects of the present disclosure provide formulations of the HSV vaccine, wherein the vaccine is formulated in an effective amount to produce an antigen specific immune response in a subject (e.g., production of antibodies specific to an HSV antigenic polypeptide). "An effective amount" is a dose of a vaccine effective to produce an antigen-specific immune response. Also provided herein are methods of inducing an antigen-specific immune response in a subject.

In some embodiments, the antigen-specific immune response is characterized by measuring an anti-HSV antigenic polypeptide antibody titer produced in a subject administered an HSV vaccine as provided herein. An antibody titer is a measurement of the amount of antibodies within a subject, for example, antibodies that are specific to a particular antigen (e.g., an HSV antigenic polypeptide) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the HSV vaccine.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1

Preparation of New Antigenic Constructs for HSV Glycoprotein B and HSV Glycoprotein C HSV-2 Glycoprotein B Chimeric Construct Glycoprotein B (gB) is one of the most conserved glycoproteins encoded by herpes viruses, with homologues in each of the subfamilies, such as HSV, EBV, and CMV. During virus entry, gB functions as a fusogen to mediate the merger of the viral envelope and cellular membrane. gB is also a major target of neutralizing antibodies and CD8+ T cells in naturally infected humans. Given its universal role in virus entry and naturally acquired immunity, gB has been one of the major focuses of vaccine development for CMV and HSV.

Based on the crystal structure, the recombinantly expressed gB ectodomain likely adopts the postfusion conformation. The prefusion form of gB has not yet been characterized, but may contain more potent neutralizing epitopes that are not present in the postfusion form. A stable and native prefusion gB might therefore enhance the neutralizing antibody responses against virus infection. Recently, it was reported that full extracellular domain of CMV gB fused with the transmembrane and cytoplasmic domains from vesicular stomatitis virus (VSV)-G protein (CMC gB-G) potentially preserved the conformation as prefusion form. Kirchmeir et al., Clin Vaccine Immunol, February 2014 21(2): 174-180. When expressed on the enveloped virus like particles, such chimeric vaccine could elicit neutralizing antibody titers about 10 times higher than those induced by the recombinant postfusion gB. Described herein is the generation of an HSV gB-G construct to improve the HSV gB neutralizing antibody response.

The extracellular domain of HSV-2 glycoprotein B is fused with the transmembrane and cytoplasmic domains from vesicular stomatitis virus (VSV)-G protein, and the sequence of such construct is set forth in SEQ ID NO:1 in Table 1. The HSV-2 glycoprotein corresponds to amino acids 1-768 of SEQ ID NO:1 and the cytoplasmic domain from VSV-G protein corresponds to amino acids 769-812 of SEQ ID NO: 1.

HSV-2 Glycoprotein C Construct

HSV gC protein binds human plasma protein C3 and C3B as a mechanism of immune evasion by blocking complement activation. An HSV vaccine would ideally induce gC specific antibodies that block gC/C3b binding. The wildtype HSV glycoprotein C is "masked" by C3 proteins in plasma and weakly immunogenic. The variant gC antigens described in Table 2 have reduced binding to C3 protein and are thus potentially more immunogenic than wildtype gC antigen.

TABLE 1

Antigenic Polypeptide Sequences

| Name | Sequence | SEQ ID NO: |
|---|---|---|
| MRK_HSV-2 gB-G1 VSV-G protein amino acid sequence is underlined | MRCTGGLVCALVVGALVAAVASAAPAAPRASGGVAAT VAANGGPASQPPPVPSPATTKARKRKTKKPPKRPEATPP PDANATVAAGHATLRAHLREIKVENADAQFYVCPPPIG ATVVQFEQPRRCPTRPEGQNYTEGIAVVEKENIAPYKEK ATMYYKDVTVSQVWFGHRYSQFMGIFEDRAPVPFEEVI DKINAKGVCRSTAKYVRNNMETTAFFIRDDHETDMELK PAKVATRTSRGWHTTDLKYNPSRVEAFHRYGTTVNCIV EEVDARSVYPYDEFVLATGDFVYMSPFYGYREGSHTEH TSYAADRFKQVDGFYARDLTTKARATSPTTRNLLTTPK FTVAWDWVPKRPAVCTMTKWQEVDEMLRAEYGGSFR FSSDAISTTFTTNLTQYSLSRVDLGDCIGRDAREAIDRMF ARKYNATHIKVGQPQYYLATGGFLIAYQPLESNTLAEL YVREYMREQDRXPRNATPAPLREAPSANASVERIKTTSS IEFARLQFTYNHIQRHVNDMLGRIAVAWCELQNHELTL WNEARKLNPNAIASATVGRRVSARMLGDVMAVSTCVP VAPDNVIVQNSMRVSSRPGTCYSRPLVSFRYEDQGPLIE GQLGENNELRLTRDALEPCTVGHRRYFIFGGGYVYFEE YAYSHQLSRADVTTVSTFIDLNITMLEDHEFVPLEVYTR HEIKDSGLLDYTEVQRRNQLHDLRFADIDTVIRADANA | 1 |

TABLE 1-continued

Antigenic Polypeptide Sequences

| Name | Sequence | SEQ ID NO: |
|---|---|---|
| | AMFAGLCAFFEGMGDLGRAVGKVVMGVVGGVVSAVS GVSSFMSNP<u>FFFIIGLIIGLFLVLRVGIHLCIKLKHTKKRQI YTDIEMNRLGK</u> | |
| MRK_HSV-2 gC_DX_ W368A | MALGRVGLAVGLWGLLWVGVVVVLANASPGRTITVGP RGNASNAAPSASPRNASAPRTTPTPPQPRKATKSKASTA KPAPPPKTGPPKTSSEPVRCNRHDPLARYGSRVQIRCRFP NSTRTESRLQIWRYATATDAEIGTAPSLEEVMVNSAPP GGQLVYDSAPNRTDPHVIWAEGAGPGASPRLYSVVGPL GRQRLIIEELTLETQGMYYWVWGRTDRPSAYGTWVRV RVFRPPSLTIHPHAVLEGQPFKATCTAATYYPGNRAEFV WFEDGRRVFDPAQIHTQTQENPDGFSTVSTVTSAAVGG QGPPRTFTCQLTWHRDSVSFSRRNASGTASVLPRPTITM EFTGDHAVCTAGCVPEGVTFAAFLGDDSSPAEKVAVAS QTSCGRPGTATIRSTLPVSYEQTEYICRLAGYPDGIPVLE HHGSHQPPPRDPTERQVIRAVEGAGIGVAVLVAVVLAG TAVVYLTHASSVRYRRLR | 2 |
| MRK_HSV-2 gC_DX D323A | MALGRVGLAVGLWGLLWVGVVVVLANASPGRTITVGP RGNASNAAPSASPRNASAPRTTPTPPQPRKATKSKASTA KPAPPPKTGPPKTSSEPVRCNRHDPLARYGSRVQIRCRFP NSTRTESRLQIWRYATATDAEIGTAPSLEEVMVNSAPP GGQLVYDSAPNRTDPHVIWAEGAGPGASPRLYSVVGPL GRQRLIIEELTLETQGMYYWVWGRTDRPSAYGTWVRV RVFRPPSLTIHPHAVLEGQPFKATCTAATYYPGNRAEFV WFEDGRRVFDPAQIHTQTQEN TABLE 2-continued DNA Sequences

| Name | Sequence | SEQ ID NO: |
|------|----------|------------|
|  | CCAGCCAGCCAGCCTCCTCCAGTGCCTAGCCCAGCTA CCACCAAGGCCAGAAAGAGAAAGACCAAGAAGCCTC CTAAGCGTCCTGAGGCCACCCCACCACCAGACGCCAA TGCGACCGTGGCCGCAGGCCACGCCACCCTGAGAGC CCACCTGAGAGAGATCAAGGTGGAGAACGCCGACGC CCAGTTCTACGTGTGTCCTCCGCCTACCGGTGCAACA GTGGTGCAGTTCGAGCAGCCTAGAAGATGCCCTACCC GACCAGAGGGTCAGAACTACACCGAGGGCATCGCCG TGGTGTTCAAGGAGAACATCGCCCCTTACAAGTTCAA GGCCACCATGTACTACAAGGACGTGACCGTGAGCCA GGTGTGGTTCGGCCACAGATACAGCCAGTTCATGGGC ATCTTCGAGGACAGAGCCCCAGTACCTTTCGAGGAGG TGATCGACAAGATCAACGCCAAGGGCGTGTGCAGAA GCACCGCCAAGTACGTGAGAAACAACATGGAGACAA CCGCCTTCCACAGAGACGACCACGAAACCGACATGG AGCTGAAGCCTGCCAAGGTGGCCACCAGAACCAGCA GAGGCTGGCACACCACCGACCTGAAGTACAACCCTA GCAGAGTGGAGGCGTTCCACCGATACGGCACCACCG TGAACTGCATCGTGGAAGAGGTCGACGCCAGAAGCG TGTACCCTTACGACGAGTTCGTGCTGGCCACCGGCGA CTTCGTGTACATGAGCCCTTTCTACGGCTACAGAGAG GGCAGCCACACCGAGCACACCAGCTACGCCGCCGAC AGATTCAAGCAAGTTGACGGCTTCTACGCCCGGGATC TTACAACTAAGGCTAGAGCAACTAGCCCTACTACTAG GAACCTGCTTACTACCCCTAAGTTCACAGTGGCCTGG GACTGGGTGCCTAAGAGGCCTGCCGTGTGCACCATGA CCAAGTGGCAGGAAGTCGACGAGATGCTTCGCGCAG AGTACGGCGGCAGCTTCAGATTCAGCAGCGACGCCAT CAGCACCACCTTCACCACAAACCTGACCCAGTACAGC CTGTCTCGAGTCGACCTGGGCGATTGTATCGGCAGAG ATGCAAGAGAGGCCATCGACAGAATGTTCGCCAGGA AGTATAACGCTACCCACATTAAGGTGGGTCAGCCACA GTACTACCTAGCAACTGGCGGCTTCCTGATCGCCTAC CAGCCTCTGCTGAGCAACACCCTGGCCGAGCTCTACG TACGGAATATATGAGAGAGCAGGACAGAAAGCCAA GGAACGCAACTCCTGCCCCTCTGAGGGAAGCTCCTAG CGCCAACGCCAGCGTGGAGAGAATCAAGACCACCAG CAGCATCGAATTCGCCCGGCTGCAGTTCACCTACAAC CACATCCAGAGACACGTGAACGACATGCTGGGCAGA ATCGCTGTGGCTTGGTGCGAGCTGCAGAACCACGAGC TGACCCTGTGGAACGAGGCGCGCAAGCTGAACCCTA ACGCCATCGCCTCCGCCACCGTGGGTAGGAGAGTGA GCGCCAGAATGCTCGGAGATGTGATGGCCGTGAGCA CCTGCGTGCCTGTGGCCCCTGACAACGTGATCGTGCA GAACAGCATGCGGGTTAGCAGCAGACCTGGCACCTG CTACTCACGACCTCTGGTGTCATTCAGATACGAGGAC CAGGGCCCTCTGATCGAAGGACAGTTGGGCGAGAAC AACGAGCTTAGACTGACCCGTGATGCGCTGGAGCCTT GTACCGTGGGACATCGAAGATACTTCATCTTCGGAGG TGGATACGTGTATTTCGAAGAATACGCCTACAGTCAT CAGCTTTCTCGAGCCGATGTGACTACCGTGAGTACCT TCATCGATCTTAACATCACCATGCTGGAGGATCATGA ATTCGTGCCTCTGGAGGTGTACACCAGACACGAGATT AAGGATTCTGGACTTCTGGACTATACCGAAGTGCAGA GAAGAAACCAGCTGCACGACCTGAGATTCGCCGACA TCGACACCGTGATCAGGGCAGATGCTAACGCAGCCAT GTTCGCAGGCCTGTGCGCCTTCTTCGAAGGCATGGGC GATCTAGGACGGGCCGTTGGAAAGGTGGTGATGGGC GTGGTCGGCGGAGTTGTAAGTGCTGTGTCTGGCGTTT CCTCATTCATGAGCAACCCTTTCTTCTTCATCATCGGC CTGATCATAGGATTGTTCCTGGTCCTCCGAGTGGGCA TCCACCTGTGCATCAAGTTGAAGCATACTAAGAAGAG ACAGATTTATACGACATTGAGATGAACAGACTGGG CAAGTGATAATAGGCTGGAGCCTCGGTGGCCATGCTT CTTGCCCCTTGGGCCTCCCCCCAGCCCCTCCTCCCCTT CCTGCACCCGTACCCCCGTGGTCTTTGAATAAAGTCT GAGTGGGCGGC |  |

Example 2

Combination Vaccines

A study was conducted in mice to confirm that combinations of mRNA antigens can elicit appropriate immune responses against each vaccine component. Each vaccine antigen was administered at an equivalent dose (2 ug), so that the effect of additional antigens were not confounded by dose differences. Doses of LNPs were increased with additional mRNA antigens, aiming to maintain the same lipid to nucleic acid ratio in each group.

| Group | Number | Vaccine (MC3 formulation) | Dose/mouse (µg) |
|---|---|---|---|
| 1 | 15 | gD | 2 |
| 1 | 15 | gD + gC | 4 (2 of each antigen) |
| 3 | 15 | gD + gC + gE | 6 (2 of each antigen) |
| 4 | 15 | gD + gC + gE + gI | 8 (2 of each antigen) |
| 5 | 15 | gD + gC + gE + gI + gB | 10 (2 of each antigen) |
| 6 | 15 | gD + gC + gE + gB | 8 (2 of each antigen) |
| 7 | 15 | MC3 | N/A |

Female Balb/c (CRL) mice (6-8 weeks old; N=15 mice per group) were administered with 10 µg or 2 µg per mouse mRNA vaccines. The mRNA vaccines were generated and formulated in MC3 lipid nanoparticles. The animals were immunized on day 0 and day 21 of the experiment. On day 35, blood was drawn from each animal and tested by ELISA for binding to HSV antigens. On day 40, four animals from each group were sacrificed for spleen collection.

ELISA assays: Immulon® 2HB microtiter plates (NUNC) were coated with 50 µl HSV antigens per well at a concentration of 2.0 µg/ml in PBS and incubated at 4° C. overnight. The plates were then washed and blocked for 1 h with PBST containing 3% milk at room temperature. Test samples were serially diluted 4-fold in blocking buffer starting at 1:100 dilution, transferred to the antigen coated plates, and incubated for 2 h at room temperature. Following three washes with PBST, goat anti-mouse IgG-HRP diluted to 1:2000 in blocking buffer was added to the plates, and incubated for an additional 1 h at room temperature. Plates were washed again and developed with SuperBlu Turbo TMB in the dark. The reaction was stopped after 5 minutes and absorbance was read at 450 nm on a VersaMax ELISA microplate reader. Titers are reported as the reciprocal of the last dilution that is 2 fold greater than the background.

Cytokine Production Assay: Three weeks post final immunization, four animals from each group were sacrificed for spleen collection. Spleens from each group were pooled and processed to isolate splenocytes. One million splenocytes/well were incubated with 2 µg/ml of specific peptide pools (15mer overlapping by 11, custom order JPT Peptide Solns, Germany) for HSV-2 gC, HSV-2 gD, HSV-2 gE, and HSV-2 gB in the presence of brefeldin A, anti-mouse CD28 and CD49b antibodies. As a negative control, a sample for each was set up with a matched volume of DMSO and costimulatory antibodies. Five hours post incubation at 37° C., splenocytes were incubated with mouse FC block, surface stained with viability dye, anti-mouse-CD3, CD4 and CD8 followed by permeabilization and intracellular staining for anti-mouse IFNγ, TNFα, IL-2. Fixed samples were then run on FACS LSRII flow cytometer (BD Biosciences) and data were analyzed using FlowJo software (Treestar Inc.). All peptide stimulated responses were reported after subtraction of the unstimulated controls.

Results: Vaccines containing multiple antigens are immunogenic. As shown in FIG. 1, immunogenicity of individual mRNA antigens is maintained in a multivalent vaccine. For example, the anti-gD ELISA antibody binding titers are the same whether gD is administered alone, or in combination with 2, 3, 4, or 5 mRNA antigens. One exception is gE, where binding antibodies are measurable in those groups also receiving gI antigen. When gI was coadministered with gE, the ELISA binding levels of gE were increased, confirming that a vaccine combination utilizing gE mRNA will also require gI as a component; however, the anti-gE responses may also be achieved by using SgE expressing mRNA without gI.

Figure 2:
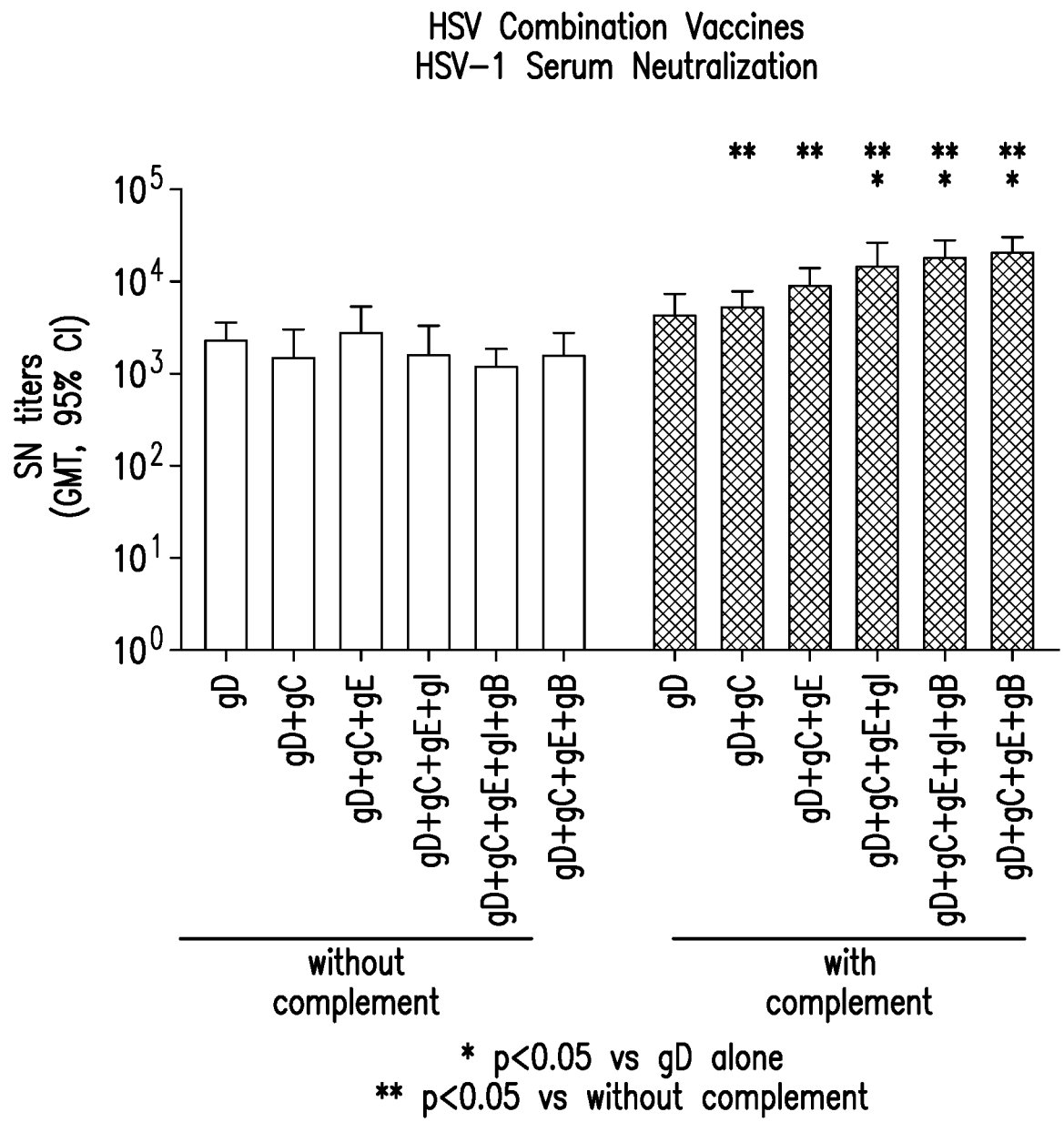
FIG. 2 is a graph showing the results of HSV-1 serum neutralization titers for various HSV combination vaccines, with and without complement.
Figure 3:
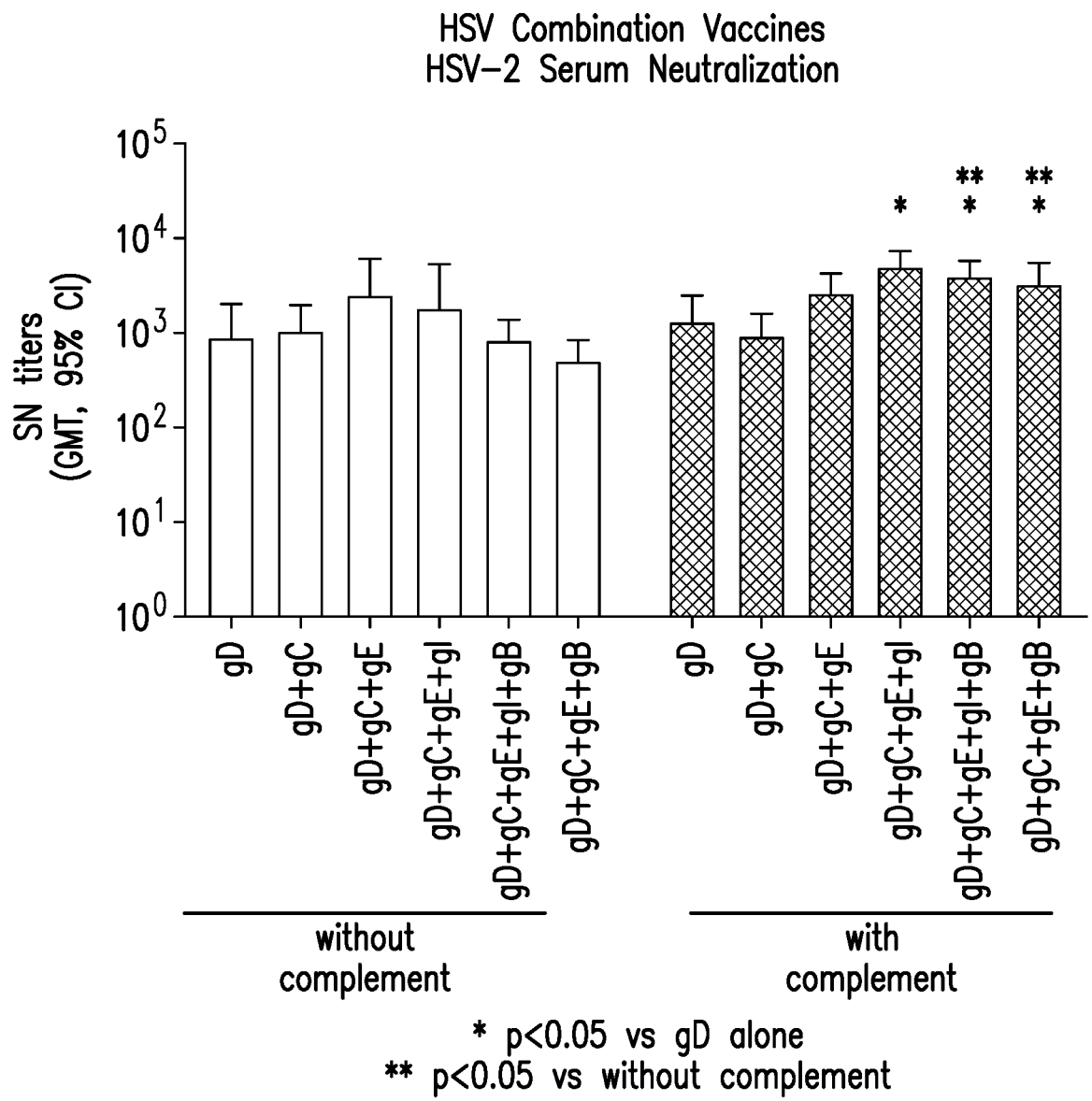
FIG. 3 is a graph showing the results of HSV-2 serum neutralization titers for various HSV combination vaccines, with and without complement.

Functional immune responses were also induced in multivalent vaccines. As shown in FIG. 2, SNA titers against HSV-1 were found to be unaffected by the inclusion of additional antigens. For multivalent vaccines, the neutralizing titers against HSV-1 were significantly increased by the addition of complement, an indication that inclusion of gC and gE may allow for more effective viral neutralization with complement involvement. With added complement quadrivalent and pentavalent vaccine combinations were 4-fold better than vaccination with gD alone. As shown in FIG. 3, SNA titers against HSV-2 were elicited by all mRNA vaccine tested. Similar to HSV-1, there was no observed difference in titers when the assay was run without complement. However, the addition of complement significantly, improved (>10 fold) SNA titers in vaccines containing gB antigen. Elicited SNA titers in this study were similar to those measured in guinea pigs following 3 doses of a subunit vaccine (gD+gC/CpG and alum) (Awasthi 2011, J. Virol. 2011 October; 85(20): 10472-86) demonstrating that these mRNA vaccine candidates would provide efficacy in the guinea pig challenge model.

As observed in earlier studies, inclusion of gC mRNA antigen elicits antibody responses capable of blocking the binding of C3B complement by gC. In this study, all groups receiving gC antigen produced C3B/gC blocking antibodies, although the group receiving the pentavalent combination had significantly lower competition titers than the group receiving gD+gC. This decrease in antibodies capable of blocking C3B/gC does not appear to affect either antigen binding ELISA titers or SNA titers against HSV-1 or HSV-2.

Cellular immune responses for certain antigens are also slightly lower in combination vaccines (when compared to previous results of antigen being administered alone). CD4+ T cell responses are lower for gE and gB antigens, but are unaffected for gD and gC; while CD8+ T cell responses are statistically lower for gC and gB antigens, but gE specific CD8+ cells are unaffected (gD specific CD8+ T cells are near background levels).

Example 3

Antigen Combinations and Neutralizing Antibodies

To identify the most immunogenic HSV-2 mRNA antigen combinations and to determine the durability of immune responses against mRNA antigens, eight mRNA combinations were further evaluated in the guinea pig model. Guinea pigs (6 each per group) were administered intramuscularly with 20 µg HSV2 mRNA each at week 0, 4, and 8. The animals were bled two weeks after each vaccination.

| Group | Number | Vaccine | Dose/guinea pig (µg) |
|---|---|---|---|
| 1 | 6 | gD (LNP 1) | 20 |
| 2 | 6 | gD (MC3 LNP) | 20 |
| 3 | 6 | gD + gC (MC3 LNP) | 40 (20 + 20) |
| 4 | 6 | gD + gC + gE + gI (MC3 LNP) | 80 (20 + 20 + 20 + 20) |
| 5 | 6 | gD + gC + gE + gI + gB (MC3 LNP) | 100 (20 + 20 + 20 + 20 + 20) |

-continued

| Group | Number | Vaccine | Dose/guinea pig (µg) |
|---|---|---|---|
| 6 | 6 | gD + gC + gE + gB (MC3 LNP) | 80(20 + 20 + 20 + 20) |
| 7 | 6 | gD + gB (MC3 LNP) | 40(20 + 20) |
| 8 | 6 | gD + gC + SgE + gB (MC3 LNP) | 80(20 + 20 + 20 + 20) |
| 9 | 6 | gD + gC + gB (MC3 LNP) | 60(20 + 20 + 20) |
| 10 | 6 | gD + gE + gI + gB (MC3 LNP) | 80(20 + 20 + 20 + 20) |
| 11 | 6 | MC3 LNP control | N/A |

The EC10 ELISA titers for all antigens reach to around $10^6$ at day 42 except for gI which reaches $10^6$ at around day 70. ELISA titers for all antigens start to go down at day 112. There is very little difference in ELISA titers by group.

Figure 4:
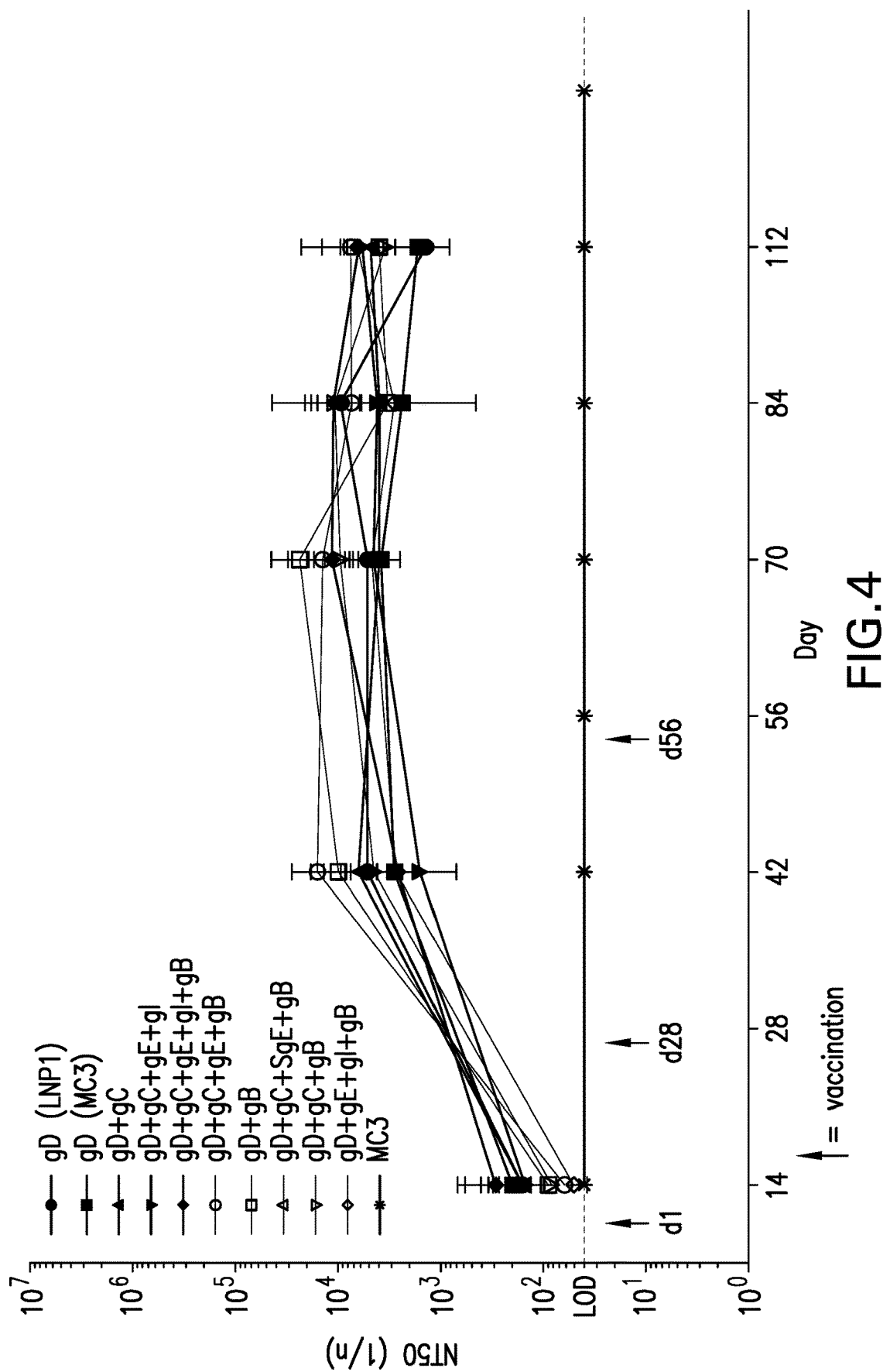
FIG. 4 is a graph showing NT50 titer (neutralizing), without complement, as a function of time.

NT50 titers (Neutralizing) peak at day 42 with gD, gD+gC, gD+gC+gE+gI groups reaching around $10^4$ and the multiple antigen groups containing gB reaching near $10^6$ with complement. As shown in FIGS. 4 and 5, neutralizing titers are maintained through day 70 and decline slightly on day 84 and day 112.

Figure 6A:
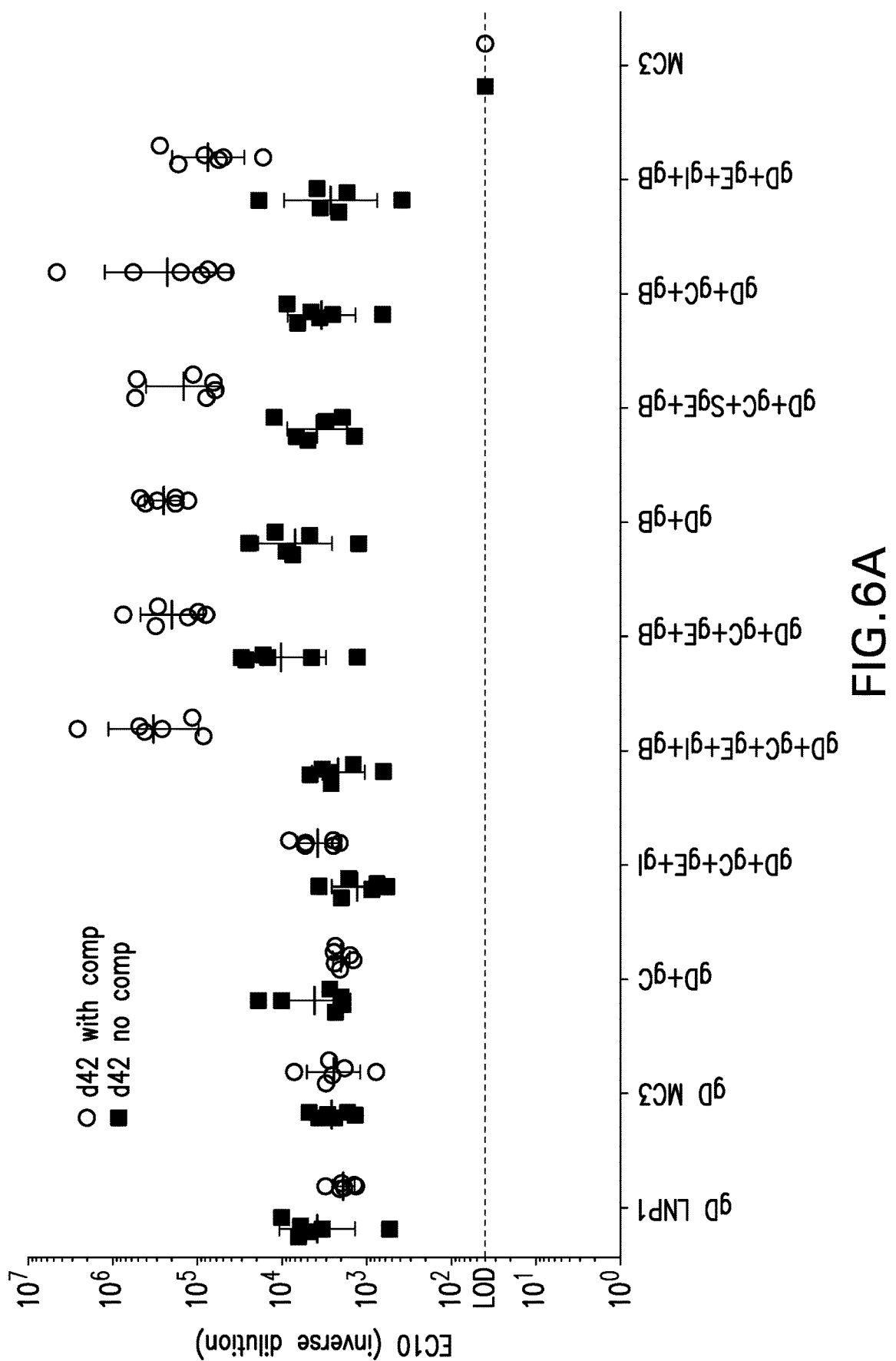
FIG. 6a is a graph showing HSV-2MS serum neutralization titers, with and without complement, for various antigen formulations at day 42.
Figure 6B:
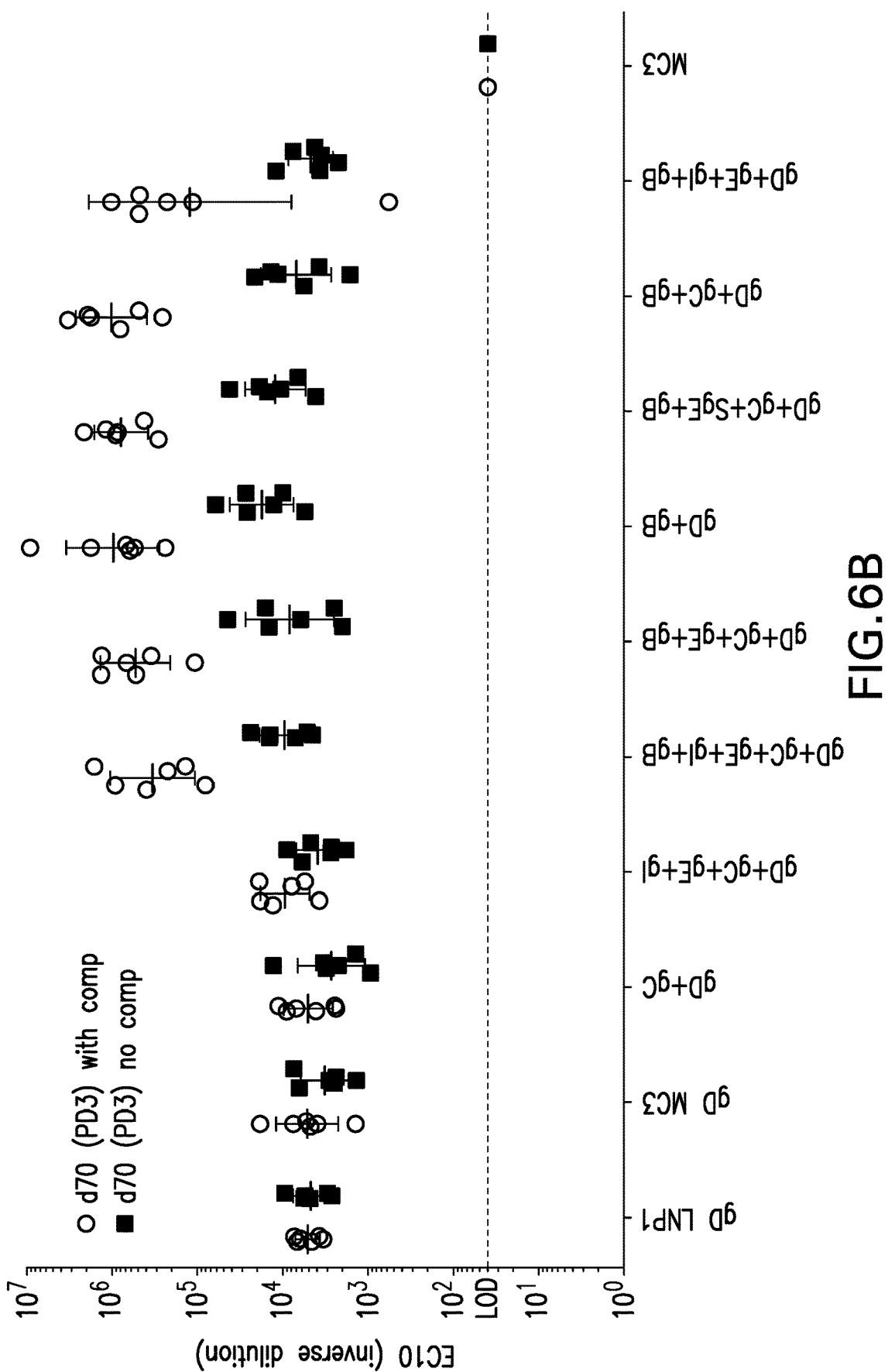
FIG. 6b is a graph showing HSV-2MS serum neutralization titers, with and without complement, for various antigen formulations at day 70.

As shown in FIGS. 6a and 6b, the neutralizing data demonstrate that in the presence of compliment, all groups containing gB antigen exhibit a 100 fold increase in neutralizing titers.

Example 4

C3 Binding Studies

Figure 7:
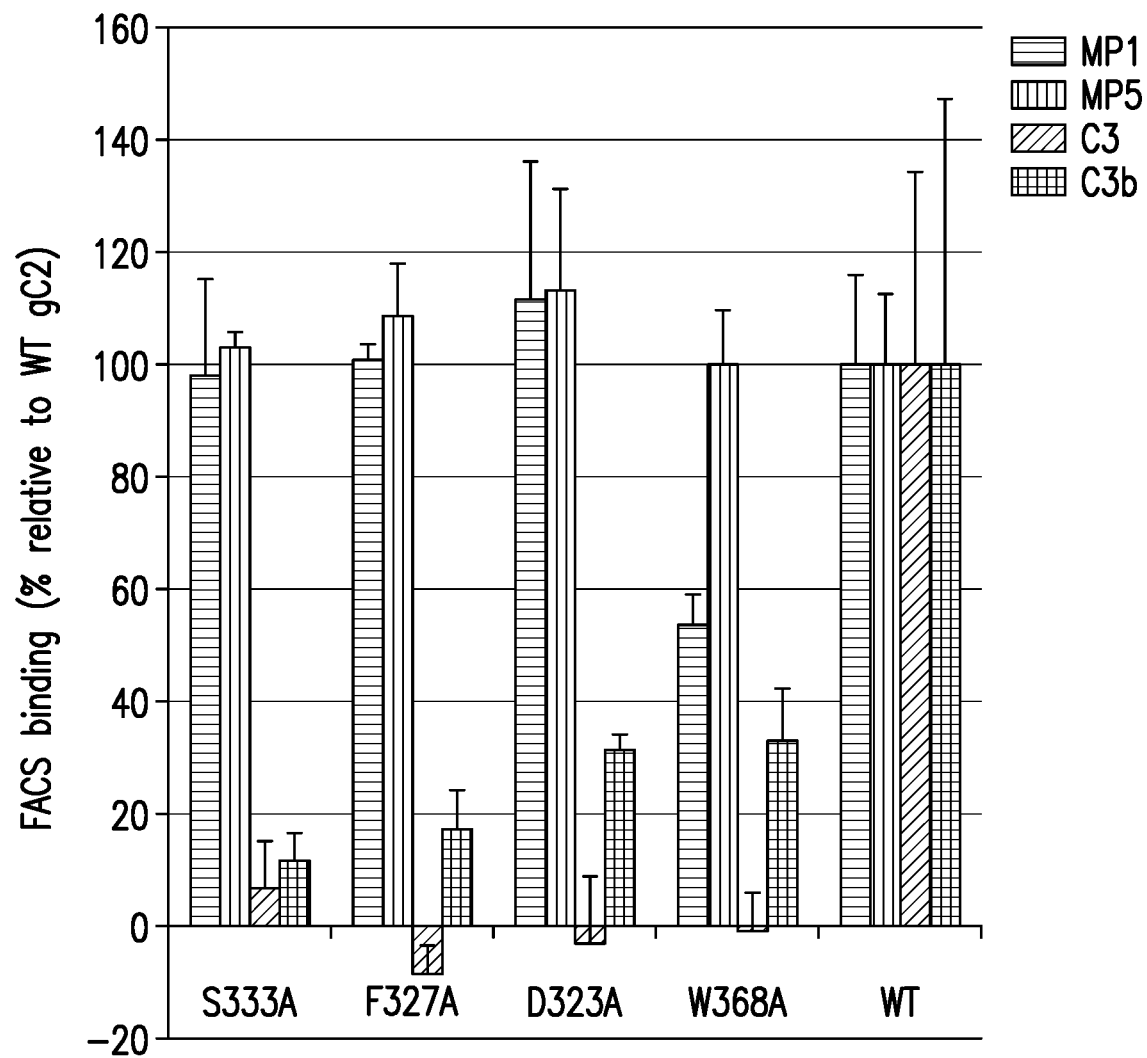

The HSV glycoprotein C constructs set forth herein as SEQ ID NO: 2-5 are variants which exhibit reduced binding to C3. Wild type and mutant gC2 constructs expressed on BEK293T cells were tested for reactivity with two anti-gC2 mAbs and purified human complement proteins C3 and C3b. The binding activity was measured on an Intellicyt high-throughput flow cytometer. As shown in FIG. 7, mutation of four individual residues to Alanine reduced gC2 binding to C3 and C3b (dotted and checked bars), but not to the two anti-gC2 mAbs (hatched bars). Error bars represent standard deviation from four replicate data points.

Example 5

Evaluation of Efficacy of HSV2 mRNA Vaccines Against Genital HSV-2 Challenge in the Guinea Pig Model Naïve female Hartley guinea pigs (Charles River Laboratories) were treated with vehicle and vaccine at the following time points (day 0, day 28, and day 56) as follows:

| Group | Number | Vaccine | Dose/guinea pig (µg) |
|---|---|---|---|
| 1 | 18 | Vehicle (LNP) | 20 |
| 2 | 12 | gD2 protein + MPL/alum | 20 |
| 3 | 12 | gD + gB | 40 (20 + 20) |
| 4 | 12 | gD + gB + gC | 60 (20 + 20 + 20) |
| 5 | 12 | gD + gB + gC + SgE | 8- (20 + 20 + 20 + 20) |

Group 3 corresponds to a positive vaccine control. Groups 3-4 correspond to mRNA LNP formulation containing the specified antigen formulated in a LNP. Genital lesions were scored on days 78-118. At day 118, the animals were sacrificed and the dorsal root ganglia and spleen were collected. The animals were challenged with $5 \times 10^5$ PFU HSV-2 strain MS on day 77. HSV-2 neutralization assays, with and without complement, were performed on sera from groups 2-5 and from 6 animals in group 1.

HSV Neutralization Titers: Serum bleeds were conducted at days −4, 14, 42, and 70. The neutralizing antibody titers were determined on vero cells with or without complement as described below.

Vero cells were seeded at $3 \times 10^5$ ($3 \times 10^4$ cells/well) into 96 well flat-bottomed plates and incubated overnight to achieve confluent monolayers. Four-fold serial dilutions of the heat inactivated serum samples were prepared in 199 medium starting at 1:40 dilution. The complement dependent neutralization activities were measure by diluting heat inactivated sera in a 199 medium containing 5% baby rabbit complement. Fifty microliter of diluted serum was added to 96-well plates and mixed with 200 PFU of HSV2 MS strain in 100 µl total volume. The virus/antibody mixture was incubated for 1 h at 37° C. Following incubation, fifty microliter of the virus/antibody mixture was added to Vero cells. The plates were incubated for 24 h at 37° C. The cells were then fixed with 3.7% formaldehyde in PBS for 10 min, and washed twice with 100 ul/well of 0.1% Triton X-100/PBS, and four times with 150 ul/well of PBS/0.1% Tween-20. HSV2 infected cells were then immunostained with rabbit anti-HSV polyclonal antibody. Briefly, a HSV2 polyclonal antibody was diluted at 1:400 in blocking buffer, and then added to the test plates with fixed cells and incubated for 1 h at room temperature. After washing, Alexafluor 488 anti-rabbit IgG diluted at 1:400 was added and incubated for 1 h. The plates were washed again and the signal was read on Perkin Elmer Envision at 488 nm. To determine neutralizing titers (NT50), data is transformed to % neutralization using the below equation.

% Neutralization=(1−((sample reading−cell control)/ (sample reading−cell control))*100

Vaginal Lesions: Guinea pigs (n=12 or 18/group) were scored daily for 19 days after vaginal challenge with HSV-2 strain MS ($5 \times 10^5$PFU) using the follow vaginal lesion scoring system: 0=no disease, 0.5=redness OR swelling of <50% of the vagina, 1=redness OR swelling of ≥50% of the vagina, 1.5=redness AND swelling of ≥50% of the vagina, 2=1 to 5 non-coalesced (coalesced=individual lesions that have combined together to form a larger lesion) lesions on the external genital skin, 2.5=1 to 5. lesions including at least 1 coalesced lesion on the external genital skin, 3=≥6 non-coalesced lesions on the external genital skin, 3.5=≥6 lesions including at least 1 coalesced lesion on the external genital skin, 4=any number of ulcerated (ulcerated=a lesion where the top white portion has been lost leaving an open lesion) or necrotic (necrotic=a lesion where the top white portion has been lost leaving a blackened area on the lesion) lesions on the external genital skin. Daily scores for each group (n=5) were averaged and plotted as mean±standard error.

Vaginal Swabs: Vaginal swabs were collected two days post vaginal challenge and placed into 1.5 mL tubes with 0.6 mL of DMEM with 5% FBS and gentamicin and frozen until further processing. Viral load was determined by Plaque assay and PCR. For the plaque assay 24 well tissue culture plates were seeded with Vero cells at $5 \times 10^5$ cells per well and grown overnight at 37° C., 5% $CO_2$. The following day, vaginal swab samples were thawed in a 37° C. water bath, vortexed for 10 seconds and then serially diluted 1:10 in Serum-free William's E medium, containing 2 mM L-glutamine and 50 µg/ml Neomycin (SFMM). Samples were tested at Neat, 1:10 and 1:100 dilutions. Media was aspirated from 24 well plates and cells were washed with 1 ml of SFMM. SFMM wash was aspirated and 75 µl of sample was added to wells and plates were incubated at 37° C., 5% $CO_2$ for 1 hour with manual rocking every 15 minutes. After 1 hour incubation, samples were aspirated from wells and 1 ml of 0.75% Methyl Cellulose (4000 cPs) in William's E medium containing 1.6% FBS, 2 mM L-glutamine and 50 µg/ml Neomycin, was added to each well. Plates were incubated at 37° C., 5% $CO_2$ for 3 days. Methyl cellulose was aspirated, cells were washed with 1 ml PBS and cells were fixed and stained with 5% glutaric dialdehyde containing crystal violet for 1 hour. Stain was then aspirated, cells were washed with 1 ml $H_2O$, plates were allowed to air dry and plaques were counted. For PCR, DNA was extracted using Qiagen blood and tissue DNA extraction kit. A 112 bp HSV2 gB DNA fragment was quantified by real time PCR.

Tissue Analysis: Dorsal root ganglia ("DRG") from each surviving guinea pig were collected 48 days post HSV-2 challenge. The DRG DNA was extracted using Qiagen blood and tissue DNA extraction kit.

Results:

HSV Neutralization Titers

Figures 8A, 8B:
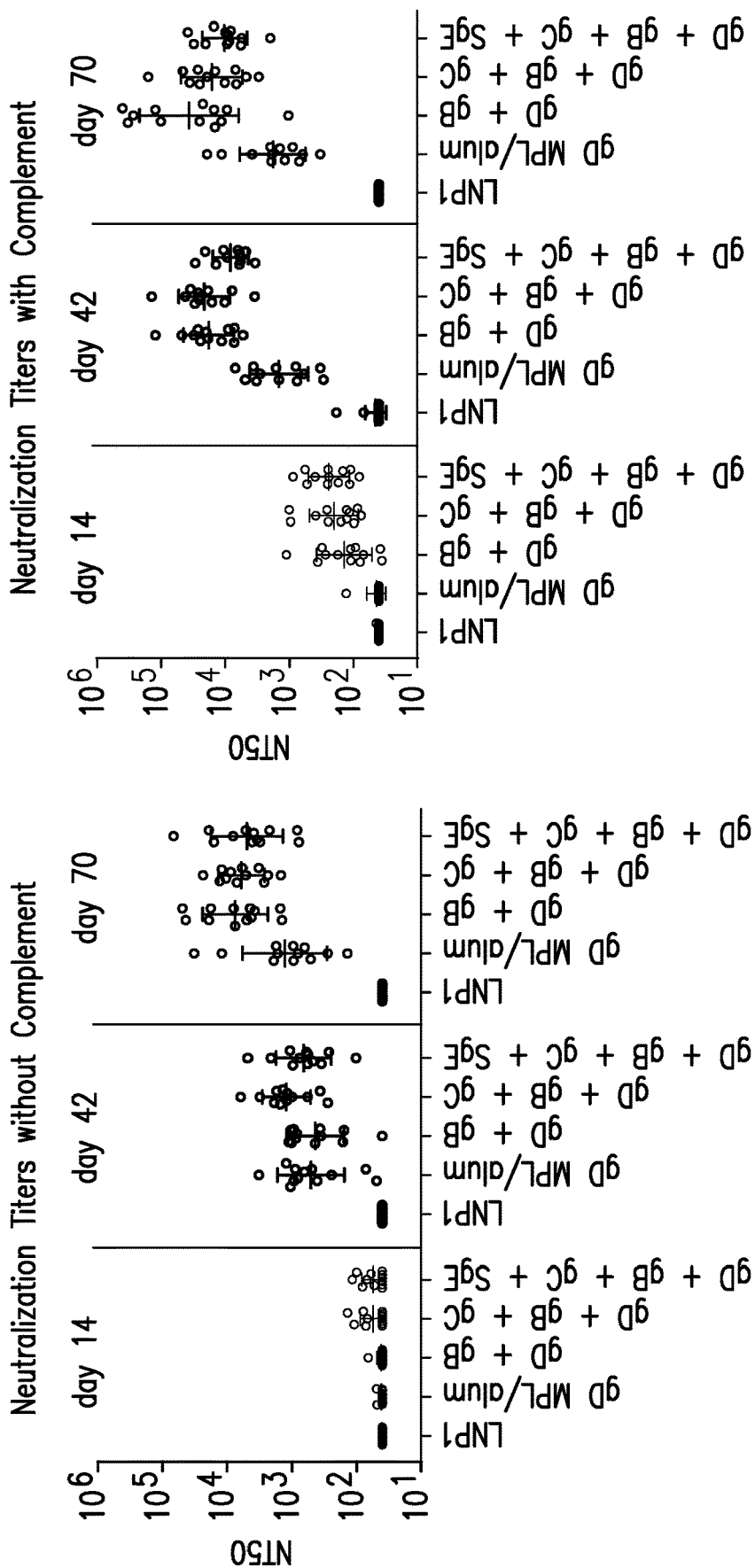

FIGS. 8a and 8b shows the serum neutralization titers with and without complement, respectively. As can be seen from FIGS. 8a and 8b, the mRNA vaccines (gD+gB, gD+gB+gC, gD+gB+gC+SgE) induced higher neutralizing antibody responses than the gD protein vaccine with or without complement.

Vaginal Lesions

Figure 9:
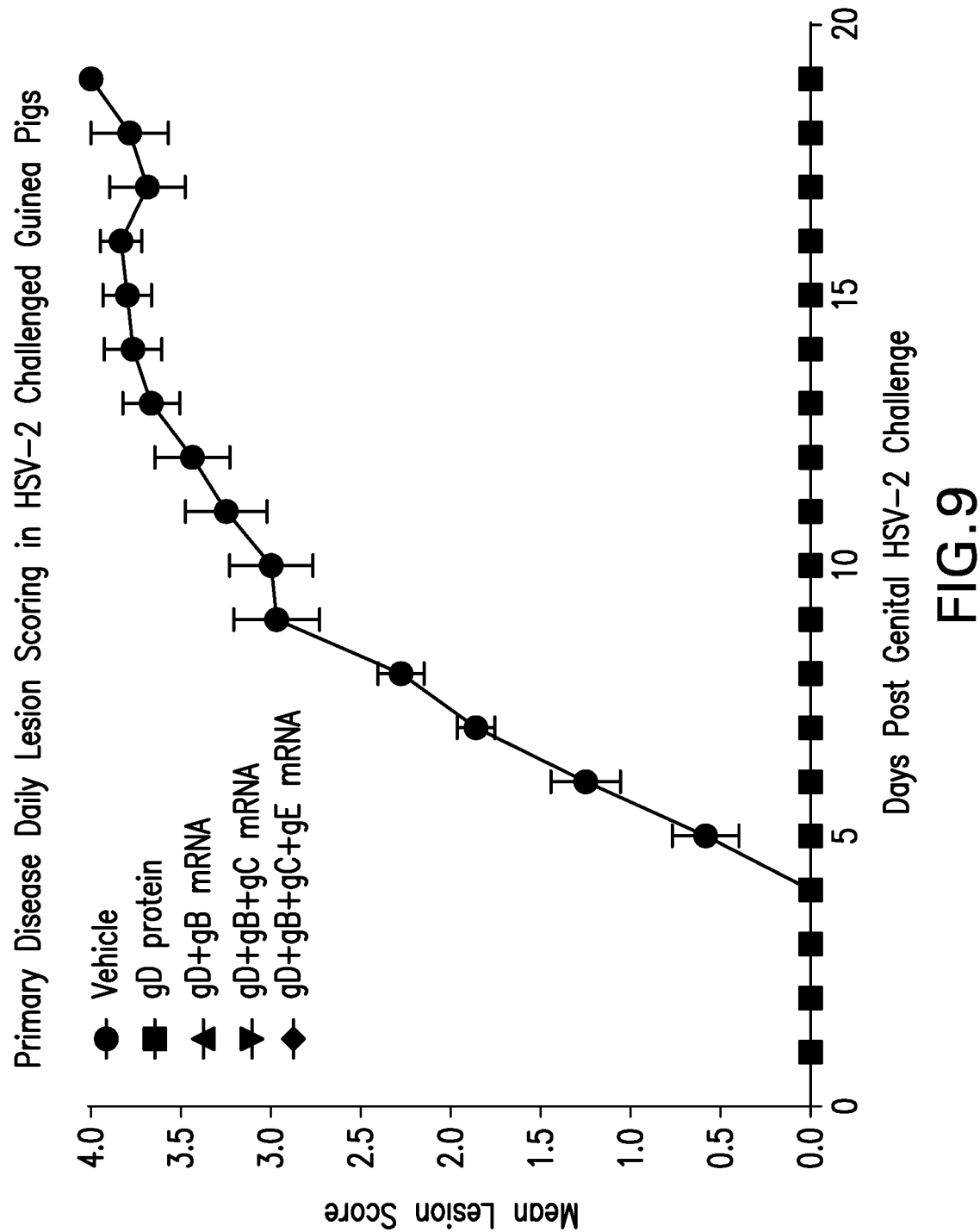

As shown in FIG. 9, no vaginal disease was detected in the vaccinated animals throughout the study, whereas all animals in group 1 (vehicle) developed severe disease 5 days post vaginal challenge. 13 of 18 animals in group 1 died after the challenge.

Vaginal Swabs

Figure 10A:
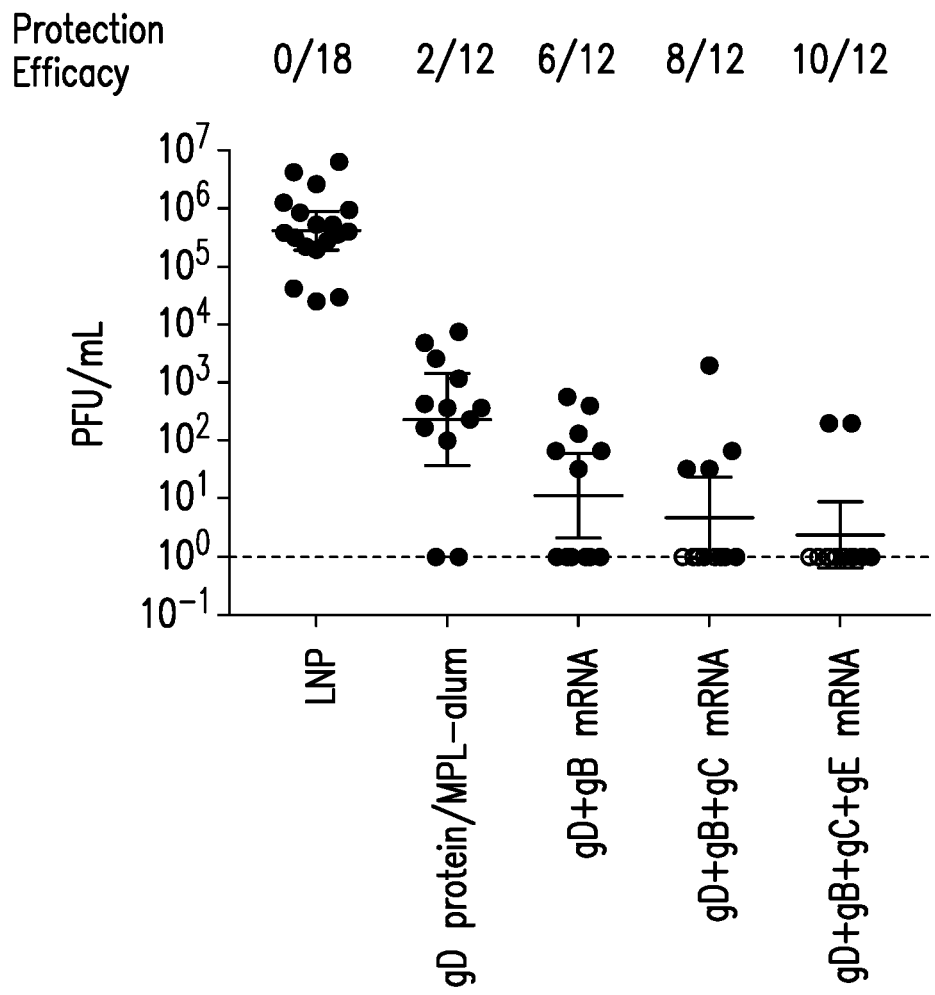
Figure 10B:
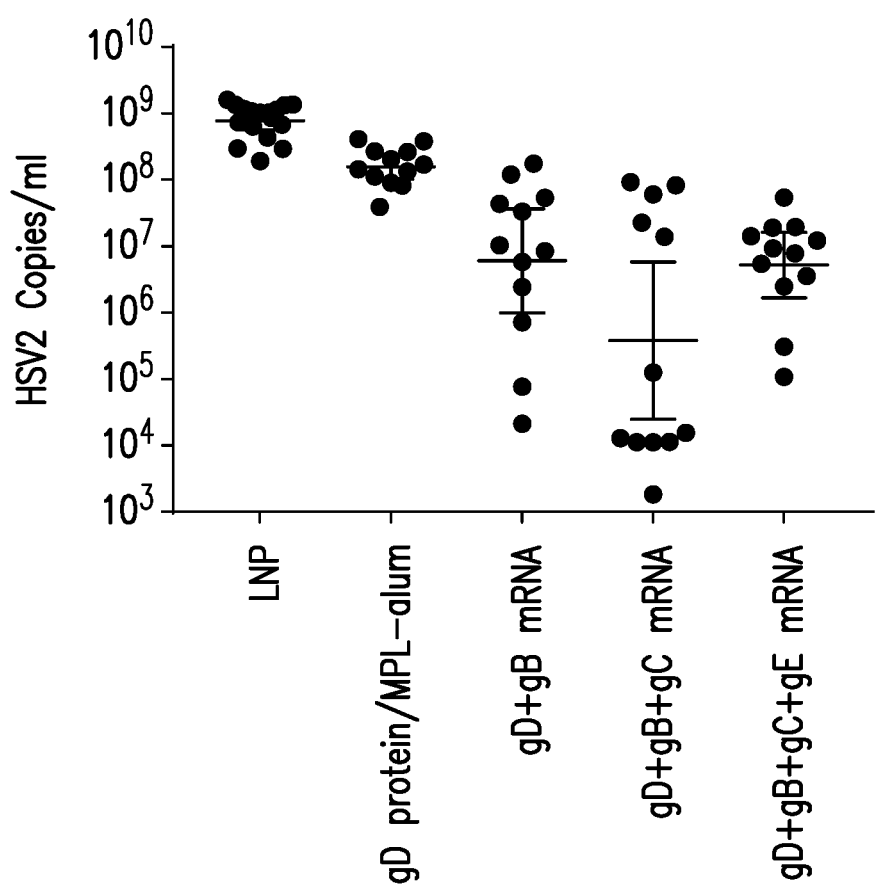

FIGS. 10a and 10b show the vaginal viral load at day 2 post HSV-2 challenge as determined by the plaque assay (FIG. 10a) and PCT (FIG. 10b). As shown in FIGS. 10a and 10b, vaccination with gD protein reduced the virus shedding by $10^3$-$10^4$ folds, but only two animals in the group 2 were completely protected against primary infection. In the mRNA vaccine groups, the virus shedding was further reduced by another log, and fewer animals shed the virus. 6, 8 or 10 out of 12 animals in groups 3-5 were completely protected against primary infection.

Tissue Analysis

Figure 11:
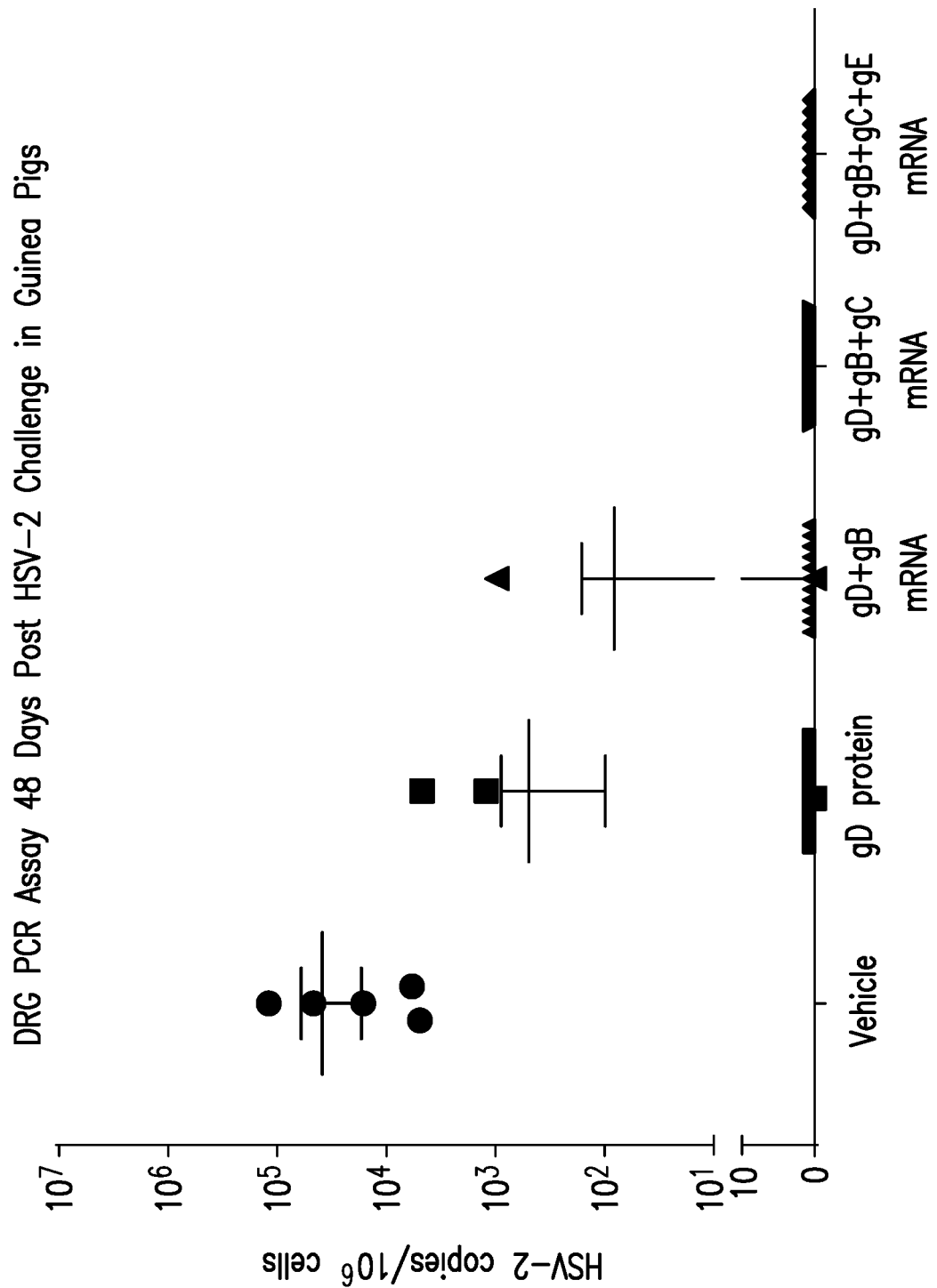

FIG. 11 sets forth the number of HSV-2 copies in the dorsal root ganglia as determined by PCR. As shown in FIG. 11, all 5 control animals survived the HSV2 challenge had high levels of latent viral DNA in the ganglia. In the gD protein vaccine group, latent DNA was detected in 2 animals, and DNA copy numbers were significantly lower than in the control group. In contrast, none of the animals received gD+gB+gC or gD+gB+gC+SgE were latently infected.

Example 6

Mutated HSV-c Constructs and Neutralizing Antibodies

Female Balb/C (CRL) mice (16/group) were administered 2 ug per mouse of vehicle (LNP only) of mRNA vaccine formulated in an LNP.

| Group (N = 16 per group) | Vaccine (mRNA formulated in LNP) (2 µg per mouse) | Dose per mouse (Delivered by IM injection) | Challenge Dose (delivered intravaginally) |
|---|---|---|---|
| 1 | LNP only (Vehicle) | 2 µg | $9 \times 10^4$ pfu of HSV-2 |
| 2 | gC2 | 2 µg | $9 \times 10^4$ pfu of HSV-2 |
| 3 | gC2 D323 | 2 µg | $9 \times 10^4$ pfu of HSV-2 |
| 4 | gC2 F327A | 2 µg | $9 \times 10^4$ pfu of HSV-2 |
| 5 | gC2 S333A | 2 µg | $9 \times 10^4$ pfu of HSV-2 |
| 6 | gC2 W368A | 2 µg | $9 \times 10^4$ pfu of HSV-2 |

Animals were immunized on day 0 and day 21. On day 35 blood was drawn from each animal to determine (i) HSV-2 neutralizing antibody titers and (ii) c3b binding competition antibodies titers. In addition, on day 35 four animals from each group were sacrificed for spleen collection. On day 42 animals were injected subcutaneously with 2 mg medoxyprogesterone (Depo-Provera®; Pfizer, Inc., New York, N.Y.) on DAY 49 animals were challenged with 9×10^4 PFU of HSV2 MS strain. On days 50-63 HSV2 disease progression was monitored daily. Vaginal swabs were collected on days 51 and 54 (i.e., day 2 and day 4 post HSV-2 challenge). Animals were sacrificed and dorsal root ganglia were collected on day 63 (i.e., 2 weeks post HSV-2 challenge).

HSV-2 Neutralization Titers were determined as described above in Example 5.

C3b binding competition antibodies induced by gC2 wild type and c3b binding mutants c3b binding competition antibodies titers were determined by Alphalisa assay.

Testing samples were serially diluted first, then 10 ul per well of rgC2 (Merck) conjugated with acceptor beads (Perkin Elmer) at concentration of 150 ug/ml were added in ½ area of 96 well assay plate (Perkin Elmer). Then 10 ul per well of series diluted samples were transferred into the assay plate that containing the rgC2 with acceptor beads, followed by a 30 minute incubation. 10 ul of biotinylated (Perkin Elmer) human C3b (Complement Technology) at concentration of 15 nm were added and followed by a 60 minute incubation. Streptavidin donor beads (Perkin Elmer) at concentration of 20 ug/ml were added with final 30 minute incubation before reading the plate. Plate was read at EnSight machine (Perkin Elmer). Data were analyzed in GraphPad Prism and % inhibition (Y-axis) was plotted against the log transformed serum dilution and the IC50 were calculated using 4-parameter curve-fitting. The competition titers are expressed as IC50, the serum dilution at which gC2/C3b binding is inhibited by 50%

Cytokine production assay was performed substantially as described in Example 2.

Vaginal Swabs were collected at day 2 and 4 post HSV-2 challenge and _placed into 1.5 mL tubes with 0.6 mL of DMEM with 5% FBS and gentamicin and frozen until further processing. The viral load of the vaginal swabs was determined by plaque assay as described in Example 5.

Figure 12:
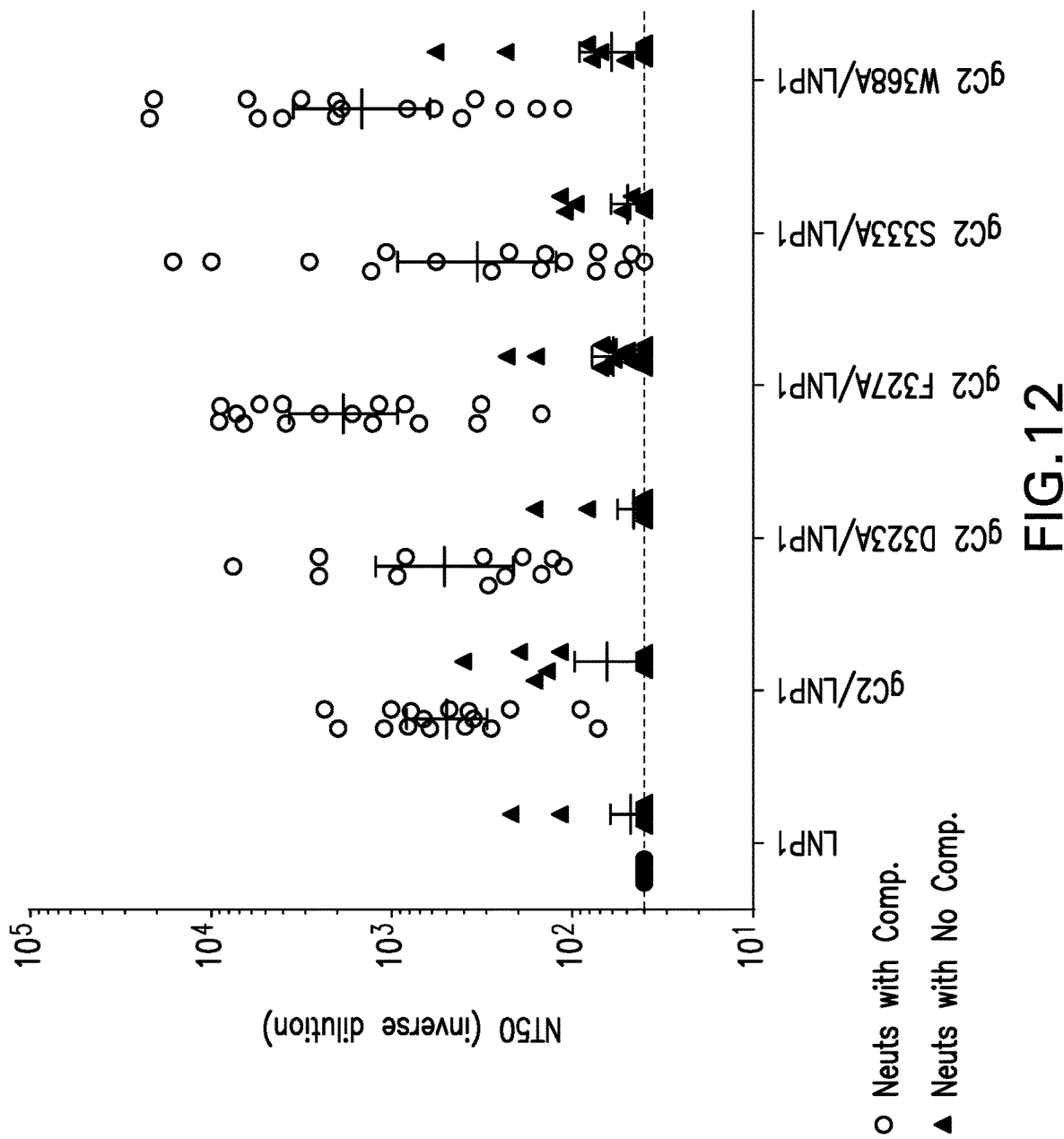
Figure 13:
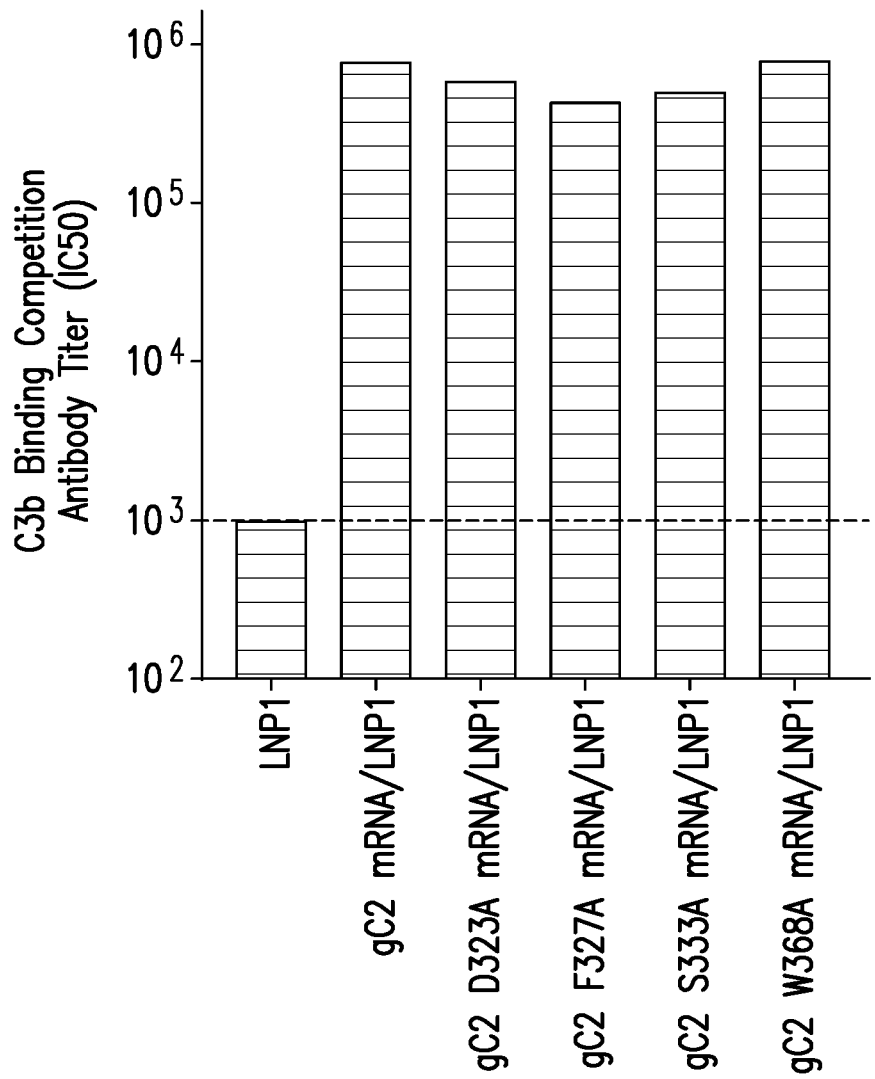
Figure 14B:
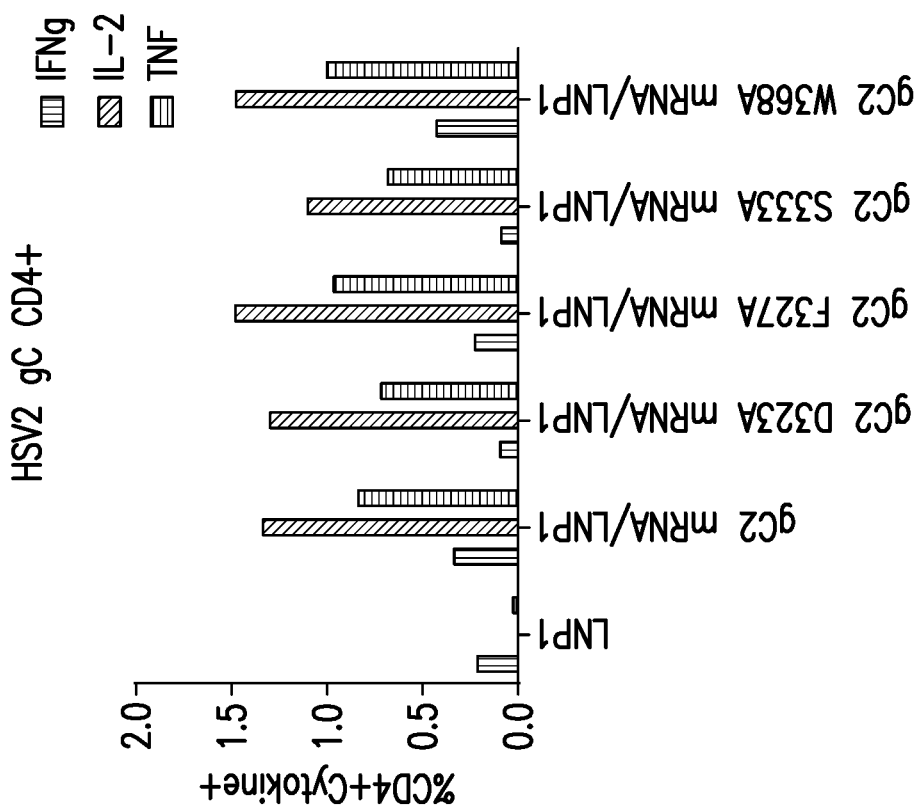
Figure 14A:
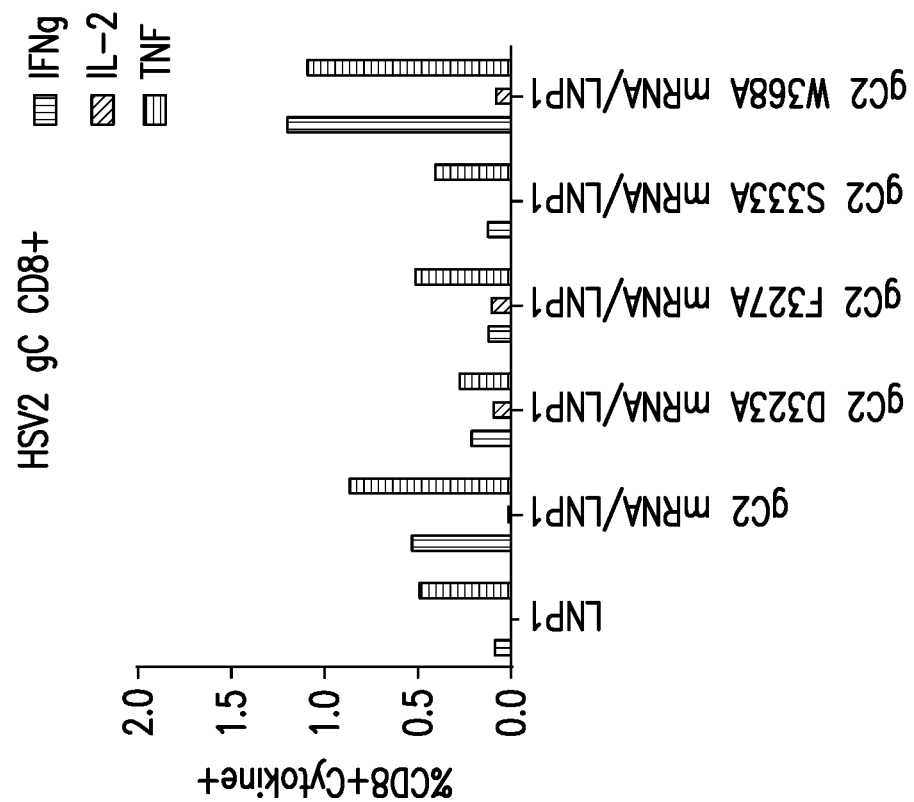
Figure 15:
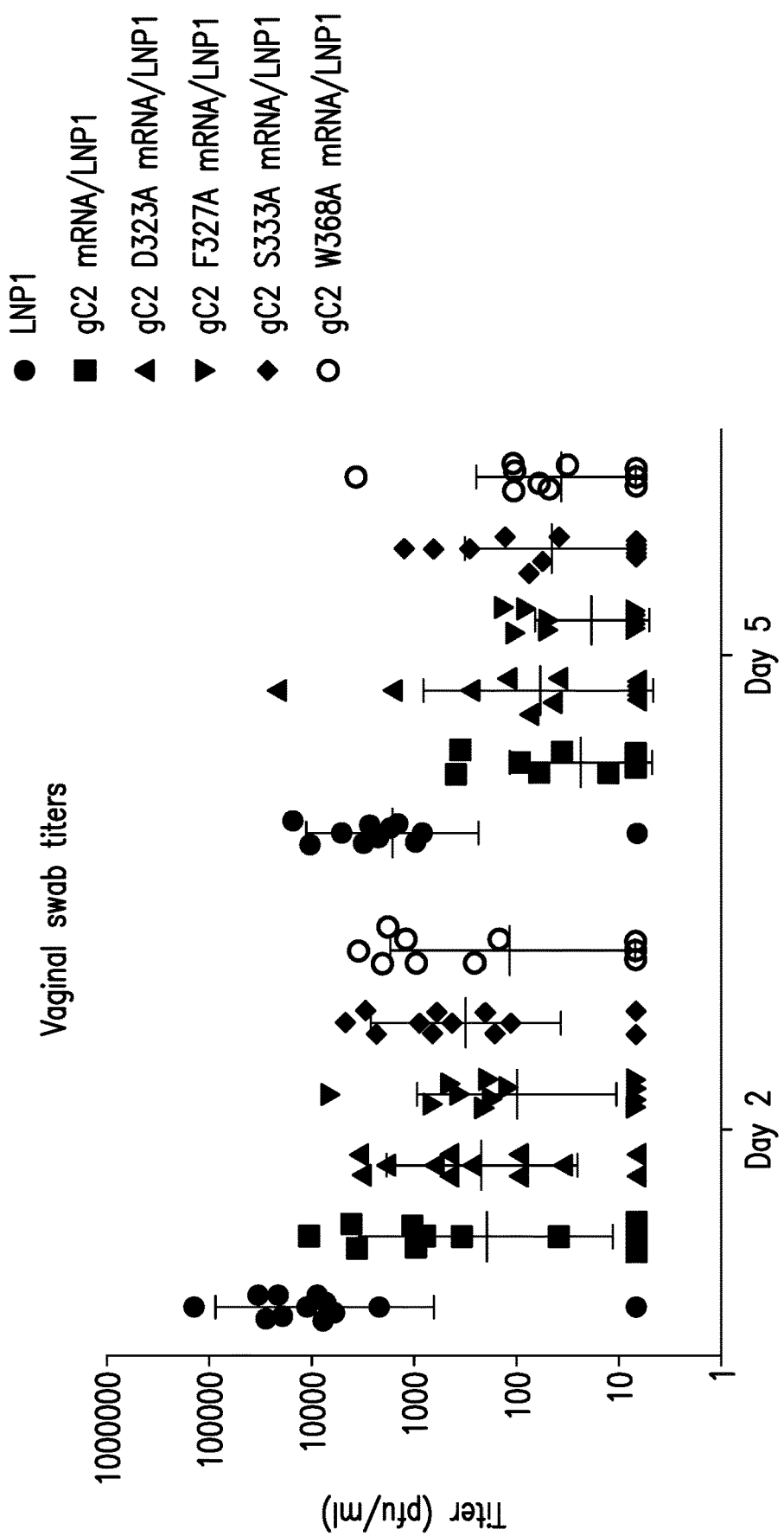

Results:

FIG. 12 sets forth the neutralizing antibody titers induced by mice vaccinated with gC2 wildtype and the various c3b gC binding mutations. As shown in FIG. 12, the F327A and W368A induced higher titers of neutralizing antibodies than wild type gC. As shown in FIG. 13, wild type and c3b binding mutants induced comparable titers of antibodies that compete c3b binding to gC, confirming the 4 mutations evaluated in this study did not disrupted the epitopes needed to elicit antibodies that inhibit c3b binding to gC. As shown in FIGS. 14*a* and 14*b* the gC mutant constructs induced comparable CD4+ and CD8+ responses except W368A which may gain an mouse T cell epitope. Mutations of c3b binding site did not affect the T cell immunogenicity. As shown in FIG. 15, immunization with gC2 wild type and c3b binding mutants protect mice from acute viral shedding. Lastly, immunization with gC2 wild type and c3b binding mutants protect mice from acute vaginal disease (as shown in the table below).

| Group | Mean Time to Clinical Signs ± SE (days) | Incidence % | Mean Survival Time ± SE (days) | Survival % |
|---|---|---|---|---|
| 1 | 5.6 ± 0.3 | 92 | 9.0 ± 0.3 | 17 |
| 2 | 7.3 ± 0.7 | 25 | 11 | 92 |
| 3 | 7.3 ± 0.3 | 25 | 13 | 92 |
| 4 | 6.4 ± 0.4 | 42 | 12.5 ± 0.5 | 83 |
| 5 | 7.4 ± 0.7 | 42 | 11 | 92 |
| 6 | 6.8 ± 0.7 | 42 | 11.7 ± 0.7 | 75 |

Example 7

Female Balb/C (CRL) mice (16/group) were administered 2 ug per mouse of vehicle (LNP only) of mRNA vaccine formulated in an LNP.

| Group (N = 16 per group) | Vaccine (mRNA formulated in LNP) | Dose of mRNA per mouse (Delivered by IM injection) | Challenge Dose (delivered intravaginally) |
|---|---|---|---|
| 1 | LNP only (Vehicle) | — | $9 \times 10^4$ pfu of HSV-2 |
| 2 | gD | 2 µg | $9 \times 10^4$ pfu of HSV-2 |
| 3 | gD + gB + gC2-F327A | 2 µg + 2 µg + 2 µg | $9 \times 10^4$ pfu of HSV-2 |

Figure 16:
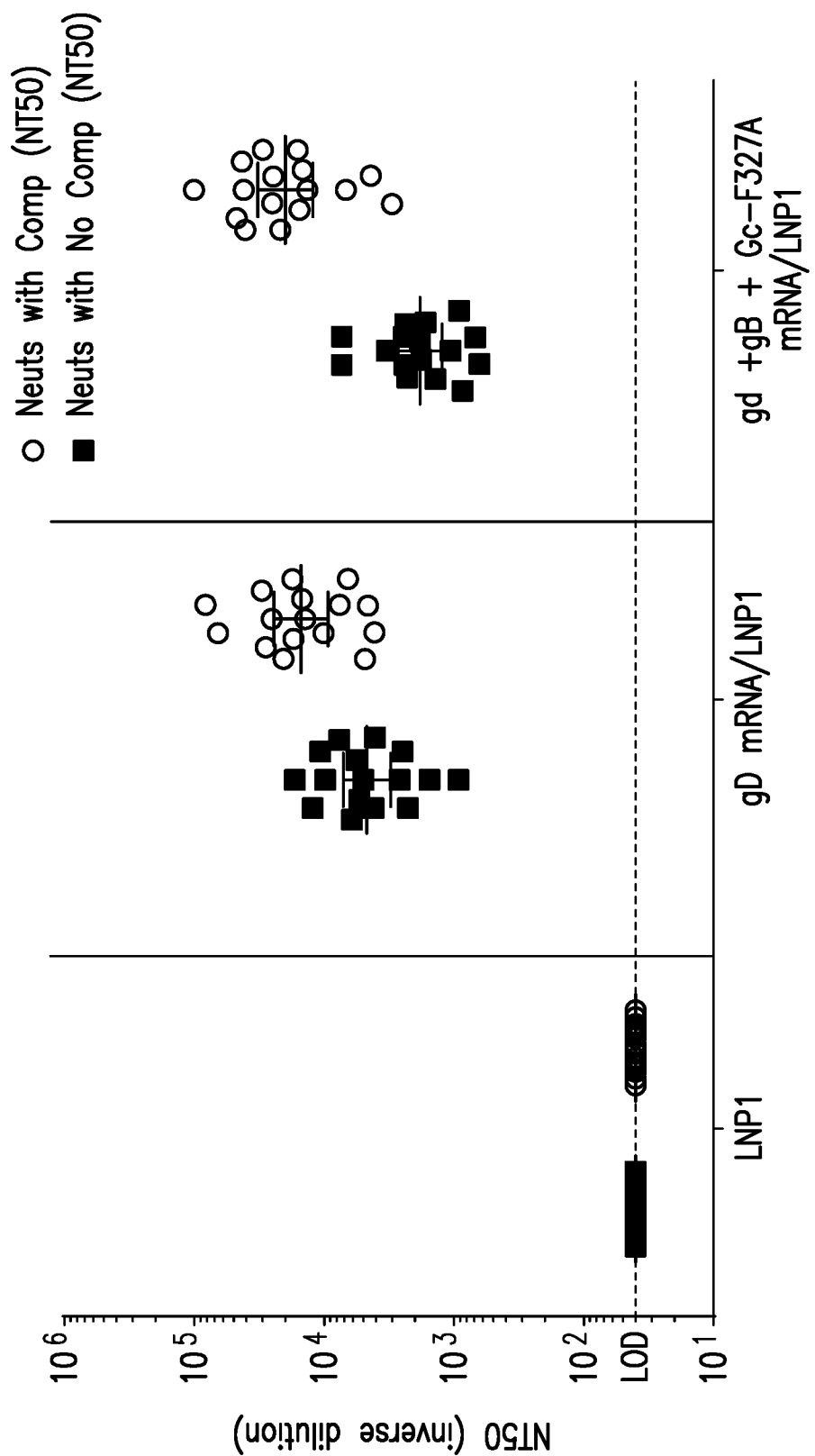

Animals were immunized on day 0 and day 21. On day 35, blood was drawn from each animal to determine HSV-2 neutralizing antibody titers. In addition, on day 35 four animals from each group were sacrificed for spleen collection. On day 42 animals were injected subcutaneously with 2 mg medoxyprogesterone (Depo-Provera®; Pfizer, Inc., New York, N.Y.), on DAY 49 animals were challenged with 9×10^4 PFU of HSV2 MS strain. On days 50-63 disease development was monitored daily. Vaginal swabs were collected on days 51 and 54 (i.e., day 2 and day 4 post HSV-2 challenge). HSV-2 Neutralization Titers were determined as described above in Example 5. As shown in FIG. 16. gD/gB/gC (F327A) mRNA formulated in LNP could induce high titers of neutralizing antibodies in mice.

TABLE 3

HSV Amino Acid Sequences

| Name | Sequence | SEQ ID NO: |
|---|---|---|
| MRK_HSV-2 gD, SQ-032180 | MGRLTSGVGTAALLVVAVGLRVVCAKYALADPSLKM ADPNRFRGKNLPVLDQLTDPPGVKRVYHIQPSLEDPFQP PSIPITVYYAVLERACRSVLLHAPSEAPQIVRGASDEARK HTYNLTIAWYRMGDNCAIPITVMEYTECPYNKSLGVCPI RTQPRWSYYDSFSAVSEDNLGFLMHAPAFETAGTYLRL VKINDWTEITQFILEHRARASCKYALPLRIPPAACLTSKA YQQGVTVDSIGMLPRFIPENQRTVALYSLKIAGWHGPKP PYTSTLLPPELSDTTNATQPELVPEDPEDSALLEDPAGTV SSQIPPNWHIPSIQDVAPHHAPAAPSNPGLIIGALAGSTLA VLVIGGIAFWVRRRAQMAPKRLRLPHIRDDDAPPSHQPL FY | 7 |
| MRK_HSV-2 SgD, SQ-032172 | MGRLTSGVGTAALLVVAVGLRVVCAKYALADPSLKM ADPNRFRGKNLPVLDQLTDPPGVKRVYHIQPSLEDPFQP PSIPITVYYAVLERACRSVLLHAPSEAPQIVRGASDEARK HTYNLTIAWYRMGDNCAIPITVMEYTECPYNKSLGVCPI RTQPRWSYYDSFSAVSEDNLGFLMHAPAFETAGTYLRL VKINDWTEITQFILEHRARASCKYALPLRIPPAACLTSKA YQQGVTVDSIGMLPRFIPENQRTVALYSLKIAGWHGPKP PYTSTLLPPELSDTTNATQPELVPEDPEDSALLEDPAGTV SSQIPPNWHIPSIQDVAPHHAPAAPSNP | 8 |
| MRK_HSV-2 gB, SQ-032178 | MRGGGLVCALVVGALVAAVASAAPAAPRASGGVAAT VAANGGPASQPPPVPSPATTKARKRKTKKPPKRPEATPP PDANATVAAGHATLRAHLREIKVENADAQFYVCPPPTG ATVVQFEQPRRCPTRPEGQNYTEGIAVVFKENIAPYKFK ATMYYKDVTVSQVWFGHRYSQFMGIFEDRAPVPFEEVI DKINAKGVCRSTAKYVRNNMETTAFHRDDHETDMELK PAKVATRTSRGWHTTDLKYNPSRVEAFHRYGTTVNCIV EEVDARSVYPYDEFVLATGDFVYMSPFYGYREGSHTEH TSYAADRFKQVDGFYARDLTTKARATSPTTRNLLTTPK PTVAWDWVPKRPAVCTMTKWQEVDEMLRAEYGGSFR FSSDAISTTFTTNLTQYSLSRVDLGDCIGRDAREAIDRMF ARKYNATHIKVGQPQYYLATGGFLIAYQPLLSNTLAEL YVREYMREQDRKPRNATPAPLREAPSANASVERIKTTSS IEFARLQFTYNHIQRHVNDMLGRIAVAWCELQNHELTL WNEARKLNPNAIASATVGRRVSARMLGDVMAVSTCVP VAPDNVIVQNSMRVSSRPGTCYSRPLVSFRYEDQGPLIE GQLGENNELRLTRDALEPCTVGHRRYFIFGGGYVYFEE YAYSHQLSRADVTTVSTFIDLNITMLEDHEFVPLEVYTR HEIKDSGLLDYTEVQRRNQLHDLRFADIDTVIRADANA AMFAGLCAFFEGMGPLGRAVGKVVMGVVGGVVSAVS GVSSFMSNPFGALAVGLLVLAGLVAAFFAFRYVLQLQR | 9 |

TABLE 3-continued

| HSV Amino Acid Sequences | | |
|---|---|---|
| Name | Sequence | SEQ ID NO: |
| | NPMKALYPLTTKELKTSDPGGVGGEGEEGAEGGGFDEA KLAEAPREMIRYMALVSAMERTEHKARKKGTSALLSSK VTNMVLRKRNKARYSPLHNEDEAGDEDEL | |
| MRK_HSV-2 SgB, SQ-032210 | MRGGGLVCALVVGALVAAVASAAPAAPRASGGVAAT VAANGGPASQPPPVPSPATTKARKRKTKKPPKRPEATPP PDANATVAAGHATLRAHLREIKVENADAQFYVCPPPTG ATVVQFEQPRRCPTRPEGQNYTEGIAVVFKENIAPYKFK ATMYYKDVTVSQVWFGHRYSQFMGIFEDRAPVPFEEVI DKINAKGVCRSTAKYVRNNMETTAFHRDDHETDMELK PAKVATRTSRGWHTTDLKYNPSRVEAFHRYGTTVNCIV EEVDARSVYPYDEFVLATGDFVYMSPFYGYREGSHTEH TSYAADRFKQVDGFYARDLTTKARATSPTTRNLLTTPK FTVAWDWVPKRPAVCTMTKWQBVDEMLRAEYGGSFR FSSDAISTTFTTNLTQYSLSRVDLGDCIGRDAREAIDRMF ARKYNATHIKVGQPQYYLATGGFLIAYQPLLSNTLAEL YVREYMREQDRKPRNATPAPLREAPSANASVERIKTTSS IEFARLQFTYNHIQRHVNDMLGRIAVAWCELQNHELTL WNEARKLNPNAIASATVGRRVSARMLGDVMAVSTCVP VAPDNVIVQNSMRVSSRPGTCYSRPLVSFRYEDQGPLIE GQLGENNELRLTRDALEPCTVGHRRYFIFGGGYVYFEE YAYSHQLSRADVTTVSTFIDLNITMLEDHEFVPLEVYTR HEIKDSGLLDYTEVQRRNQLHDLRFADIDTVIRADANA AMFAGLCAFFEGMGDLGRAVGKVVMGVVGGVVSAVS GVSSFMSNP | 10 |
| MRK_HSV-2 gC, SQ-032179 | MALGRVGLAVGLWGLLWVGVVVVLANASPGRTITVGP RGNASNAAPSASPRNASAPRTTPTPPQPRKATKSKASTA KPAPPPKTGPPKTSSEPVRCNRHDPLARYGSRVQIRCRFP NSTRTESRLQIWRYATATDAEIGTAPSLEEVMVNVSAPP GGQLVYDSAPNRTDPHVIWAEGAGPGASPRLYSVVGPL GRQRLIIEELTLETQGMYYWVWGRTDRPSAYGTWVRV RVFRPPSLTIHPHAVLEGQPFKATCTAATYYPGNRAEFV WFEDGRRVFDPAQIHTQTQENPDGFSTVSTVTSAAVGG QGPPRTFTCQLTWHRDSVSFSRRNASGTASVLPRPTITM EFTGDHAVCTAGCVPEGVTFAWFLGDDSSPAEKVAVAS QTSCGRPGTATIRSTLPVSYEQTEYICRLAGYPDGIPVLE HHGSHQPPPRIDPTERQVIRAVEGAGIGVAVLVAVVLAG TAVVYLTHASSVRYRRLR | 11 |
| MRK_HSV-2 SgC, SQ-032835 | MALGRVGLAVGLWGLLWVGVVVVLANASPGRTITVGP RGNASNAAPSASPRNASAPRTTPTPPQPRKATKSKASTA KPAPPPKTGPPKTSSEPVRCNRHDPLARYGSRVQIRCRFP NSTRTESRLQIWRYATATDAEIGTAPSLEEVMVNVSAPP GGQLVYDSAPNRTDPHVIWAEGAGPGASPRLYSVVGPL GRQRLIIEELTLETQGMYYWVWGRTDRPSAYGTWVRV RVFRPPSLTIHPHAVLEGQPFKATCTAATYYPGNRAEFV WFEDGRRVFDPAQIHTQTQENPDGFSTVSTVTSAAVGG QGPPRTFTCQLTWHRDSVSFSRRNASGTASVLPRPTTTM EFTGDHAVCTAGCVPEGVTFAWFLGDDSSPAEKVAVAS QTSCGRPGTATIRSTLPYVSYEQTEYICRLAGYPDGIPVLE HHGSHQPPPRDPTERQVIRAVEG | 12 |
| MRK_HSV-2 gE SQ-032181 | MARGAGLVFFVGVWVVSCLAAAPRTSWKRVTSGEDV VLLPAPAGPEERTRAHKLLWAAEPLDACGPLRPSWVAL WPPRRVLETVVDAACMRAPEPLAIAYSPPFPAGDEGLY SELAWRDRVAVVNESLVIYGALETDSGLYTLSVVGLSD EARQVASVVLVVEPAPVPTPTPDDYDEEDDAGVSERTP VSVPPPTPPRRPPVAPPTHPRVIPEVSHVRGVTVHMETPE AILFAPGETFGTNVSIHAIAHDDGPYAMDVVWMRFDVP SSCAEMRIYEACLYHPQLPECLSPADAPCAVSSWAYRL AVRSYAGCSRTTPPPRCFAEARMEPVPGLAWLASTVNL EFQHASPQHAGLYLCVVYVDDHIHAWGHMTISTAAQY RNAVVEQHLPQRQPEPVEPTRPHVRAPPPAPSARGPLRL GAVLGAALLLAALGLSAWACMTCWRRRSWRAVKSRA SATGPTYIRVADSELYADWSSDSEGERDGSLWQDPPER PDSPSTNGSGFEILSPTAPSVYPHSEGRKSRRPLTTFGSGS PGRRHSQASYSSVLW | 13 |
| MRK_HSV-2 SgE, SQ-032211 | MARGAGLVFFVGVWVVSCLAAAPRTSWKRVTSGEDV YLLPAPAGPEERTRAHKLLWAAEPLDACGPLRPSWVAL WPPRRVLETVVDAACMRAPEPLAIAYSPPFPAGDEGLY SELAWRDRVAVVNESLVIYGALETDSGLYTLSVVGLSD EARQVASVVLVVEPAPVPTPTPDDYDEEDDAGVSERTP VSVPPPTPPRRPPVAPPTHPRVIPEVSHVRGVTVHMETPE AILFAPGETFGTNVSIHAIAHDDGPYAMDVVWMRFDVP | 14 |

TABLE 3-continued

HSV Amino Acid Sequences

| Name | Sequence | SEQ ID NO: |
|---|---|---|
| | SSCAEMRIYEACLYHPQLPECLSPADAPCAVSSWAYRL<br>AVRSYAGCSRTTPPPRCFAEARMEPVPGLAWLASTVNL<br>EFQHASPQHAGLYLCVVYVDDHIHAWGHMTISTAAQY<br>RNAVVEQHLPQRQPEPVEPTRPHVRAPPPAPSARGPLR | |
| MRK_HSV-2 gI,<br>SQ-032182 | MPGRSLQGLAILGLWVCATGLVVRGPTVSLVSDSLVDA<br>GAVGPQGFVEEDLRVFGELHFVGAQVPHTNYYDGIIELF<br>HYPLGNHCPRVVHVVTLTACPRRPAVAFTLCRSTHHAH<br>SPAYPTLELGLARQPLLRVRTATRDYAGLYVLRVWVGS<br>ATNASLFVLGVALSANGTFVYNGSDYGSCDPAQLPFSA<br>PRLGPSSVYTPGASRPTPPRTTTSPSSPRDPTPAPGDTGTP<br>APASGERAPPNSTRSASESRHRLTVAQVIQIAIPASIIAFV<br>FLGSCICFIHRCQRRYRRPRGQIYNPGGVSCAVNEAAMA<br>RLGAELRSHPNTPPKPRRRSSSSTTMPSLTSIAEESEPGPV<br>VLLSVSPRPRSGPTAPQEV | 15 |
| MRK_HSV-2 SgI,<br>SQ-032323 | MPGRSLQGLAILGLWVCATGLVVRGPTVSLVSDSLVDA<br>GAVGPQGFVEEDLRVFGELHFVGAQVPHTNYYDGIIELF<br>HYPLGNHCPRVVHVVTLTACPRRPAVAFTLCRSTHHAH<br>SPAYPTLELGLARQPLLRVRTATRDYAGLYVLRVWVGS<br>ATNASLFVLGVALSANGTFVYNGSDYGSCDPAQLPFSA<br>PRLGPSSVYTPGASRPTPPRTTTSPSSPRDPTPAPGDTGTP<br>APASGERAPPNSTRSASESRHRLTVAQVIQ | 16 |

All references, including patent documents, disclosed herein are incorporated by reference in their entirety.

```
                        SEQUENCE LISTING

<160> NUMBER OF SEQ ID NOS: 16

<210> SEQ ID NO 1
<211> LENGTH: 812
<212> TYPE: PRT
<213> ORGANISM: Artificial Sequence
<220> FEATURE:
<223> OTHER INFORMATION: HSV-2 gB-G1 peptide

<400> SEQUENCE: 1

Met Arg Gly Gly Gly Leu Val Cys Ala Leu Val Val Gly Ala Leu Val
1               5                   10                  15

Ala Ala Val Ala Ser Ala Ala Pro Ala Ala Pro Arg Ala Ser Gly Gly
            20                  25                  30

Val Ala Ala Thr Val Ala Ala Asn Gly Gly Pro Ala Ser Gln Pro Pro
        35                  40                  45

Pro Val Pro Ser Pro Ala Thr Thr Lys Ala Arg Lys Arg Lys Thr Lys
    50                  55                  60

Lys Pro Pro Lys Arg Pro Glu Ala Thr Pro Pro Asp Ala Asn Ala
65                  70                  75                  80

Thr Val Ala Ala Gly His Ala Thr Leu Arg Ala His Leu Arg Glu Ile
                85                  90                  95

Lys Val Glu Asn Ala Asp Ala Gly Phe Tyr Val Cys Pro Pro Pro Thr
            100                 105                 110

Gly Ala Thr Val Val Gln Phe Glu Gln Pro Arg Arg Cys Pro Thr Arg
        115                 120                 125

Pro Glu Gly Gln Asn Tyr Thr Glu Gly Ile Ala Val Val Phe Lys Glu
    130                 135                 140

Asn Ile Ala Pro Tyr Lys Phe Lys Ala Thr Met Tyr Tyr Lys Asp Val
145                 150                 155                 160

Thr Val Ser Gln Val Trp Phe Gly His Arg Tyr Ser Gln Phe Met Gly
```

-continued

```
                165                 170                 175
Ile Phe Glu Asp Arg Ala Pro Val Pro Phe Glu Val Ile Asp Lys
                    180                 185                 190
Ile Asn Ala Lys Gly Val Cys Arg Ser Thr Ala Lys Tyr Val Arg Asn
                    195                 200                 205
Asn Met Glu Thr Thr Ala Phe His Arg Asp Asp His Glu Thr Asp Met
        210                 215                 220
Glu Leu Lys Pro Ala Lys Val Ala Thr Arg Thr Ser Arg Gly Trp His
225                 230                 235                 240
Thr Thr Asp Leu Lys Tyr Asn Pro Ser Arg Val Glu Ala Phe His Arg
                    245                 250                 255
Tyr Gly Thr Thr Val Asn Cys Ile Val Glu Glu Val Asp Ala Arg Ser
                260                 265                 270
Val Tyr Pro Tyr Asp Glu Phe Val Leu Ala Thr Gly Asp Phe Val Tyr
                275                 280                 285
Met Ser Pro Phe Tyr Gly Tyr Arg Glu Gly Ser His Thr Glu His Thr
        290                 295                 300
Ser Tyr Ala Ala Asp Arg Phe Lys Gln Val Asp Gly Phe Tyr Ala Arg
305                 310                 315                 320
Asp Leu Thr Thr Lys Ala Arg Ala Thr Ser Pro Thr Arg Asn Leu
                    325                 330                 335
Leu Thr Thr Pro Lys Phe Thr Val Ala Trp Asp Trp Val Pro Lys Arg
                340                 345                 350
Pro Ala Val Cys Thr Met Thr Lys Trp Gln Glu Val Asp Glu Met Leu
                355                 360                 365
Arg Ala Glu Tyr Gly Gly Ser Phe Arg Phe Ser Ser Asp Ala Ile Ser
            370                 375                 380
Thr Thr Phe Thr Thr Asn Leu Thr Gln Tyr Ser Leu Ser Arg Val Asp
385                 390                 395                 400
Leu Gly Asp Cys Ile Gly Arg Asp Ala Arg Glu Ala Ile Asp Arg Met
                405                 410                 415
Phe Ala Arg Lys Tyr Asn Ala Thr His Ile Lys Val Gly Gln Pro Gln
                420                 425                 430
Tyr Tyr Leu Ala Thr Gly Gly Phe Leu Ile Ala Tyr Gln Pro Leu Leu
            435                 440                 445
Ser Asn Thr Leu Ala Glu Leu Tyr Val Arg Glu Tyr Met Arg Glu Gln
        450                 455                 460
Asp Arg Lys Pro Arg Asn Ala Thr Pro Ala Pro Leu Arg Glu Ala Pro
465                 470                 475                 480
Ser Ala Asn Ala Ser Val Glu Arg Ile Lys Thr Thr Ser Ser Ile Glu
                    485                 490                 495
Phe Ala Arg Leu Gln Phe Thr Tyr Asn His Ile Gln Arg His Val Asn
                500                 505                 510
Asp Met Leu Gly Arg Ile Ala Val Ala Trp Cys Glu Leu Gln Asn His
            515                 520                 525
Glu Leu Thr Leu Trp Asn Glu Ala Arg Lys Leu Asn Pro Asn Ala Ile
        530                 535                 540
Ala Ser Ala Thr Val Gly Arg Arg Val Ser Ala Arg Met Leu Gly Asp
545                 550                 555                 560
Val Met Ala Val Ser Thr Cys Val Pro Val Ala Pro Asp Asn Val Ile
                    565                 570                 575
Val Gln Asn Ser Met Arg Val Ser Ser Arg Pro Gly Thr Cys Tyr Ser
                580                 585                 590
```

-continued

```
Arg Pro Leu Val Ser Phe Arg Tyr Glu Asp Gln Gly Pro Leu Ile Glu
            595                 600                 605

Gly Gln Leu Gly Glu Asn Asn Glu Leu Arg Leu Thr Arg Asp Ala Leu
    610                 615                 620

Glu Pro Cys Thr Val Gly His Arg Arg Tyr Phe Ile Phe Gly Gly Gly
625                 630                 635                 640

Tyr Val Tyr Phe Glu Glu Tyr Ala Tyr Ser His Gln Leu Ser Arg Ala
                645                 650                 655

Asp Val Thr Thr Val Ser Thr Phe Ile Asp Leu Asn Ile Thr Met Leu
            660                 665                 670

Glu Asp His Glu Phe Val Pro Leu Glu Val Tyr Thr Arg His Glu Ile
        675                 680                 685

Lys Asp Ser Gly Leu Leu Asp Tyr Thr Glu Val Gln Arg Arg Asn Gln
    690                 695                 700

Leu His Asp Leu Arg Phe Ala Asp Ile Asp Thr Val Ile Arg Ala Asp
705                 710                 715                 720

Ala Asn Ala Ala Met Phe Ala Gly Leu Cys Ala Phe Phe Glu Gly Met
                725                 730                 735

Gly Asp Leu Gly Arg Ala Val Gly Lys Val Val Met Gly Val Val Gly
            740                 745                 750

Gly Val Val Ser Ala Val Ser Gly Val Ser Ser Phe Met Ser Asn Pro
        755                 760                 765

Phe Phe Phe Ile Ile Gly Leu Ile Ile Gly Leu Phe Leu Val Leu Arg
    770                 775                 780

Val Gly Ile His Leu Cys Ile Lys Leu Lys His Thr Lys Lys Arg Gln
785                 790                 795                 800

Ile Tyr Thr Asp Ile Glu Met Asn Arg Leu Gly Lys
                805                 810

<210> SEQ ID NO 2
<211> LENGTH: 480
<212> TYPE: PRT
<213> ORGANISM: Artificial Sequence
<220> FEATURE:
<223> OTHER INFORMATION: HSV-2  gC_DX_ W368A peptide

<400> SEQUENCE: 2

Met Ala Leu Gly Arg Val Gly Leu Ala Val Gly Leu Trp Gly Leu Leu
1               5                   10                  15

Trp Val Gly Val Val Val Leu Ala Asn Ala Ser Pro Gly

-continued

```
Glu Val Met Val Asn Val Ser Ala Pro Pro Gly Gln Leu Val
145                 150                 155                 160

Tyr Asp Ser Ala Pro Asn Arg Thr Asp Pro His Val Ile Trp Ala Glu
                165                 170                 175

Gly Ala Gly Pro Gly Ala Ser Pro Arg Leu Tyr Ser Val Gly Pro
            180                 185                 190

Leu Gly Arg Gln Arg Leu Ile Ile Glu Glu Leu Thr Leu Glu Thr Gln
            195                 200                 205

Gly Met Tyr Tyr Trp Val Trp Gly Arg Thr Asp Arg Pro Ser Ala Tyr
210                 215                 220

Gly Thr Trp Val Arg Val Arg Val Phe Arg Pro Pro Ser Leu Thr Ile
225                 230                 235                 240

His Pro His Ala Val Leu Glu Gly Gln Pro Phe Lys Ala Thr Cys Thr
                245                 250                 255

Ala Ala Thr Tyr Tyr Pro Gly Asn Arg Ala Glu Phe Val Trp Phe Glu
            260                 265                 270

Asp Gly Arg Arg Val Phe Asp Pro Ala Gln Ile His Thr Gln Thr Gln
            275                 280                 285

Glu Asn Pro Asp Gly Phe Ser Thr Val Ser Thr Val Thr Ser Ala Ala
290                 295                 300

Val Gly Gly Gln Gly Pro Pro Arg Thr Phe Thr Cys Gln Leu Thr Trp
305                 310                 315                 320

His Arg Asp Ser Val Ser Phe Ser Arg Arg Asn Ala Ser Gly Thr Ala
                325                 330                 335

Ser Val Leu Pro Arg Pro Thr Ile Thr Met Glu Phe Thr Gly Asp His
            340                 345                 350

Ala Val Cys Thr Ala Gly Cys Val Pro Glu Gly Val Thr Phe Ala Ala
            355                 360                 365

Phe Leu Gly Asp Asp Ser Ser Pro Ala Glu Lys Val Ala Val Ala Ser
370                 375                 380

Gln Thr Ser Cys Gly Arg Pro Gly Thr Ala Thr Ile Arg Ser Thr Leu
385                 390                 395                 400

Pro Val Ser Tyr Glu Gln Thr Glu Tyr Ile Cys Arg Leu Ala Gly Tyr
                405                 410                 415

Pro Asp Gly Ile Pro Val Leu Glu His His Gly Ser His Gln Pro Pro
            420                 425                 430

Pro Arg Asp Pro Thr Glu Arg Gln Val Ile Arg Ala Val Glu Gly Ala
            435                 440                 445

Gly Ile Gly Val Ala Val Leu Val Ala Val Val Leu Ala Gly Thr Ala
        450                 455                 460

Val Val Tyr Leu Thr His Ala Ser Ser Val Arg Tyr Arg Arg Leu Arg
465                 470                 475                 480
```

<210> SEQ ID NO 3
<211> LENGTH: 480
<212> TYPE: PRT
<213> ORGANISM: Artificial Sequence
<220> FEATURE:
<223> OTHER INFORMATION: HSV-2  gC_DX D323A Peptide

<400> SEQUENCE: 3

```
Met Ala Leu Gly Arg Val Gly Leu Ala Val Gly Leu Trp Gly Leu Leu
1               5                   10                  15

Trp Val Gly Val Val Val Leu Ala Asn Ala Ser Pro Gly Arg Thr
                20                  25                  30
```

```
Ile Thr Val Gly Pro Arg Gly Asn Ala Ser Asn Ala Ala Pro Ser Ala
         35                  40                  45

Ser Pro Arg Asn Ala Ser Ala Pro Arg Thr Thr Pro Thr Pro Pro Gln
 50                  55                  60

Pro Arg Lys Ala Thr Lys Ser Lys Ala Ser Thr Ala Lys Pro Ala Pro
 65                  70                  75                  80

Pro Pro Lys Thr Gly Pro Pro Lys Thr Ser Ser Glu Pro Val Arg Cys
                 85                  90                  95

Asn Arg His Asp Pro Leu Ala Arg Tyr Gly Ser Arg Val Gln Ile Arg
                100                 105                 110

Cys Arg Phe Pro Asn Ser Thr Arg Thr Glu Ser Arg Leu Gln Ile Trp
                115                 120                 125

Arg Tyr Ala Thr Ala Thr Asp Ala Glu Ile Gly Thr Ala Pro Ser Leu
        130                 135                 140

Glu Glu Val Met Val Asn Val Ser Ala Pro Pro Gly Gly Gln Leu Val
145                 150                 155                 160

Tyr Asp Ser Ala Pro Asn Arg Thr Asp Pro His Val Ile Trp Ala Glu
                165                 170                 175

Gly Ala Gly Pro Gly Ala Ser Pro Arg Leu Tyr Ser Val Gly Pro
                180                 185                 190

Leu Gly Arg Gln Arg Leu Ile Ile Glu Glu Leu Thr Leu Glu Thr Gln
        195                 200                 205

Gly Met Tyr Tyr Trp Val Trp Gly Arg Thr Asp Arg Pro Ser Ala Tyr
        210                 215                 220

Gly Thr Trp Val Arg Val Arg Val Phe Arg Pro Pro Ser Leu Thr Ile
225                 230                 235                 240

His Pro His Ala Val Leu Glu Gly Gln Pro Phe Lys Ala Thr Cys Thr
                245                 250                 255

Ala Ala Thr Tyr Tyr Pro Gly Asn Arg Ala Glu Phe Val Trp Phe Glu
                260                 265                 270

Asp Gly Arg Arg Val Phe Asp Pro Ala Gln Ile His Thr Gln Thr Gln
        275                 280                 285

Glu Asn Pro Asp Gly Phe Ser Thr Val Ser Thr Val Thr Ser Ala Ala
        290                 295                 300

Val Gly Gly Gln Gly Pro Pro Arg Thr Phe Thr Cys Gln Leu Thr Trp
305                 310                 315                 320

His Arg Ala Ser Val Ser Phe Ser Arg Arg Asn Ala Ser Gly Thr Ala
                325                 330                 335

Ser Val Leu Pro Arg Pro Thr Ile Thr Met Glu Phe Thr Gly Asp His
                340                 345                 350

Ala Val Cys Thr Ala Gly Cys Val Pro Glu Gly Val Thr Phe Ala Trp
                355                 360                 365

Phe Leu Gly Asp Asp Ser Ser Pro Ala Glu Lys Val Ala Val Ala Ser
        370                 375                 380

Gln Thr Ser Cys Gly Arg Pro Gly Thr Ala Thr Ile Arg Ser Thr Leu
385                 390                 395                 400

Pro Val Ser Tyr Glu Gln Thr Glu Tyr Ile Cys Arg Leu Ala Gly Tyr
                405                 410                 415

Pro Asp Gly Ile Pro Val Leu Glu His His Gly Ser His Gln Pro Pro
                420                 425                 430

Pro Arg Asp Pro Thr Glu Arg Gln Val Ile Arg Ala Val Glu Gly Ala
        435                 440                 445
```

```
Gly Ile Gly Val Ala Val Leu Val Ala Val Val Leu Ala Gly Thr Ala
            450                 455                 460
Val Val Tyr Leu Thr His Ala Ser Ser Val Arg Tyr Arg Arg Leu Arg
465                 470                 475                 480

<210> SEQ ID NO 4
<211> LENGTH: 480
<212> TYPE: PRT
<213> ORGANISM: Artificial Sequence
<220> FEATURE:
<223> OTHER INFORMATION: HSV-2  gC_DX_ F327A Peptide

<400> SEQUENCE: 4

Met Ala Leu Gly Arg Val Gly Leu Ala Val Gly Leu Trp Gly Leu Leu
1               5                   10                  15
Trp Val Gly Val Val Val Leu Ala Asn Ala Ser Pro Gly Arg Thr
            20                  25                  30
Ile Thr Val Gly Pro Arg Gly Asn Ala Ser Asn Ala Ala Pro Ser Ala
            35                  40                  45
Ser Pro Ar

-continued

```
Ser Val Leu Pro Arg Pro Thr Ile Thr Met Glu Phe Thr Gly Asp His
            340                 345                 350

Ala Val Cys Thr Ala Gly Cys Val Pro Glu Gly Val Thr Phe Ala Trp
        355                 360                 365

Phe Leu Gly Asp Asp Ser Ser Pro Ala Glu Lys Val Ala Val Ala Ser
    370                 375                 380

Gln Thr Ser Cys Gly Arg Pro Gly Thr Ala Thr Ile Arg Ser Thr Leu
385                 390                 395                 400

Pro Val Ser Tyr Glu Gln Thr Glu Tyr Ile Cys Arg Leu Ala Gly Tyr
                405                 410                 415

Pro Asp Gly Ile Pro Val Leu Glu His His Gly Ser His Gln Pro Pro
            420                 425                 430

Pro Arg Asp Pro Thr Glu Arg Gln Val Ile Arg Ala Val Glu Gly Ala
        435                 440                 445

Gly Ile Gly Val Ala Val Leu Val Ala Val Val Leu Ala Gly Thr Ala
    450                 455                 460

Val Val Tyr Leu Thr His Ala Ser Ser Val Arg Tyr Arg Arg Leu Arg
465                 470                 475                 480
```

<210> SEQ ID NO 5
<211> LENGTH: 480
<212> TYPE: PRT
<213> ORGANISM: Artificial Sequence
<220> FEATURE:
<223> OTHER INFORMATION: HSV-2  gC_DX_ S333A peptide

<400> SEQUENCE: 5

```
Met Ala Leu Gly Arg Val Gly Leu Ala Val Gly Leu Trp Gly Leu Leu
1               5                   10                  15

Trp Val Gly Val Val Val Leu Ala Asn Ala Ser Pro Gly Arg Thr
            20                  25                  30

Ile Thr Val G

Gly Thr Trp Val Arg Val Arg Val Phe Arg Pro Ser Leu Thr Ile
225                 230                 235                 240

His Pro His Ala Val Leu Glu Gly Gln Pro Phe Lys Ala Thr Cys Thr
            245                 250                 255

Ala Ala Thr Tyr Tyr Pro Gly Asn Arg Ala Glu Phe Val Trp Phe Glu
        260                 265                 270

Asp Gly Arg Arg Val Phe Asp Pro Ala Gln Ile His Thr Gln Thr Gln
    275                 280                 285

Glu Asn Pro Asp Gly Phe Ser Thr Val Ser Thr Val Thr Ser Ala Ala
290                 295                 300

Val Gly Gln Gly Pro Pro Arg Thr Phe Thr Cys Gln Leu Thr Trp
305                 310                 315                 320

His Arg Asp Ser Val Ser Phe Ser Arg Arg Asn Ala Ala Gly Thr Ala
            325                 330                 335

Ser Val Leu Pro Arg Pro Thr Ile Thr Met Glu Phe Thr Gly Asp His
        340                 345                 350

Ala Val Cys Thr Ala Gly Cys Val Pro Glu Gly Val Thr Phe Ala Trp
    355                 360                 365

Phe Leu Gly Asp Asp Ser Ser Pro Ala Glu Lys Val Ala Val Ala Ser
370                 375                 380

Gln Thr Ser Cys Gly Arg Pro Gly Thr Ala Thr Ile Arg Ser Thr Leu
385                 390                 395                 400

Pro Val Ser Tyr Glu Gln Thr Glu Tyr Ile Cys Arg Leu Ala Gly Tyr
            405                 410                 415

Pro Asp Gly Ile Pro Val Leu Glu His His Gly Ser His Gln Pro Pro
        420                 425                 430

Pro Arg Asp Pro Thr Glu Arg Gln Val Ile Arg Ala Val Glu Gly Ala
    435                 440                 445

Gly Ile Gly Val Ala Val Leu Val Ala Val Val Leu Ala Gly Thr Ala
450                 455                 460

Val Val Tyr Leu Thr His Ala Ser Ser Val Arg Tyr Arg Arg Leu Arg
465                 470                 475                 480

<210> SEQ ID NO 6
<211> LENGTH: 2647
<212> TYPE: DNA
<213> ORGANISM: Artificial Sequence
<220> FEATURE:
<223> OTHER INFORMATION: HSV-2  gB-G1 DNA

<400> SEQUENCE: 6
tcaagctttt ggaccctcgt acagaagcta atacgactca ctatagggaa ataagagaga      60
aaagaagagt aagaagaaat ataagagcca ccatgagagg cggcggcctt gtgtgcgccc     120
tagtggtggg agcccttgtg ccgccgtag caagcgccgc ccctgcggcc caagagcca      180 gcggcggcgt ggcagcaaca gttgccgcta acgcggccc agccagccag cctcctccag     240
tgcctagccc agctaccacc aaggccagaa agagaaagac caagaagcct cctaagcgtc     300
ctgaggccac cccaccacca gacgccaatg cgaccgtggc cgcaggccac gccacccctga    360 gagcccacct gagagagatc aaggtggaga cgccgacgc ccagttctac gtgtgtcctc      420
cgcctaccgg tgcaacagtg gtgcagttcg agcagctag aagatgccct acccgaccag      480
agggtcagaa ctacaccgag ggcatcgccg tggtgttcaa ggagaacatc gcccttaca      540 agttcaaggc caccatgtac tacaaggacg tgaccgtgag ccaggtgtgg ttcggccaca     600
gatacagcca gttcatgggc atcttcgagg acagagcccc agtacctttc gaggaggtga     660

-continued

```
tcgacaagat caacgccaag ggcgtgtgca gaagcaccgc caagtacgtg agaaacaaca      720
tggagacaac cgccttccac agagacgacc acgaaaccga catggagctg aagcctgcca      780
aggtggccac cagaaccagc agaggctggc acaccaccga cctgaagtac aaccctagca      840
gagtggaggc gttccaccga tacggcacca ccgtgaactg catcgtggaa gaggtcgacg      900
ccagaagcgt gtaccttac gacgagttcg tgctggccac cggcgacttc gtgtacatga       960 gcccttteta cggctacaga gagggcagcc acaccgagca caccagctac gccgccgaca      1020
gattcaagca agttgacggc ttctacgccc gggatcttac aactaaggct agagcaacta      1080
gccctactac taggaacctg cttactaccc ctaagttcac agtggcctgg gactgggtgc      1140
ctaagaggcc tgccgtgtgc accatgacca gtggcagga agtcgacgag atgcttcgcg       1200
cagagtacgg cggcagcttc agattcagca gcgacgccat cagcaccacc ttcaccacaa      1260
acctgaccca gtacagcctg tctcgagtcg acctgggcga ttgtatcggc agagatgcaa     1320
gagaggccat cgacagaatg ttcgccagga agtataacgc tacccacatt aaggtgggtc      1380
agccacagta ctacctagca actggcggct tcctgatcgc ctaccagcct ctgctgagca      1440
acaccctggc cgagctctac gtacgggaat atatgagaga gcaggacaga aagccaagga     1500
acgcaactcc tgcccctctg agggaagctc ctagcgccaa cgccagcgtg agagaatca      1560 agaccaccag cagcatcgaa ttcgcccggc tgcagttcac ctacaaccac atccagagac      1620
acgtgaacga catgctgggc agaatcgctg tggcttggtg cgagctgcag aaccacgagc      1680
tgaccctgtg gaacgaggcg cgcaagctga accctaacgc catcgcctcc gccaccgtgg      1740
gtaggagagt gagcgccaga atgctgggag atgtgatggc cgtgagcacc tgcgtgcctg      1800
tggcccctga caacgtgatc gtgcagaaca gcatgcgggt tagcagcaga cctggcaccct     1860 gctactcacg acctctggtg tcattcagat acgaggacca gggccctctg atcgaaggac      1920
agttgggcga gaacaacgag cttagactga cccgtgatgc gctggagcct tgtaccgtgg     1980
gacatcgaag atacttcatc ttcggaggtg gatacgtgta tttcgaagaa tacgcctaca      2040
gtcatcagct ttctcgagcc gatgtgacta ccgtgagtac cttcatcgat cttaacatca      2100
ccatgctgga ggatcatgaa ttcgtgcctc tggaggtgta caccagacac gagattaagg      2160
attctggact tctggactat accgaagtgc agagaagaaa ccagctgcac gacctgagat      2220 cgccgacat cgacaccgtg atcagggcag atgctaacgc agccatgttc gcaggcctgt      2280
gcgccttctt cgaaggcatg ggcgatctag gcgggccgt tggaaaggtg gtgatgggcg      2340
tggtcggcgg agttgtaagt gctgtgtctg gcgtttcctc attcatgagc aacccttct       2400 tcttcatcat cggcctgatc ataggattgt tcctggtcct ccgagtgggc atccacctgt      2460
gcatcaagtt gaagcatact aagaagagac agatttatac ggacattgag atgaacagac      2520
tgggcaagtg ataataggct ggagcctcgg tggccatgct tcttgcccct gggcctccc       2580 cccagcccct cctcccttc ctgcacccgt accccgtgg tctttgaata aagtctgagt        2640
gggcggc                                                               2647
```

<210> SEQ ID NO 7
<211> LENGTH: 393
<212> TYPE: PRT
<213> ORGANISM: Artificial Sequence
<220> FEATURE:
<223> OTHER INFORMATION: HSV-2 gD, SQ-032180

<400> SEQUENCE: 7

```
Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
            20                  25                  30

Ser Leu Lys Met Ala Asp Pro Asn Arg Phe Arg Gly Lys Asn Leu Pro
        35                  40                  45

Val Leu Asp Gln Leu Thr Asp Pro Pro Gly Val Lys Arg Val Tyr His
50                  55                  60

Ile Gln Pro Ser Leu Glu Asp Pro Phe Gln Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
            115                 120                 125

Asp Asn Cys Ala Ile Pro Ile Thr Val Met Glu Tyr Thr Glu Cys Pro
130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
            195                 200                 205

Arg Ala Arg Ala Ser Cys Lys Tyr Ala Leu Pro Leu Arg Ile Pro Pro
210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
        290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
            340                 345                 350

Val Leu Val Ile Gly Gly Ile Ala Phe Trp Val Arg Arg Arg Ala Gln
            355                 360                 365

Met Ala Pro Lys Arg Leu Arg Leu Pro His Ile Arg Asp Asp Asp Ala
370                 375                 380

Pro Pro Ser His Gln Pro Leu Phe Tyr
385                 390

<210> SEQ ID NO 8
<211> LENGTH: 339
<212> TYPE: PRT
```

<213> ORGANISM: Artificial Sequence
<220> FEATURE:
<223> OTHER INFORMATION: HSV-2 SgD, SQ-032172 Peptide

<400> SEQUENCE: 8

Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
20 25 30

Ser Leu Lys Met Ala Asp Pro Asn Arg Phe Arg Gly Lys Asn Leu Pro
35 40 45

Val Leu Asp Gln Leu Thr Asp Pro Pro Gly Val Lys Arg Val Tyr His
50 55 60

Ile Gln Pro Ser Leu Glu Asp Pro Phe Gln Pro Pro Ser Ile Pro Ile
65 70 75 80

Thr Val Tyr Tyr Ala Val Leu Glu Arg Ala Cys Arg Ser Val Leu Leu
85 90 95

His Ala Pro Ser Glu Ala Pro Gln Ile Val Arg Gly Ala Ser Asp Glu
100 105 110

Ala Arg Lys His Thr Tyr Asn Leu Thr Ile Ala Trp Tyr Arg Met Gly
115 120 125

Asp Asn Cys Ala Ile Pro Ile Thr Val Met Glu Tyr Thr Glu Cys Pro
130 135 140

Tyr Asn Lys Ser Leu Gly Val Cys Pro Ile Arg Thr Gln Pro Arg Trp
145 150 155 160

Ser Tyr Tyr Asp Ser Phe Ser Ala Val Ser Glu Asp Asn Leu Gly Phe
165 170 175

Leu Met His Ala Pro Ala Phe Glu Thr Ala Gly Thr Tyr Leu Arg Leu
180 185 190

Val Lys Ile Asn Asp Trp Thr Glu Ile Thr Gln Phe Ile Leu Glu His
195 200 205

Arg Ala Arg Ala Ser Cys Lys Tyr Ala Leu Pro Leu Arg Ile Pro Pro
210 215 220

Ala Ala Cys Leu Thr Ser Lys Ala Tyr Gln Gln Gly Val Thr Val Asp
225 230 235 240

Ser Ile Gly Met Leu Pro Arg Phe Ile Pro Glu Asn Gln Arg Thr Val
245 250 255

Ala Leu Tyr Ser Leu Lys Ile Ala Gly Trp His Gly Pro Lys Pro Pro
260 265 270

Tyr Thr Ser Thr Leu Leu Pro Pro Glu Leu Ser Asp Thr Thr Asn Ala
275 280 285

Thr Gln Pro Glu Leu Val Pro Glu Asp Pro Glu Asp Ser Ala Leu Leu
290 295 300

Glu Asp Pro Ala Gly Thr Val Ser Ser Gln Ile Pro Pro Asn Trp His
305 310 315 320

Ile Pro Ser Ile Gln Asp Val Ala Pro His His Ala Pro Ala Ala Pro
325 330 335

Ser Asn Pro

<210> SEQ ID NO 9
<211> LENGTH: 901
<212> TYPE: PRT
<213> ORGANISM: Artificial Sequence
<220> FEATURE:
<223> OTHER INFORMATION: HSV-2 gB, SQ-032178 Peptide -continued

```
<400> SEQUENCE: 9

Met Arg Gly Gly Gly Leu Val Cys Ala Leu Val Val Gly Ala Leu Val
1               5                   10                  15

Ala Ala Val Ala Ser Ala Ala Pro Ala Pro Arg Ala Ser Gly Gly
            20                  25                  30

Val Ala Ala Thr Val Ala Ala Asn Gly Gly Pro Ala Ser Gln Pro Pro
            35                  40                  45

Pro Val Pro Ser Pro Ala Thr Thr Lys Ala Arg Lys Arg Lys Thr Lys
        50                  55                  60

Lys Pro Pro Lys Arg Pro Glu Ala Thr Pro Pro Asp Ala Asn Ala
65              70                  75                  80

Thr Val Ala Ala Gly His Ala Thr Leu Arg Ala His Leu Arg Glu Ile
                85                  90                  95

Lys Val Glu Asn Ala Asp Ala Gln Phe Tyr Val Cys Pro Pro Thr
            100                 105                 110

Gly Ala Thr Val Val Gln Phe Glu Gln Pro Arg Arg Cys Pro Thr Arg
            115                 120                 125

Pro Glu Gly Gln Asn Tyr Thr Glu Gly Ile Ala Val Val Phe Lys Glu
        130                 135                 140

Asn Ile Ala Pro Tyr Lys Phe Lys Ala Thr Met Tyr Tyr Lys Asp Val
145                 150                 155                 160

Thr Val Ser Gln Val Trp Phe Gly His Arg Tyr Ser Gln Phe Met Gly
                165                 170                 175

Ile Phe Glu Asp Arg Ala Pro Val Pro Phe Glu Glu Val Ile Asp Lys
            180                 185                 190

Ile Asn Ala Lys Gly Val Cys Arg Ser Thr Ala Lys Tyr Val Arg Asn
        195                 200                 205

Asn Met Glu Thr Thr Ala Phe His Arg Asp Asp His Glu Thr Asp Met
210                 215                 220

Glu Leu Lys Pro Ala Lys Val Ala Thr Arg Thr Ser Arg Gly Trp His
225                 230                 235                 240

Thr Thr Asp Leu Lys Tyr Asn Pro Ser Arg Val Glu Ala Phe His Arg
            245                 250                 255

Tyr Gly Thr Thr Val Asn Cys Ile Val Glu Glu Val Asp Ala Arg Ser
            260                 265                 270

Val Tyr Pro Tyr Asp Glu Phe Val Leu Ala Thr Gly Asp Phe Val Tyr
        275                 280                 285

Met Ser Pro Phe Tyr Gly Tyr Arg Glu Gly Ser His Thr Glu His Thr
290                 295                 300

Ser Tyr Ala Ala Asp Arg Phe Lys Gln Val Asp Gly Phe Tyr Ala Arg
305                 310                 315                 320

Asp Leu Thr Thr Lys Ala Arg Ala Thr Ser Pro Thr Thr Arg Asn Leu
            325                 330                 335

Leu Thr Thr Pro Lys Phe Thr Val Ala Trp Asp Trp Val Pro Lys Arg
            340                 345                 350

Pro Ala Val Cys Thr Met Thr Lys Trp Gln Glu Val Asp Glu Met Leu
        355                 360                 365

Arg Ala Glu Tyr Gly Gly Ser Phe Arg Phe Ser Ser Asp Ala Ile Ser
370                 375                 380

Thr Thr Phe Thr Thr Asn Leu Thr Gln Tyr Ser Leu Ser Arg Val Asp
385                 390                 395                 400

Leu Gly Asp Cys Ile Gly Arg Asp Ala Arg Glu Ala Ile Asp Arg Met
            405                 410                 415
```

```
Phe Ala Arg Lys Tyr Asn Ala Thr His Ile Lys Val Gly Gln Pro Gln
            420                 425                 430

Tyr Tyr Leu Ala Thr Gly Gly Phe Leu Ile Ala Tyr Gln Pro Leu Leu
            435                 440                 445

Ser Asn Thr Leu Ala Glu Leu Tyr Val Arg Glu Tyr Met Arg Glu Gln
450                 455                 460

Asp Arg Lys Pro Arg Asn Ala Thr Pro Ala Pro Leu Arg Glu Ala Pro
465                 470                 475                 480

Ser Ala Asn Ala Ser Val Glu Arg Ile Lys Thr Thr Ser Ser Ile Glu
                485                 490                 495

Phe Ala Arg Leu Gln Phe Thr Tyr Asn His Ile Gln Arg His Val Asn
            500                 505                 510

Asp Met Leu Gly Arg Ile Ala Val Ala Trp Cys Glu Leu Gln Asn His
            515                 520                 525

Glu Leu Thr Leu Trp Asn Glu Ala Arg Lys Leu Asn Pro Asn Ala Ile
            530                 535                 540

Ala Ser Ala Thr Val Gly Arg Arg Val Ser Ala Arg Met Leu Gly Asp
545                 550                 555                 560

Val Met Ala Val Ser Thr Cys Val Pro Val Ala Pro Asp Asn Val Ile
                565                 570                 575

Val Gln Asn Ser Met Arg Val Ser Ser Arg Pro Gly Thr Cys Tyr Ser
            580                 585                 590

Arg Pro Leu Val Ser Phe Arg Tyr Glu Asp Gln Gly Pro Leu Ile Glu
            595                 600                 605

Gly Gln Leu Gly Glu Asn Asn Glu Leu Arg Leu Thr Arg Asp Ala Leu
            610                 615                 620

Glu Pro Cys Thr Val Gly His Arg Arg Tyr Phe Ile Phe Gly Gly Gly
625                 630                 635                 640

Tyr Val Tyr Phe Glu Glu Tyr Ala Tyr Ser His Gln Leu Ser Arg Ala
                645                 650                 655

Asp Val Thr Thr Val Ser Thr Phe Ile Asp Leu Asn Ile Thr Met Leu
            660                 665                 670

Glu Asp His Glu Phe Val Pro Leu Glu Val Tyr Thr Arg His Glu Ile
            675                 680                 685

Lys Asp Ser Gly Leu Leu Asp Tyr Thr Glu Val Gln Arg Arg Asn Gln
            690                 695                 700

Leu His Asp Leu Arg Phe Ala Asp Ile Asp Thr Val Ile Arg Ala Asp
705                 710                 715                 720

Ala Asn Ala Ala Met Phe Ala Gly Leu Cys Ala Phe Phe Glu Gly Met
                725                 730                 735

Gly Asp Leu Gly Arg Ala Val Gly Lys Val Val Met Gly Val Val Gly
            740                 745                 750

Gly Val Val Ser Ala Val Ser Gly Val Ser Ser Phe Met Ser Asn Pro
            755                 760                 765

Phe Gly Ala Leu Ala Val Gly Leu Leu Val Leu Ala Gly Leu Val Ala
            770                 775                 780

Ala Phe Phe Ala Phe Arg Tyr Val Leu Gln Leu Gln Arg Asn Pro Met
785                 790                 795                 800

Lys Ala Leu Tyr Pro Leu Thr Thr Lys Glu Leu Lys Thr Ser Asp Pro
                805                 810                 815

Gly Gly Val Gly Gly Glu Gly Glu Glu Gly Ala Glu Gly Gly Gly Phe
            820                 825                 830
```

```
Asp Glu Ala Lys Leu Ala Glu Ala Arg Glu Met Ile Arg Tyr Met Ala
            835                 840                 845

Leu Val Ser Ala Met Glu Arg Thr Glu His Lys Ala Arg Lys Lys Gly
        850                 855                 860

Thr Ser Ala Leu Leu Ser Ser Lys Val Thr Asn Met Val Leu Arg Lys
865                 870                 875                 880

Arg Asn Lys Ala Arg Tyr Ser Pro Leu His Asn Glu Asp Glu Ala Gly
                885                 890                 895

Asp Glu Asp Glu Leu
            900

<210> SEQ ID NO 10
<211> LENGTH: 768
<212> TYPE: PRT
<213> ORGANISM: Artificial Sequence
<220> FEATURE:
<223> OTHER INFORMATION: HSV-2 SgB, SQ-032210 peptide

<400> SEQUENCE: 10

Met Arg Gly Gly Gly Leu Val Cys Ala Leu Val Val Gly Ala Leu Val
1               5                   10                  15

Ala Ala Val Ala Ser Ala Ala Pro Ala Ala Pro Arg Ala Ser Gly Gly
            20                  25                  30

Val

```
Met Ser Pro Phe Tyr Gly Tyr Arg Glu Gly Ser His Thr Glu His Thr
    290                 295                 300
Ser Tyr Ala Ala Asp Arg Phe Lys Gln Val Asp Gly Phe Tyr Ala Arg
305                 310                 315                 320
Asp Leu Thr Thr Lys Ala Arg Ala Thr Ser Pro Thr Thr Arg Asn Leu
                325                 330                 335
Leu Thr Thr Pro Lys Phe Thr Val Ala Trp Asp Trp Val Pro Lys Arg
                340                 345                 350
Pro Ala Val Cys Thr Met Thr Lys Trp Gln Glu Val Asp Glu Met Leu
                355                 360                 365
Arg Ala Glu Tyr Gly Gly Ser Phe Arg Phe Ser Ser Asp Ala Ile Ser
370                 375                 380
Thr Thr Phe Thr Thr Asn Leu Thr Gln Tyr Ser Leu Ser Arg Val Asp
385                 390                 395                 400
Leu Gly Asp Cys Ile Gly Arg Asp Ala Arg Glu Ala Ile Asp Arg Met
                405                 410                 415
Phe Ala Arg Lys Tyr Asn Ala Thr His Ile Lys Val Gly Gln Pro Gln
                420                 425                 430
Tyr Tyr Leu Ala Thr Gly Gly Phe Leu Ile Ala Tyr Gln Pro Leu Leu
                435                 440                 445
Ser Asn Thr Leu Ala Glu Leu Tyr Val Arg Glu Tyr Met Arg Glu Gln
                450                 455                 460
Asp Arg Lys Pro Arg Asn Ala Thr Pro Ala Pro Leu Arg Glu Ala Pro
465                 470                 475                 480
Ser Ala Asn Ala Ser Val Glu Arg Ile Lys Thr Thr Ser Ser Ile Glu
                485                 490                 495
Phe Ala Arg Leu Gln Phe Thr Tyr Asn His Ile Gln Arg His Val Asn
                500                 505                 510
Asp Met Leu Gly Arg Ile Ala Val Ala Trp Cys Glu Leu Gln Asn His
                515                 520                 525
Glu Leu Thr Leu Trp Asn Glu Ala Arg Lys Leu Asn Pro Asn Ala Ile
                530                 535                 540
Ala Ser Ala Thr Val Gly Arg Arg Val Ser Ala Arg Met Leu Gly Asp
545                 550                 555                 560
Val Met Ala Val Ser Thr Cys Val Pro Val Ala Pro Asp Asn Val Ile
                565                 570                 575
Val Gln Asn Ser Met Arg Val Ser Ser Arg Pro Gly Thr Cys Tyr Ser
                580                 585                 590
Arg Pro Leu Val Ser Phe Arg Tyr Glu Asp Gln Gly Pro Leu Ile Glu
                595                 600                 605
Gly Gln Leu Gly Glu Asn Asn Glu Leu Arg Leu Thr Arg Asp Ala Leu
                610                 615                 620
Glu Pro Cys Thr Val Gly His Arg Arg Tyr Phe Ile Phe Gly Gly Gly
625                 630                 635                 640
Tyr Val Tyr Phe Glu Glu Tyr Ala Tyr Ser His Gln Leu Ser Arg Ala
                645                 650                 655
Asp Val Thr Thr Val Ser Thr Phe Ile Asp Leu Asn Ile Thr Met Leu
                660                 665                 670
Glu Asp His Glu Phe Val Pro Leu Glu Val Tyr Thr Arg His Glu Ile
                675                 680                 685
Lys Asp Ser Gly Leu Leu Asp Tyr Thr Glu Val Gln Arg Arg Asn Gln
690                 695                 700
Leu His Asp Leu Arg Phe Ala Asp Ile Asp Thr Val Ile Arg Ala Asp
```

```
                705                 710                 715                 720

Ala Asn Ala Ala Met Phe Ala Gly Leu Cys Ala Phe Phe Glu Gly Met
                    725                 730                 735

Gly Asp Leu Gly Arg Ala Val Gly Lys Val Val Met Gly Val Val Gly
                740                 745                 750

Gly Val Val Ser Ala Val Ser Gly Val Ser Ser Phe Met Ser Asn Pro
                755                 760                 765

<210> SEQ ID NO 11
<211> LENGTH: 480
<212> TYPE: PRT
<213> ORGANISM: Artificial Sequence
<220> FEATURE:
<223> OTHER INFORMATION: HSV-2 gC, SQ-032179 peptide

<400> S

```
305                 310                 315                 320

His Arg Asp Ser Val Ser Phe Ser Arg Arg Asn Ala Ser Gly Thr Ala
                325                 330                 335

Ser Val Leu Pro Arg Pro Thr Ile Thr Met Glu Phe Thr Gly Asp His
            340                 345                 350

Ala Val Cys Thr Ala Gly Cys Val Pro Glu Gly Val Thr Phe Ala Trp
        355                 360                 365

Phe Leu Gly Asp Asp Ser Ser Pro Ala Glu Lys Val Ala Val Ala Ser
    370                 375                 380

Gln Thr Ser Cys Gly Arg Pro Gly Thr Ala Thr Ile Arg Ser Thr Leu
385                 390                 395                 400

Pro Val Ser Tyr Glu Gln Thr Glu Tyr Ile Cys Arg Leu Ala Gly Tyr
                405                 410                 415

Pro Asp Gly Ile Pro Val Leu Glu His His Gly Ser His Gln Pro Pro
            420                 425                 430

Pro Arg Asp Pro Thr Glu Arg Gln Val Ile Arg Ala Val Glu Gly Ala
        435                 440                 445

Gly Ile Gly Val Ala Val Leu Val Ala Val Val Leu Ala Gly Thr Ala
    450                 455                 460

Val Val Tyr Leu Thr His Ala Ser Ser Val Arg Tyr Arg Arg Leu Arg
465                 470                 475                 480

<210> SEQ ID NO 12
<211> LENGTH: 447
<212> TYPE: PRT
<213> ORGANISM: Artificial Sequence
<220> FEATURE:
<223> OTHER INFORMATION: HSV-2 SgC, SQ-032835 peptide

<400> SEQUENCE: 12

Met Ala Leu Gly Arg Val Gly Leu Ala Val Gly Leu Trp Gly Leu Leu
1               5                   10                  15

Trp Val Gly Val Val Val Val Leu Ala Asn Ala Ser Pro Gly Arg Thr
            20                  25                  30

Ile Thr Val Gly Pro Arg Gly Asn Ala Ser Asn Ala Ala Pro Ser Ala
        35                  40                  45

Ser Pro Arg Asn Ala Ser Ala Pro Arg Thr Thr Pro Thr Pro Pro Gln
    50                  55                  60

Pro Arg Lys Ala Thr Lys Ser Lys Ala Ser Thr Ala Lys Pro Ala Pro
65                  70                  75                  80

Pro Pro Lys Thr Gly Pro Pro Lys Thr Ser Ser Glu Pro Val Arg Cys
                85                  90                  95

Asn Arg His Asp Pro Leu Ala Arg Tyr Gly Ser Arg Val Gln Ile Arg
            100                 105                 110

Cys Arg Phe Pro Asn Ser Thr Arg Thr Glu Ser Arg Leu Gln Ile Trp
        115                 120                 125

Arg Tyr Ala Thr Ala Thr Asp Ala Glu Ile Gly Thr Ala Pro Ser Leu
    130                 135                 140

Glu Glu Val Met Val Asn Val Ser Ala Pro Pro Gly Gly Gln Leu Val
145                 150                 155                 160

Tyr Asp Ser Ala Pro Asn Arg Thr Asp Pro His Val Ile Trp Ala Glu
                165                 170                 175

Gly Ala Gly Pro Gly Ala Ser Pro Arg Leu Tyr Ser Val Val Gly Pro
            180                 185                 190

Leu Gly Arg Gln Arg Leu Ile Ile Glu Glu Leu Thr Leu Glu Thr Gln
```

-continued

```
                 195                 200                 205
Gly Met Tyr Tyr Trp Val Trp Gly Arg Thr Asp Arg Pro Ser Ala Tyr
    210                 215                 220
Gly Thr Trp Val Arg Val Arg Val Phe Arg Pro Pro Ser Leu Thr Ile
225                 230                 235                 240
His Pro His Ala Val Leu Glu Gly Gln Pro Phe Lys Ala Thr Cys Thr
                245                 250                 255
Ala Ala Thr Tyr Tyr Pro Gly Asn Arg Ala Glu Phe Val Trp Phe Glu
            260                 265                 270
Asp Gly Arg Arg Val Phe Asp Pro Ala Gln Ile His Thr Gln Thr Gln
        275                 280                 285
Glu Asn Pro Asp Gly Phe Ser Thr Val Ser Thr Val Thr Ser Ala Ala
    290                 295                 300
Val Gly Gly Gln Gly Pro Pro Arg Thr Phe Thr Cys Gln Leu Thr Trp
305                 310                 315                 320
His Arg Asp Ser Val Ser Phe Ser Arg Arg Asn Ala Ser Gly Thr Ala
                325                 330                 335
Ser Val Leu Pro Arg Pro Thr Ile Thr Met Glu Phe Thr Gly Asp His
            340                 345                 350
Ala Val Cys Thr Ala Gly Cys Val Pro Glu Gly Val Thr Phe Ala Trp
        355                 360                 365
Phe Leu Gly Asp Asp Ser Ser Pro Ala Glu Lys Val Ala Val Ala Ser
    370                 375                 380
Gln Thr Ser Cys Gly Arg Pro Gly Thr Ala Thr Ile Arg Ser Thr Leu
385                 390                 395                 400
Pro Val Ser Tyr Glu Gln Thr Glu Tyr Ile Cys Arg Leu Ala Gly Tyr
                405                 410                 415
Pro Asp Gly Ile Pro Val Leu Glu His His Gly Ser His Gln Pro Pro
            420                 425                 430
Pro Arg Asp Pro Thr Glu Arg Gln Val Ile Arg Ala Val Glu Gly
        435                 440                 445

<210> SEQ ID NO 13
<211> LENGTH: 548
<212> TYPE: PRT
<213> ORGANISM: Artificial Sequence
<220> FEATURE:
<223> OTHER INFORMATION: HSV-2 gE, SQ-032181

<400> SEQUENCE: 13

Met Ala Arg Gly Ala Gly Leu Val Phe Phe Val Gly Val Trp Val Val
1               5                   10                  15
Ser Cys Leu Ala Ala Ala Pro Arg Thr Ser Trp Lys Arg Val Thr Ser
                20                  25                  30
Gly Glu Asp Val Val Leu Leu Pro Ala Pro Ala Gly Pro Glu Glu Arg
            35                  40                  45
Thr Arg Ala His Lys Leu Leu Trp Ala Ala Glu Pro Leu Asp Ala Cys
        50                  55                  60
Gly Pro Leu Arg Pro Ser Trp Val Ala Leu Trp Pro Pro Arg Arg Val
65                  70                  75                  80
Leu Glu Thr Val Val Asp Ala Ala Cys Met Arg Ala Pro Glu Pro Leu
                85                  90                  95
Ala Ile Ala Tyr Ser Pro Pro Phe Pro Ala Gly Asp Glu Gly Leu Tyr
            100                 105                 110
Ser Glu Leu Ala Trp Arg Asp Arg Val Ala Val Val Asn Glu Ser Leu
```

```
            115                 120                 125
Val Ile Tyr Gly Ala Leu Glu Thr Asp Ser Gly Leu Tyr Thr Leu Ser
            130                 135                 140
Val Val Gly Leu Ser Asp Glu Ala Arg Gln Val Ala Ser Val Val Leu
145                 150                 155                 160
Val Val Glu Pro Ala Pro Val Pro Thr Pro Thr Pro Asp Asp Tyr Asp
                    165                 170                 175
Glu Glu Asp Asp Ala Gly Val Ser Glu Arg Thr Pro Val Ser Val Pro
                    180                 185                 190
Pro Pro Thr Pro Pro Arg Arg Pro Pro Val Ala Pro Thr His Pro
                    195                 200                 205
Arg Val Ile Pro Glu Val Ser His Val Arg Gly Val Thr Val His Met
                    210                 215                 220
Glu Thr Pro Glu Ala Ile Leu Phe Ala Pro Gly Glu Thr Phe Gly Thr
225                 230                 235                 240
Asn Val Ser Ile His Ala Ile His Asp Asp Gly Pro Tyr Ala Met
                    245                 250                 255
Asp Val Val Trp Met Arg Phe Asp Val Pro Ser Ser Cys Ala Glu Met
                    260                 265                 270
Arg Ile Tyr Glu Ala Cys Leu Tyr His Pro Gln Leu Pro Glu Cys Leu
                    275                 280                 285
Ser Pro Ala Asp Ala Pro Cys Ala Val Ser Ser Trp Ala Tyr Arg Leu
290                 295                 300
Ala Val Arg Ser Tyr Ala Gly Cys Ser Arg Thr Thr Pro Pro Arg
305                 310                 315                 320
Cys Phe Ala Glu Ala Arg Met Glu Pro Val Pro Gly Leu Ala Trp Leu
                    325                 330                 335
Ala Ser Thr Val Asn Leu Glu Phe Gln His Ala Ser Pro Gln His Ala
                    340                 345                 350
Gly Leu Tyr Leu Cys Val Val Tyr Val Asp Asp His Ile His Ala Trp
            355                 360                 365
Gly His Met Thr Ile Ser Thr Ala Ala Gln Tyr Arg Asn Ala Val Val
            370                 375                 380
Glu Gln His Leu Pro Gln Arg Gln Pro Glu Pro Val Glu Pro Thr Arg
385                 390                 395                 400
Pro His Val Arg Ala Pro Pro Ala Pro Ser Ala Arg Gly Pro Leu
                    405                 410                 415
Arg Leu Gly Ala Val Leu Gly Ala Ala Leu Leu Ala Ala Leu Gly
                    420                 425                 430
Leu Ser Ala Trp Ala Cys Met Thr Cys Trp Arg Arg Ser Trp Arg
            435                 440                 445
Ala Val Lys Ser Arg Ala Ser Ala Thr Gly Pro Thr Tyr Ile Arg Val
            450                 455                 460
Ala Asp Ser Glu Leu Tyr Ala Asp Trp Ser Ser Asp Ser Glu Gly Glu
465                 470                 475                 480
Arg Asp Gly Ser Leu Trp Gln Asp Pro Pro Glu Arg Pro Asp Ser Pro
                    485                 490                 495
Ser Thr Asn Gly Ser Gly Phe Glu Ile Leu Ser Pro Thr Ala Pro Ser
                    500                 505                 510
Val Tyr Pro His Ser Glu Gly Arg Lys Ser Arg Arg Pro Leu Thr Thr
            515                 520                 525
Phe Gly Ser Gly Ser Pro Gly Arg Arg His Ser Gln Ala Ser Tyr Ser
            530                 535                 540
```

Ser Val Leu Trp
545

<210> SEQ ID NO 14
<211> LENGTH: 417
<212> TYPE: PRT
<213> ORGANISM: Artificial Sequence
<220> FEATURE:
<223> OTHER INFORMATION: HSV-2 SgE, SQ-032211 peptide

<400> SEQUENCE: 14

Met Ala Arg Gly Ala Gly Leu Val Phe Phe Val Gly Val Trp Val Val
1               5                   10                  15

Ser Cys Leu Ala Ala Pro Arg Thr Ser Trp Lys Arg Val Thr Ser
                20                  25                  30

Gly Glu Asp Val Val Leu Leu Pro Ala Pro Ala Gly Pro Glu Glu Arg
            35                  40                  45

Thr Arg Ala His Lys Leu Leu Trp Ala Ala Glu Pro Leu Asp Ala Cys
        50                  55                  60

Gly Pro Leu Arg Pro Ser Trp Val Ala Leu Trp Pro Pro Arg Arg Val
65                  70                  75                  80

Leu Glu Thr Val Val Asp Ala Ala Cys Met Arg Ala Pro Glu Pro Leu
                85                  90                  95

Ala Ile Ala Tyr Ser Pro Pro Phe Pro Ala Gly Asp Glu Gly Leu Tyr
            100                 105                 110

Ser Glu Leu Ala Trp Arg Asp Arg Val Ala Val Val Asn Glu Ser Leu
        115                 120                 125

Val Ile Tyr Gly Ala Leu Glu Thr Asp Ser Gly Leu Tyr Thr Leu Ser
130                 135                 140

Val Val Gly Leu Ser Asp Glu Ala Arg Gln Val Ala Ser Val Val Leu
145                 150                 155                 160

Val Val Glu Pro Ala Pro Val Pro Thr Pro Thr Pro Asp Asp Tyr Asp
                165                 170                 175

Glu Glu Asp Asp Ala Gly Val Ser Glu Arg Thr Pro Val Ser Val Pro
            180                 185                 190

Pro Pro Thr Pro Pro Arg Arg Pro Pro Val Ala Pro Pro Thr His Pro
        195                 200                 205

Arg Val Ile Pro Glu Val Ser His Val Arg Gly Val Thr Val His Met
    210                 215                 220

Glu Thr Pro Glu Ala Ile Leu Phe Ala Pro Gly Glu Thr Phe Gly Thr
225                 230                 235                 240

Asn Val Ser Ile His Ala Ile Ala His Asp Asp Gly Pro Tyr Ala Met
                245                 250                 255

Asp Val Val Trp Met Arg Phe Asp Val Pro Ser Ser Cys Ala Glu Met
            260                 265                 270

Arg Ile Tyr Glu Ala Cys Leu Tyr His Pro Gln Leu Pro Glu Cys Leu
        275                 280                 285

Ser Pro Ala Asp Ala Pro Cys Ala Val Ser Ser Trp Ala Tyr Arg Leu
    290                 295                 300

Ala Val Arg Ser Tyr Ala Gly Cys Ser Arg Thr Thr Pro Pro Pro Arg
305                 310                 315                 320

Cys Phe Ala Glu Ala Arg Met Glu Pro Val Pro Gly Leu Ala Trp Leu
                325                 330                 335

Ala Ser Thr Val Asn Leu Glu Phe Gln His Ala Ser Pro Gln His Ala
            340                 345                 350

```
Gly Leu Tyr Leu Cys Val Val Tyr Val Asp Asp His Ile His Ala Trp
            355                 360                 365

Gly His Met Thr Ile Ser Thr Ala Ala Gln Tyr Arg Asn Ala Val Val
        370                 375                 380

Glu Gln His Leu Pro Gln Arg Gln Pro Glu Pro Val Glu Pro Thr Arg
385                 390                 395                 400

Pro His Val Arg Ala Pro Pro Ala Pro Ser Ala Arg Gly Pro Leu
            405                 410                 415

Arg

<210> SEQ ID NO 15
<211> LENGTH: 372
<212> TYPE: PRT
<213> ORGANISM: Artificial Sequence
<220> FEATURE:
<223> OTHER INFORMATION: HSV-2 gI, SQ-032182 peptide

<400> SEQUENCE: 15

Met Pro Gly Arg Ser Leu Gln Gly Leu Ala Ile Leu Gly Leu Trp Val
1               5                   10                  15

Cys Ala Thr Gly Leu Val Val Arg Gly Pro Thr Val Ser Leu Val Ser
            20                  25                  30

Asp Ser Leu Val Asp Ala Gly Ala Val Gly Pro Gln Gly Phe Val Glu
        35                  40                  45

Glu Asp Leu Arg Val Phe Gly Glu Leu His Val Gly Ala Gln Val
    50                  55                  60

Pro His Thr Asn Tyr Tyr Asp Gly Ile Ile Glu Leu Phe His Tyr Pro
65                  70                  75                  80

Leu Gly Asn His Cys Pro Arg Val Val His Val Val Thr Leu Thr Ala
                85                  90                  95

Cys Pro Arg Arg Pro Ala Val Ala Phe Thr Leu Cys Arg Ser Thr His
            100                 105                 110

His Ala His Ser Pro Ala Tyr Pro Thr Leu Glu Leu Gly Leu Ala Arg
        115                 120                 125

Gln Pro Leu Leu Arg Val Arg Thr Ala Thr Arg Asp Tyr Ala Gly Leu
    130                 135                 140

Tyr Val Leu Arg Val Trp Val Gly Ser Ala Thr Asn Ala Ser Leu Phe
145                 150                 155                 160

Val Leu Gly Val Ala Leu Ser Ala Asn Gly Thr Phe Val Tyr Asn Gly
                165                 170                 175

Ser Asp Tyr Gly Ser Cys Asp Pro Ala Gln Leu Pro Phe Ser Ala Pro
            180                 185                 190

Arg Leu Gly Pro Ser Ser Val Tyr Thr Pro Gly Ala Ser Arg Pro Thr
        195                 200                 205

Pro Pro Arg Thr Thr Thr Ser Pro Ser Ser Pro Arg Asp Pro Thr Pro
    210                 215                 220

Ala Pro Gly Asp Thr Gly Thr Pro Ala Pro Ala Ser Gly Glu Arg Ala
225                 230                 235                 240

Pro Pro Asn Ser Thr Arg Ser Ala Ser Glu Ser Arg His Arg Leu Thr
                245                 250                 255

Val Ala Gln Val Ile Gln Ile Ala Ile Pro Ala Ser Ile Ile Ala Phe
            260                 265                 270

Val Phe Leu Gly Ser Cys Ile Cys Phe Ile His Arg Cys Gln Arg Arg
        275                 280                 285
```

```
Tyr Arg Arg Pro Arg Gly Gln Ile Tyr Asn Pro Gly Gly Val Ser Cys
    290             295                 300
Ala Val Asn Glu Ala Ala Met Ala Arg Leu Gly Ala Glu Leu Arg Ser
305             310                 315                 320
His Pro Asn Thr Pro Pro Lys Pro Arg Arg Ser Ser Ser Thr
                325                 330                 335
Thr Met Pro Ser Leu Thr Ser Ile Ala Glu Glu Ser Glu Pro Gly Pro
            340                 345                 350
Val Val Leu Leu Ser Val Ser Pro Arg Pro Arg Ser Gly Pro Thr Ala
                355                 360                 365
Pro Gln Glu Val
    370
```

<210> SEQ ID NO 16
<211> LENGTH: 262
<212> TYPE: PRT
<213> ORGANISM: Artificial Sequence
<220> FEATURE:
<223> OTHER INFORMATION: HSV-2 SgI, SQ-032323 peptide

<400> SEQUENCE: 16

```
Met Pro Gly Arg Ser Leu Gln Gly Leu Ala Ile Leu Gly Leu Trp Val
1               5                   10                  15
Cys Ala Thr Gly Leu Val Val Arg Gly Pro Thr Val Ser Leu Val Ser
                20                  25                  30
Asp Ser Leu Val Asp Ala Gly Ala Val Gly Pro Gln Gly Phe Val Glu
            35                  40                  45
Glu Asp Leu Arg Val Phe Gly Glu Leu His Phe Val G

What is claimed is:

1. An immunogenic composition comprising at least one isolated antigenic polypeptide selected from the group consisting of:
   (i) a mature HSV chimeric glycoprotein B amino acid sequence of SEQ ID NO: 1, or a variant thereof;
   (ii) a mature HSV glycoprotein C amino acid sequence of SEQ ID NO: 2, or variant thereof;
   (iii) a mature HSV glycoprotein C amino acid sequence of SEQ ID NO:3, or variant thereof
   (iv) a mature HSV glycoprotein C amino acid sequence of SEQ ID NO:4, or variant thereof; and
   (v) a mature HSV glycoprotein C amino acid sequence of SEQ ID NO: 5, or a variant thereof;
   wherein the variant of any one of SEQ ID NOs: 1-5 comprises at least 90% identity as compared to the sequence of any one of SEQ ID NOs: 1-5 using the Needleman-Wunsch algorithm,
   provided that the variant of SEQ ID NO: 2 comprises an alanine at position 368; the variant of SEQ ID NO: 3 comprises an alanine at position 323; the variant of SEQ ID NO: 4 comprises an alanine at position 327; and the variant of SEQ ID NO: 5 comprises an alanine at position 333.

2. The immunogenic composition of claim 1, wherein the at least one isolated antigenic polypeptide is a variant of any one of SEQ ID NOs: 1-5, which variant comprises 1-10 conservative amino acid mutations as compared to the sequence of any one of SEQ ID NOs: 1-5.

3. The immunogenic composition of claim 1, wherein the at least one isolated antigenic polypeptide consists of the mature amino acid sequence of SEQ ID NOs: 1-5.

4. The immunogenic composition of claim 1 comprising at least two isolated antigenic polypeptides, wherein the first isolated antigenic polypeptide comprises a mature HSV glycoprotein B amino acid sequence of SEQ ID NO: 1, or a variant thereof, and the second isolated antigenic polypeptide comprises an HSV glycoprotein D or immunogenic fragment thereof.

5. The immunogenic composition of claim 4, further comprising a third isolated antigenic polypeptide, wherein the third isolated antigenic polypeptide comprises a mature HSV glycoprotein C amino acid sequence of any of SEQ_ID NOs: 2-5.

6. The immunogenic composition of claim 1 comprising at least two isolated antigenic polypeptides, wherein the first isolated antigenic polypeptide comprises a mature HSV glycoprotein C amino acid sequence of any of SEQ ID NOs: 2-5, or a variant thereof, and the second isolated antigenic polypeptide comprises an HSV glycoprotein D or immunogenic fragment thereof.

7. The immunogenic composition of claim 1 comprising at least two isolated antigenic polypeptides, wherein the first isolated antigenic polypeptide comprises a mature HSV glycoprotein B amino acid sequence of SEQ ID NO: 1, or a variant thereof, and the second polypeptide comprises a mature HSV glycoprotein C amino acid sequence of any of SEQ ID NOs: 2-5, or a variant thereof.

8. The immunogenic composition of claim 7, comprising a third isolated antigenic polypeptide, wherein the third isolated antigenic polypeptide comprises an HSV glycoprotein D or immunogenic fragment thereof.

9. A pharmaceutical composition comprising the immunogenic composition of claim 1 in combination with one or more pharmaceutically acceptable excipients.

10. A method of inducing an immune response in a subject, the method comprising administering to the subject the immunogenic composition of claim 1 in an amount effective to produce an antigen-specific immune response in the subject.

11. An isolated peptide comprising the amino acid sequence of any one of SEQ ID NOs: 1-5 or the mature amino acid sequence of any one of SEQ ID NOs: 1-5, or a variant thereof, wherein the variant of SEQ ID NO: 2 comprises an alanine at position 368; the variant of SEQ ID NO: 3 comprises an alanine at position 323; the variant of SEQ ID NO: 4 comprises an alanine at position 327; and the variant of SEQ ID NO: 5 comprises an alanine at position 333.

12. The immunogenic composition of claim 1, the at least one isolated antigenic polypeptide comprising a mature amino acid sequence of SEQ ID NO: 1, or variant thereof.

13. The immunogenic composition of claim 12, wherein the at least one isolated antigenic polypeptide is a variant of the mature amino acid sequence of SEQ ID NO: 1, the variant of SEQ ID NO: 1 comprising 1-10 conservative amino acid mutations as compared to the sequence of SEQ ID NO: 1.

14. The immunogenic composition of claim 1, the at least one isolated antigenic polypeptide comprising a mature amino acid sequence of SEQ ID NO: 2, or variant thereof, wherein the variant of SEQ ID NO: 2 comprises an alanine at position 368.

15. The immunogenic composition of claim 14, wherein the at least one isolated antigenic polypeptide is a variant of the mature amino acid sequence of SEQ ID NO: 2, the variant of SEQ ID NO: 2 comprising 1-10 conservative amino acid mutations as compared to the sequence of SEQ ID NO: 2.

16. The immunogenic composition of claim 1, the at least one isolated antigenic polypeptide comprising a mature amino acid sequence of SEQ ID NO: 3, or variant thereof, wherein the variant of SEQ ID NO: 3 comprises an alanine at position 323.

17. The immunogenic composition of claim 16, wherein the isolated antigenic polypeptide is the variant of SEQ ID NO: 3, the variant of SEQ ID NO: 3 comprising 1-10 conservative amino acid mutations as compared to the sequence of SEQ ID NO: 3.

18. The immunogenic composition of claim 1, the at least one isolated antigenic polypeptide comprising a mature amino acid sequence of SEQ ID NO: 4, or variant thereof, wherein the variant of SEQ ID NO: 4 comprises an alanine at position 327.

19. The immunogenic composition of claim 18, wherein the isolated antigenic polypeptide is the variant of SEQ ID NO: 4, the variant of SEQ ID NO: 4 comprising 1-10 conservative amino acid mutations as compared to the sequence of SEQ ID NO: 4.

20. The immunogenic composition of claim 1, the isolated antigenic polypeptide comprising a mature amino acid sequence of SEQ ID NO: 5, or variant thereof, wherein the variant of SEQ ID NO: 5 comprises an alanine at position 333.

21. The immunogenic composition of claim 20, wherein the isolated antigenic polypeptide is a variant of SEQ ID NO: 5, the variant of SEQ ID NO: 5 comprising 1-10 conservative amino acid mutations as compared to the sequence of SEQ ID NO: 5.

* * * * *